US012686653B2

(12) United States Patent
Van Daele et al.

(10) Patent No.: US 12,686,653 B2
(45) Date of Patent: Jul. 21, 2026

(54) PROCESS FOR CATALYTIC NON-OXIDATIVE CONVERSION OF SATURATED HYDROCARBONS USING A CARBON-BASED CATALYST

(71) Applicants: TOTALENERGIES ONETECH, Courbevoie (FR); UNIVERSITÉ DE STRASBOURG-UNISTRA, Strasbourg Cedex (FR); CENTRE NATIONAL DE LA RECHERCHE SCIENTIFIQUE-CNRS, Paris Cedex (FR)

(72) Inventors: Stijn Van Daele, Seneffe (BE); Nikolai Nesterenko, Seneffe (BE); Jean-Pierre Dath, Seneffe (BE); Miroslave Kettner, Seneffe (BE); Cuong Pham-Huu, Strasbourg (FR); Jean-Mario Nhut, Plobsheim (FR); Zhenxin Xu, Shanxi (CN)

(73) Assignees: TOTALENERGIES ONETECH, Courbevoie (FR); UNIVERSITÉ DE STRASBOURG-UNISTRA, Strasbourg Cedex (FR); CENTRE NATIONAL DE LA RECHERCHE SCIENTIFIQUE-CNRS, Paris Cedex (FR)

( * ) Notice: Subject to any disclaimer, the term of this patent is extended or adjusted under 35 U.S.C. 154(b) by 122 days.

(21) Appl. No.: 18/695,178

(22) PCT Filed: Oct. 26, 2022

(86) PCT No.: PCT/EP2022/079893
§ 371 (c)(1),
(2) Date: Mar. 25, 2024

(87) PCT Pub. No.: WO2023/072996
PCT Pub. Date: May 4, 2023

(65) Prior Publication Data
US 2024/0391851 A1     Nov. 28, 2024

(30) Foreign Application Priority Data

Oct. 27, 2021    (EP) ...................................... 21306494

(51) Int. Cl.
*C07C 2/76* (2006.01)
*B01J 21/18* (2006.01)
(Continued)

(52) U.S. Cl.
CPC ................. *C07C 2/76* (2013.01); *B01J 21/18* (2013.01); *B01J 35/45* (2024.01); *B01J 35/612* (2024.01);
(Continued)

(58) Field of Classification Search
CPC ......... C07C 11/04; C07C 11/24; C07C 15/04; C07C 15/06; C07C 2/76; B01J 21/18;
(Continued)

(56) References Cited

U.S. PATENT DOCUMENTS 10,987,646 B2     4/2021   Højlund Nielsen et al.
2005/0084441 A1    4/2005   Xu et al.
(Continued)

FOREIGN PATENT DOCUMENTS

CN      107661755 A     2/2018
EP       3546438 A1 * 10/2019   .............. B01J 21/04
KR     20140071033 A     6/2014

OTHER PUBLICATIONS

International Search Report and Written Opinion dated Feb. 2, 2023 from International Patent Application PCT/EP2022/079893.
(Continued)

*Primary Examiner* — Latosha Hines
(74) *Attorney, Agent, or Firm* — Amster, Rothstein & Ebenstein LLP

(57) ABSTRACT
The present invention relates to a process for the non-oxidative conversion of saturated $C_{1+}$ hydrocarbons into
(Continued)

unsaturated $C_{2+}$ hydrocarbons and hydrogen in the presence of an unsupported carbon-based catalyst having a carbon content of at least 90.0 wt % and a metal concentration which is less than 0.3 wt %; with wt % expressed based on the total weight of said carbon-based catalyst. The present invention also provides a process for producing a graphite derivative. Further provided are a graphite derivative, and uses thereof, and systems for carrying out the processes of the invention.

22 Claims, 15 Drawing Sheets

(51) Int. Cl.

| | |
|---|---|
| *B01J 35/45* | (2024.01) |
| *B01J 35/61* | (2024.01) |
| *C01B 3/26* | (2006.01) |
| *C07C 11/04* | (2006.01) |
| *C07C 11/24* | (2006.01) |
| *C07C 15/04* | (2006.01) |
| *C07C 15/06* | (2006.01) |
| *C10G 50/00* | (2006.01) |

(52) U.S. Cl.
CPC ........... *B01J 35/613* (2024.01); *B01J 35/615* (2024.01); *C01B 3/26* (2013.01); *C07C 11/04* (2013.01); *C07C 11/24* (2013.01); *C07C 15/04* (2013.01); *C07C 15/06* (2013.01); *C10G 50/00* (2013.01); *C01B 2203/0855* (2013.01); *C10G 2300/1025* (2013.01); *C10G 2300/4006* (2013.01); *C10G 2300/4012* (2013.01); *C10G 2300/4018* (2013.01); *C10G 2300/70* (2013.01); *C10G 2400/24* (2013.01); *C10G 2400/30* (2013.01)

(58) Field of Classification Search
CPC ........ B01J 21/185; B01J 23/755; B01J 35/45; B01J 35/612; B01J 35/613; B01J 35/615; C01B 2203/0855; C01B 3/26; C10G 2300/1025; C10G 2300/4006; C10G 2300/4012; C10G 2300/4018; C10G 2300/70; C10G 2400/24; C10G 2400/30; C10G 50/00
See application file for complete search history.

(56) References Cited

U.S. PATENT DOCUMENTS

| | | | |
|---|---|---|---|
| 2014/0011972 A1* | 1/2014 | Bielawski | C08G 69/04 |
| | | | 528/214 |
| 2017/0088490 A1* | 3/2017 | Chen | B01J 27/043 |
| 2017/0106360 A1* | 4/2017 | Meriam | C10G 9/24 |
| 2018/0311630 A1 | 11/2018 | Højlund Nielsen et al. | |

OTHER PUBLICATIONS

Chinese Office Action as Issued on Mar. 2, 2026 in Respect to Chinese Patent Application No. 202280072500.9 and Its English Translation.

* cited by examiner

Impregnation

Chemical vapor deposition (CVD)

PROCESS FOR CATALYTIC NON-OXIDATIVE CONVERSION OF SATURATED HYDROCARBONS USING A CARBON-BASED CATALYST

CROSS-REFERENCE TO RELATED APPLICATIONS

This application is a U.S. national stage entry under 35 U.S.C. § 371 of PCT International Patent Application No. PCT/EP2022/079893, filed Oct. 26, 2022, which claims priority to European Patent Application No. 21306494.2, filed Oct. 27, 2021, the contents of each of which are incorporated herein by reference in their entirety.

FIELD OF THE INVENTION

The present invention relates to a process and a system for the non-oxidative conversion of saturated hydrocarbons into unsaturated hydrocarbons and hydrogen in the presence of at least one carbon-based catalyst. The present invention in particular relates to a process and a system for the non-oxidative conversion of saturated $C_{1+}$ hydrocarbons into unsaturated $C_{2+}$ hydrocarbons, such as e.g. ethylene and acetylene, and hydrogen in the presence of at least one carbon-based catalyst. The present process and system are in particular characterised in that they involve an endothermic catalytic chemical reaction, wherein the heat required for carrying out the conversion process is provided by heating a carbon-based catalyst by induction heating.

BACKGROUND

Hydrocarbons, including unsaturated hydrocarbons such as olefins (alkenes), alkynes, and/or aromatics, are important chemicals useful in a variety of processes for making plastics and other chemical compounds. Unsaturated hydrocarbons are for instance widely used for making pesticides, fuel, paints, and many other necessities. Ethylene is for instance used in the production of polyethylene and polyvinyl chloride plastics, ethylene oxide, ethylene chloride, ethylbenzene, alpha-olefins, linear alcohols, vinyl acetate, and fuel blend stocks such as, but not limited to, aromatics, alkanes and alkenes. With economic growth in developed and developing portions of the world, the demand for unsaturated hydrocarbons and derivatives thereof continues to increase.

Hydrocarbons, such as unsaturated hydrocarbons, are traditionally produced from petroleum feedstocks by catalytic or steam cracking processes.

In steam cracking, a gaseous or liquid hydrocarbon feed that primarily originate from fossil resources is diluted with steam and briefly heated in the absence of oxygen at elevated temperatures in tubular reactors suspended in a gas-fired furnace. A steam cracker is one of the most technically complex and energy intensive plants in the chemical industry. It has equipment operating from 100 K to 1400 K and near vacuum to 100 atm. Steam cracking plants use a variety of feedstocks, for example ethane, propane and butane from natural gas; naphtha, a mixture of $C_5$ to $C_{10}$ hydrocarbons, from the distillation of crude oil; or gas oil and residues. The reaction temperature is very high and the reaction occurs rapidly: the residence time is on the order of milliseconds. After the cracking temperature has been reached, the gas is quickly quenched to stop the reaction and to prevent loss via side reactions and the gas is separated in a series of processes including compression, absorption, drying, refrigeration, fractionation and selective hydrogenation. It is important to ensure that the feedstock does not crack to form carbon, which is normally formed at applied temperatures. This is avoided by passing the gaseous feedstock very quickly and at very low pressure through pipes which run through the furnace. The steam acts as a diluent and inhibits secondary reactions to generate carbon deposit. The products produced in the reaction depend on different aspects such as for instance the composition of the feed, the hydrocarbon-to-steam ratio, cracking temperature, pressure, and furnace residence time. Light hydrocarbon feeds such as ethane, LPGs, or light naphtha give mainly lighter alkenes, including ethylene, propylene, and butadiene. Heavier hydrocarbon (full range and heavy naphthas as well as other refinery products) feeds give some of these same products, but also those rich in aromatic hydrocarbons and hydrocarbons suitable for inclusion in gasoline or fuel oil. From the forgoing it is clear that steam cracking processes apply severe reaction conditions and suffer from high production costs due to the use of petroleum feedstock, and the energy consumption in the furnace.

Other methods to prepare unsaturated hydrocarbons include catalytic cracking processes. For instance, in fluidised catalytic cracking processes, the feedstock is gas, oil, which is vaporised and passed through a zeolite, produced as a fine powder, and heated in a reactor through gas-fired furnace. Temperature, residence time and the catalyst nature determine the product proportions. After cracking, the catalyst must be separated from the products, and regenerated by burning off carbon (coke) deposited on the catalyst, and subsequently recycled. Such combustion processes increase the CO and $CO_2$ emissions of the overall process. Ideally, the latter should be avoided or at least minimized. Fine formation through mechanical impacts also calls for replacing part of the catalyst periodically.

Limited supply and increasing cost of crude oil has prompted the search for alternative processes for producing (unsaturated) hydrocarbon products.

In an example, methanol-to-olefins process (MTO) is one of the technologies that can produce basic petrochemicals such as light olefins using zeolite as catalyst. The two commonly used catalysts in such process are ZSM-5 (MFI-type) and SAPO-34 (CHA-type). MFI is a medium pore sized alumina-silicate with ten membered ring pores. MFI is highly selective toward propylene and butylene. However, the yield of short olefins is less than in SAPO-34. SAPO-34 is a silico-alumino-phosphate with small eight-membered ring pores, which has high selectivity towards ethylene but suffers from fast deactivation due to extensive coke formation. Therefore, in general zeolites have deactivation problems and generally low selectivity to olefins (i.e. less than 50%).

Methane may provide an attractive alternative feedstock for the production of hydrocarbon intermediates and liquid fuels due to its widespread availability and relatively low cost when compared to crude oil. Methane is thermodynamically one of the most stable hydrocarbons and occurs in abundance in natural gas. Natural gas typically contains about 60-100 mol percent methane, the balance being primarily heavier alkanes. Alkanes of increasing carbon number are normally present in decreasing amounts. Carbon dioxide, hydrogen sulphide, nitrogen, and other gases may be present in relatively low concentrations.

The direct conversion of natural gas into valuable hydrocarbons has been a technological goal for many years. This goal has become even more important in recent years as more natural gas has been found in remote locations, where gas pipelines cannot be economically justified. A significant portion of the world reserves of natural gas occurs in such remote regions. Liquefied natural gas (LNG) and methanol projects have long attracted attention by making possible the conversion of natural gas to a liquid which could facilitate transportation and disposal for on-site demand. In recent years methods based upon Fisher-Tropsch (F-T) technology have attracted more attention. In this technology, natural gas is first converted to "syngas," which is a mixture of carbon monoxide and hydrogen, and the syngas is then converted to liquid paraffinic and olefinic hydrocarbons of varying chain lengths. However, the F-T process is a highly energy demanded one as syngas processing step is mostly carried out using steam reforming where large amount of $CO_2$ is produced alongside and to the further isodewaxing step to convert the linear and saturated waxy products into isomers with higher pour-point to cope with the downstream demand.

Prevalent methods of converting hydrocarbon containing gases to ethylene, acetylene, or syngas involve oxidative coupling or partial oxidation. Each method has its own benefits and its own challenges. Oxidative coupling is a technique wherein a lighter hydrocarbon is passed through a reaction bed containing a catalyst that initiates partial oxidation of the hydrocarbon. The primary advantage of oxidative coupling is that relatively mild conditions of temperature and pressure are required. One disadvantage is the difficulty to deal with the in-situ generated temperature gradient resulting from a significant exotherm. Another distinguishing disadvantage of oxidative coupling is the necessity for a solid phase catalyst, which has a short useful life and must be regenerated often. In addition, $CO_2$ is generally formed through uncontrolled side reactions of the intermediate products which are less stable than the methane feed stock and also due to the exothermic character of the reaction. Non-catalytic partial oxidation is also widely practiced because the technique is simpler as there is no catalyst to regenerate. Products generally include gas phase components, which will generally include ethylene, carbon monoxide, carbon dioxide, and acetylene. However, the same drawbacks are the formation of CO and $CO_2$ through side reactions with the $C_{1+}$ intermediate products.

In certain of the above existing processes for converting natural gas into hydrogen and valued chemicals including unsaturated hydrocarbons, oxidants (e.g. $O_2$, $H_2O$, $CO_2$ or $X_2$) are often required to facilitate its conversion into value-added products. Moreover, despite the presence of a catalyst, in certain processes, undesired by-products are still present which are resulting from over-oxidation of intermediate products that are less stable than methane, or coke formation. Hence, the existing processes suffer from several drawbacks, including a considerable formation of heavy aromatics and carbonaceous species which cause rapid catalyst deactivation, and which decrease the process carbon footprint. Also such processes provide limited recycling possibilities of the used catalyst, and include the need for regular reactor recharging. In addition, some metal catalysts cannot be landfilled and call for additional recycling which contributes to the cost incentive.

It is an aim of the present invention to provide a more sustainable process for converting saturated hydrocarbons into useful chemicals and hydrogen, which overcomes at least some of the above-mentioned drawbacks of prior art processes. It is also an aim of the present invention to provide an improved process for converting saturated $C_x$ hydrocarbons (e.g. saturated $C_{1+}$ hydrocarbons) into unsaturated hydrocarbons with a $C_{x+1}$ in carbon number (e.g. unsaturated $C_{2+}$ hydrocarbons), and hydrogen It is in particular an object of the present invention to provide a process for the non-oxidative conversion of saturated $C_{1+}$ hydrocarbons into $C_{2+}$ hydrocarbons and hydrogen which overcomes at least some of the drawbacks of prior art processes.

It is in particular also object of the present invention to provide a process for the non-oxidative conversion of saturated $C_{1+}$ hydrocarbons, such as saturated $C_1$-$C_4$ hydrocarbons, and in particular $C_1$-$C_4$ alkanes such as methane and ethane, into unsaturated hydrocarbons having two or more carbon atoms, such as ethylene and/or acetylene, and hydrogen which overcomes at least some of the drawbacks of prior art processes.

SUMMARY OF THE INVENTION

It has now been found that the above objectives can be attained either individually or in any combination by using the specific and well-defined process as disclosed herein for catalytic hydrocarbon conversion under non-oxidative conditions.

The present invention relates to a process for the conversion of saturated $C_{1+}$ hydrocarbons under non-oxidative conditions into hydrogen and selective unsaturated $C_{2+}$ hydrocarbons in the presence of a catalyst, wherein the catalyst is an unsupported carbon-based catalyst as defined herein.

The Applicants have developed a catalytic process for the conversion of saturated $C_{1+}$ hydrocarbons under non-oxidative conditions into hydrogen and selective unsaturated $C_{2+}$ hydrocarbons. A process according to the invention is in particular based on the use of induction heating for providing the reaction heat necessary for carrying out the process, and makes use of a well-defined carbon-based catalyst.

The present invention provides a process for the non-oxidative conversion of saturated $C_{1+}$ hydrocarbons into unsaturated $C_{2+}$ hydrocarbons and hydrogen in the presence of at least one carbon-based catalyst, wherein the process comprises the steps of:

a) supplying said carbon-based catalyst to a reaction zone;

b) heating the reaction zone containing said carbon-based catalyst to a reaction temperature of at least 350° C. by heating said carbon-based catalyst contained in said reaction zone by induction heating;

c) supplying a reaction gas comprising saturated $C_{1+}$ hydrocarbons to said heated reaction zone comprising said carbon-based catalyst; and d) subjecting said reaction gas to a non-oxidative conversion in the presence of said carbon-based catalyst in said heated reaction zone thereby converting at least a portion of said saturated $C_{1+}$ hydrocarbons into unsaturated $C_{2+}$ hydrocarbons and hydrogen.

The present invention also provides a process for the non-oxidative conversion of saturated $C_{1+}$ hydrocarbons into unsaturated $C_{2+}$ hydrocarbons and hydrogen a process in the presence of an unsupported carbon-based catalyst having a carbon content of at least 90.0 wt % and a metal concentration which is less than 0.3 wt %; with wt % expressed based on the total weight of said carbon-based catalyst, Wherein the Process Comprises the Steps of:

a) supplying said carbon-based catalyst to a reaction zone, b) directly heating of said carbon-based catalyst contained in said reaction zone by means of induction heating thereby indirectly heating the reaction zone containing said carbon-based catalyst to a reaction temperature of at least 350° C.;

c) supplying a reaction gas comprising saturated $C_{1+}$ hydrocarbons to said heated reaction zone comprising said carbon-based catalyst; and d) subjecting said reaction gas to a non-oxidative conversion in the presence of said carbon-based catalyst in said heated reaction zone thereby converting at least a portion of said saturated $C_{1+}$ hydrocarbons into unsaturated $C_{2+}$ hydrocarbons and hydrogen.

In preferred embodiments of the present process said carbon-based catalyst comprises at least 92.0 wt %, more preferably at least 95.0 wt %, more preferably at least 96.0 wt %, more preferably at least 97.0 wt %, more preferably at least 98.0 wt %, more preferably at least 99.0 wt %, more preferably at least 99.5 wt %, more preferably at least 99.9 wt %, of carbon, based on the total weight of said carbon-based catalyst.

In preferred embodiments of the present process said carbon-based catalyst comprises less than 10.0 wt %, preferably less than 5.0 wt % of inorganic oxide(s), preferably less than 3.0 wt % of inorganic oxide(s), based on the total weight of the carbon-based catalyst.

In preferred embodiments of the present process said carbon-based catalyst has a metal concentration which is less than 0.2 wt %, or less than 0.1 wt %, or less than 0.05 wt %, or less than 0.03 wt %, or less than 0.01 wt %, or less than 0.005 wt %, based on the total weight of the carbon-based catalyst.

In Preferred Embodiments of the Present Process Said Carbon-Based Catalyst Consists of, (i) at least 95.0 wt %, preferably at least 97.0 wt %, more preferably at least 99.0 wt %, most preferably at least 99.5 wt % of carbon; with wt % based on the total weight of the carbon-based catalyst;

(ii) from 0 to 5.0 wt %, preferably from 0 to 1.0 wt %, more preferably from 0 to 0.5 wt %, most preferably from 0 to 0.1 wt % of inorganic oxide(s); with wt % based on the total weight of the carbon-based catalyst; and (iii) from 0 to 0.3 wt %, preferably from 0 to 0.1 wt %, more preferably from 0 to 0.01 wt %, most preferably from 0 to 0.001 wt % of metal, with wt % based on the total weight of the carbon-based catalyst.

In certain preferred embodiments of the present process said carbon-based catalyst is metal-free.

In certain preferred embodiments of the present process said carbon-based catalyst consists of carbon. Optionally, a process for the non-oxidative conversion of saturated $C_{1+}$ hydrocarbons of the invention may comprise the further step e) of recovering at least a portion of the carbon-based catalyst from said reaction zone after step d), thereby obtaining a graphite derivative.

The present invention also provides a process for producing a graphite derivative comprising the steps of:

a) supplying a carbon-based catalyst, preferably a carbon-based catalyst as described herein, to a reaction zone;

b) supplying a reaction gas comprising saturated $C_{1+}$ hydrocarbons to said reaction zone comprising said carbon-based catalyst;

c) heating the reaction zone containing said carbon-based catalyst to an effective reaction temperature, and preferably directly heating of said carbon-based catalyst contained in said reaction zone by means of induction heating thereby indirectly heating the reaction zone containing said carbon-based catalyst to a reaction temperature of at least 350° C.;

d) subjecting said reaction gas to a non-oxidative conversion in the presence of said carbon-based catalyst in said heated reaction zone thereby converting at least a portion of said saturated $C_{1+}$ hydrocarbons into unsaturated $C_{2+}$ hydrocarbons, and hydrogen, and thereby depositing carbonaceous material on said carbon-based catalyst; and e) recovering at least a portion of said carbon-based catalyst having carbonaceous material deposited thereon from said reaction zone thereby obtaining said graphite derivative.

In certain embodiments, the present processes thus further comprise the steps of recovering at least a portion of the carbon-based catalyst from said reaction zone after step d) thereby obtaining a graphite derivative. In accordance with the present invention, processes as described herein will involve the direct heating of the reaction zone, by heating a carbon-based catalyst, contained within this reaction zone, by means of induction heating. Thus, processes of the invention comprise heating of the interior of a reaction zone containing a carbon-based catalyst as defined herein to an effective reaction temperature by means of a heat susceptor, or heat receiver, located within said reaction zone, i.e. a carbon-based catalyst as defined herein. The induction heat is directly targeted to the (solid) carbon-based catalyst. This contributes to a reduction of the heat input for the overall process, as compared to processes operated with gas-fired furnace wherein heat loss through stepwise transfer is relatively high.

In certain embodiments of the present process, the carbon-based catalyst is heated by generating an alternating electromagnetic field within the reaction zone containing said carbon-based catalyst upon energization by a power source supplying alternating current, where the alternating electromagnetic field passes through the reaction zone thereby generating an electric current in said carbon-based catalyst and heating the carbon-based catalyst.

The present invention involves heating by means of induction heating. Such heating may for instance be obtained by using an external heat source providing alternating current which is connected to an induction heating device (e.g. an induction heating coil) so as to create a region of high intensity alternating magnetic field throughout the reaction zone, thereby directly heating the catalyst.

Moreover, the present process involves a reaction with external heat input applied directly to the catalyst itself and not by an indirect means external to the actual catalytic material. The present invention thus involves the direct heating of the carbon-based catalyst applied in the present process, rather than heating the reactor wall in which the catalyst (or catalyst bed) is contained. Because the catalyst is directly heated, the chemical reaction, which the catalyst promotes, proceeds more uniformly and efficiently; moreover, it does so without it being necessary to provide as much total heat to the reaction. The present invention clearly differs from the prior art systems and processes in which the walls of the reaction vessel are heated by conventional heating or other heating means, and the heat of the reaction vessel is transmitted to the reactants in the reactor and the catalyst by conduction and/or radiation.

The Applicants have shown that in accordance with processes of the invention, it is possible to use induction heating to carry out hydrocarbon conversion reactions as disclosed herein, which are usually performed at high pressure and/or high temperature, under much milder conditions of mean temperature and pressure. Moreover, the combination of this heating technology with the use of a carbon-based catalyst as defined herein, and susceptible to be heated up under induction, as defined herein, is particularly beneficial, as it allows to carry out non-oxidative conversion processes of hydrocarbons to selectively generate desired reaction products, e.g. selected unsaturated $C_2$+ hydrocarbons such as alkenes (e.g. ethylene), alkynes (e.g. acetylene), and/or aromatics, and to co-produce hydrogen in an efficient and highly selective way. Processes of the invention further advantageously permits to use diverse hydrocarbon sources, e.g. mono-component gasses, as well as gas mixtures such as fossil natural gas and/or renewable sources of natural gas.

Existing processes that involve a catalytic non-oxidative production of unsaturated $C_2$+ hydrocarbons, e.g. ethylene and/or acetylene, from saturated hydrocarbons, such as e.g. methane, with the co-production of hydrogen are typically catalysed by metal-based catalysts supported on a crystalline support, e.g. Mo or Fe on MFI or MWW-zeolite. Due to the high thermodynamic stability of hydrocarbons, severe reaction conditions including high temperatures are required to ensure obtaining an attractive product yield in these prior art processes. Due to a lower stability of the generated products, significant amounts of heavy aromatics and carbonaceous species (also called "coke") are thereby co-formed. Such carbonaceous materials are deposited on the catalyst and cause its deactivation in a relatively fast way. Therefore, these prior art conversion processes require catalyst regeneration since catalyst activity reduces due to blocking of active sites by coke deposition. Consequently, periodic removal of the carbonaceous deposits may be required in these prior art processes. But such catalyst regeneration processes often involve a need to combust the spent catalyst, typically at high temperatures, to remove the coke produced, resulting in $CO/CO_2$ emissions that are undesired for both economic and environmental reasons. Such highly exothermic procedure also adversely and irreversibly impacts the catalyst by reducing the number of active sites. Moreover, currently available catalysts and/or reaction methods for non-oxidative hydrocarbon conversion have a number of drawbacks, such as expense, environmental incompatibility, difficulty in separation from the reaction product, complex reaction conditions, lack of selectivity, poor conversion rates, etc.

The present invention now advantageously provides a solution to at least some of these problems and brings several advantages in terms of process intensification, energy efficiency, product selectively, reactor setup simplification, and safety. By using inductive heating technology, processes as provided herein may advantageously be carried out at reaction temperatures which are distinctly lower than what is used in traditional hydrocarbon conversion processes, such as steam cracking processes as described herein above, while remaining highly effective. Induction heating technology applied in the present processes permits direct and local heat transfer to the carbon-based catalyst material: by generating an alternating electromagnetic field within the reaction zone containing said carbon-based catalyst, an electric current is generated directly in the carbon-based catalyst, which is thereby locally heated. The generated heat is therefore locally generated and used in hydrocarbon conversion; and generation of undesired $CO/CO_2$ emissions is greatly minimized. Advantageously, using a technology based on electric heating, as provided herein, allows the carbon footprint of e processes as described herein to be reduced, e.g., as compared to heating based on gas-fired furnaces.

In addition, the Applicants have shown that a carbon-based catalyst as defined herein, is highly active in the present processes at the applied reaction conditions (including induction heating), shows high catalyst stability, and retains significant catalyst activity despite the formation (and deposition) of carbonaceous materials (coke) on the catalyst during the hydrocarbon conversion reaction. It is further remarkable that such effects are observed when using a carbon-based catalyst as defined herein, and which has a metal concentration as defined herein, or which is even free of any metal.

Moreover, a carbon-based conversion reaction as described herein shows outstanding selectivity towards certain classes of $C_2$+ hydrocarbons, e.g. towards olefins such as ethylene, high stability (low deactivation) and the possibility to work under non-oxidative conditions. The present processes allow for a more efficient catalyst use at relative low reaction temperatures with low carbon footprint, high selectivity towards (light) unsaturated compounds and low catalyst deactivation rates, as compared to the state-of-the-art metal-based catalysts.

In certain embodiments, processes according to the invention further comprise the step of using at least a portion of the recovered graphite derivative as a carbon-based catalyst. In preferred embodiments, processes according to the invention comprise the step of using recovered graphite derivative as a carbon-based catalyst without prior treatment, i.e. without treatment to remove the deposited carbonaceous materials. Thus, a graphite derivative recovered in step e) of a process as disclosed herein, can immediately be used as a carbon-based catalyst in a non-oxidative process as provided herein without treatment of the carbon-based catalyst after recovery, such as a chemical and/or thermal pre-treatment, prior to its use. In some preferred embodiments, processes of the invention may further comprise the step of supplying at least a portion of a graphite derivative recovered in step e) of a process as defined herein, as a carbon-based catalyst in step a) of a process as disclosed herein.

In certain embodiments, processes according to the invention may further comprise the step of processing at least a portion of the recovered graphite derivative into graphite. Hence, the present invention also advantageously allows to exploit carbonaceous species which are undesired by-products generated during the non-oxidative conversion processes of saturated hydrocarbons as a source of graphite. An advantage of the present invention is that it provides a way to obtain a graphite derivative, starting from "wastes" containing carbonaceous materials, i.e. here from a side-product in a non-oxidative hydrogenation process as defined herein.

In another aspect, the invention relates to a graphite derivative obtained or obtainable by a process according to the invention.

In another aspect, the present invention also relates to the use of a graphite derivative as defined herein, or obtained by a process as defined herein, for preparing graphite.

In another aspect, the present invention also relates to the use of a graphite derivative as defined herein, or obtained by a process as defined herein, as a carbon-based catalyst. In preferred embodiments, the invention relates to the use of a graphite derivative as defined herein, or obtained by a process as defined herein, as a carbon-based catalyst in a non-oxidative hydrocarbon conversion process, preferably in a non-oxidative hydrocarbon conversion process for converting saturated $C_{1+}$ hydrocarbons into unsaturated $C_{2+}$ hydrocarbons and hydrogen.

In another aspect, the present invention provides a system for a non-oxidative conversion reaction of saturated $C_{1+}$ hydrocarbons into unsaturated $C_{2+}$ hydrocarbons and hydrogen. In particular, such system comprises:

at least one reaction zone configured to receive a carbon-based catalyst, at least one inlet line for feeding a reaction gas comprising saturated $C_{1+}$ hydrocarbons into said reaction zone;

at least one flow controlling means for controlling reaction gas flow rate to the reaction zone;

at least one outlet line for recovering a reacted product stream comprising unsaturated $C_{2+}$ hydrocarbons and hydrogen from said reaction zone, and at least one induction heating device configured for inductively heating a carbon-based catalyst contained within a reaction zone to a reaction temperature effective for the non-oxidative conversion of saturated $C_{1+}$ hydrocarbons into unsaturated $C_{2+}$ hydrocarbons and hydrogen in the presence of said carbon-based catalyst; and at least one temperature setting device, such as an optical laser pyrometer, for regulating the set temperature of the reaction;

optionally, at least one temperature measuring device for determining the reaction temperature, and optionally, at least one heating device for pre-heating the reaction gas before entering said reaction zone; and optionally, at least one recovery unit for recovering at least a portion of the carbon-based catalyst spent during said non-oxidative conversion from said reaction zone.

The Present Invention Also Provides a System for Producing a Graphite Derivative, Wherein the System Comprises:

at least one reaction zone configured to receive a carbon-based catalyst (as defined herein), at least one inlet line for feeding a reaction gas (as defined herein) comprising saturated $C_{1+}$ hydrocarbons into said reaction zone;

at least one flow controlling means for controlling reaction gas flow rate to the reaction zone;

at least one outlet line for recovering a reacted product stream comprising unsaturated $C_{2+}$ hydrocarbons and hydrogen from said reaction zone, and at least one induction heating device configured for inductively heating a carbon-based catalyst contained within a reaction zone to a reaction temperature effective for the non-oxidative conversion of saturated $C_{1+}$ hydrocarbons into unsaturated $C_{2+}$ hydrocarbons and hydrogen in the presence of said carbon-based catalyst;

at least one temperature setting device for regulating the set temperature of the reaction;

optionally, at least one temperature measuring device for determining the reaction temperature, and optionally, at least one heating device for pre-heating the reaction gas before entering said reaction zone;

optionally at least one recovery unit for recovering at least a portion of the carbon-based catalyst spent during said non-oxidative conversion from said reaction zone.

The independent and dependent claims set out particular and preferred features of the invention. Features from the dependent claims may be combined with features of the independent or other dependent claims as appropriate.

The present invention will now be further described. In the following paragraphs, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

BRIEF DESCRIPTION OF THE FIGURES

FIG. 3 represents catalytic performance of a graphite felt (GF) catalyst as applied during methane conversion in accordance with example 1, wherein FIG. 3A represents product yield, FIG. 3B represents product selectivity, FIG. 3C represents carbon balance and hydrogen yield and FIG. 3D represents power supplied by induction heating device with time on stream on graphite felt. Conditions were as follows: Induction heating, temperatures of 700 and 750° C., $CH_4/Ar=1:1$, 0.1 MPa and 0.37 g GF.

FIG. 7 represents catalytic performance of a graphite felt (GF) catalyst as applied during methane conversion in accordance with example 4, wherein FIG. 7A represents product yield, FIG. 7B represents product selectivity, FIG. 7C represents carbon balance and hydrogen yield and FIG. 7D represents power supplied by induction heating device with time on stream on graphite felt. Conditions were as follows: Induction heating, 700° C., $CH_4/Ar=1:1$, 0.1 MPa, 25 mL/min, 0.37 g GF and $WHSV=1.5$ $h^{-1}$.

FIG. 8 represents catalytic performance of a graphite felt (GF) catalyst as applied during methane conversion in accordance with example 5, wherein FIG. 8A represents product yield, FIG. 8B represents product selectivity, FIG. 8C represents carbon balance and hydrogen yield. Conditions were as follows: Induction heating, 700° C., pure $CH_4$, 0.1 MPa, 20 mL/min, 0.65 g GF and $WHSV=1.3$ $h^{-1}$.

FIG. 9 represents catalytic performance of a catalyst consisting of two layers of graphite felt (2*GF) as applied during methane conversion in accordance with example 6, wherein FIG. 9A represents product yield, FIG. 9B represents product selectivity, FIG. 9C represents carbon balance and hydrogen yield and FIG. 9D represents power supplied by induction heating device with time on stream on 2 layers of graphite felt the catalyst. Conditions were as follows: Induction heating, 700° C., $CH_4/Ar=1:1$, 0.1 MPa, 50 mL/min, 0.74 g of 2*GF and $WHSV=1.5$ $h^{-1}$.

FIG. 10 represents catalytic performance of a catalyst consisting of a graphite felt 2 (GF2) applied during methane conversion in accordance with example 7, wherein FIG. 10A represents product yield, FIG. 10B represents product selectivity, FIG. 10C represents carbon balance and hydrogen yield and FIG. 10D represents power supplied by induction heating device with time on stream on a new graphite felt 2 catalyst. Conditions: Induction heating, 700° C., $CH_4/Ar=1:1$, 0.1 MPa, 25 mL/min, 0.32 g GF2 and WHSV=1.7 $h^{-1}$.

FIG. 12 represents catalytic performance of a catalyst consisting of a carbon nanofiber/graphite felt composite applied during methane conversion in accordance with example 8, wherein FIG. 12A represents product yield, FIG. 12B represents product selectivity, FIG. 12C represents carbon balance and hydrogen yield and FIG. 12D represents power supplied by induction heating device with time on stream on carbon nanofiber/graphite felt. Conditions were as follows: Induction heating, 700° C., $CH_4/Ar=1:1$, 0.1 MPa, 25 mL/min, 0.89 g CNF/GF and WHSV=0.6 $h^{-1}$.

FIG. 14 represents catalytic performance of a catalyst consisting of a natural graphite (G) used during methane conversion in accordance with example 9, wherein FIG. 14A represents product yield, FIG. 14B represents product selectivity, FIG. 14C represents carbon balance and hydrogen yield and FIG. 14D represents power supplied by induction heating device with time on stream on graphite. Conditions were as follows: Induction heating, 700° C., $CH_4/Ar=1:1$, 0.1 MPa, 25 mL/min, 2.16 g and WHSV=0.3 $h^{-1}$.

FIG. 16 represents catalytic performance of an expanded graphite (EG) catalyst as applied during methane conversion in accordance with example 10, wherein FIG. 16A represents product yield, FIG. 16B represents product selectivity, FIG. 16C represents carbon balance and hydrogen yield and FIG. 16D represents power supplied by induction heating device with time on stream on expanded graphite. Conditions were as follows: Induction heating, temperatures of 700 and 750° C. and 650° C., $CH_4/Ar=1:1$, 0.1 MPa, 25 mL/min, 0.12 g EG and WHSV=4.6 $h^{-1}$ FIG. 17 represents catalytic performance of different carbon-based catalysts, i.e. graphite felt (GF), GF2 (denoted "new GF" in the figure), CNF/GF, graphite (G) and expanded graphite (EG), as applied during methane conversion in accordance with example 11, wherein FIG. 17A represents methane conversion, FIG. 17B-E represent product yield of respectively ethylene and acetylene; benzene; toluene; and naphthalene, and FIG. 17F represents hydrogen yield. Conditions were as follows: Induction heating, 700° C., $CH_4/Ar=1:1$, 0.1 MPa, 25 mL/min, 0.37 g GF (WHSV=1.5 $h^{-1}$), 0.32 g GF2 (WHSV=1.7 $h^{-1}$), 0.89 g CNF/GF (WHSV=0.6 $h^{-1}$), 2.16 g (WHSV=0.3 $h^{-1}$) and 0.12 g EG (WHSV=4.6 $h^{-1}$).

FIG. 18 represents catalytic performance of different carbon-based catalysts, i.e. graphite felt (GF), GF2 (denoted "new GF" in the figure), CNF/GF, graphite (G) and expanded graphite (EG), as applied during methane conversion in accordance with example 11, wherein FIG. 18A represents carbon balance and FIG. 18B represents power supplied by an induction heating device with time on stream on the tested catalysts. Conditions were as follows: Induction heating, 700° C., $CH_4/Ar=1:1$, 0.1 MPa, 25 mL/min, 0.37 g GF (WHSV=1.5 $h^{-1}$), 0.32 g GF2 (WHSV=1.7 $h^{-1}$), 0.89 g CNF/GF (WHSV=0.6 $h^{-1}$), 2.16 g (WHSV=0.3 $h^{-1}$) and 0.12 g EG (WHSV=4.6 $h^{-1}$).

FIG. 20 represents catalytic performance of the graphite derivative (spent GF catalyst) as applied during methane conversion in accordance with example 12, wherein FIG. 20A represents methane conversion FIG. 20B represents product selectivity, FIG. 20C represents carbon balance and hydrogen yield and FIG. 20D represents power supplied by induction heating device with time on stream on spent graphite felt. Conditions were as follows: Induction heating, 700° C., $CH_4/Ar=1:1$, 0.1 MPa, 25 mL/min, 0.4 g spent GF and WHSV=1.3 $h^{-1}$.

FIG. 22 represents catalytic performance of a graphite felt (GF) catalyst as applied during methane conversion in accordance with example 13 using induction heating followed by conventional ("classical") heating to carry out the reaction.

DETAILED DESCRIPTION OF THE INVENTION

Figure 1:
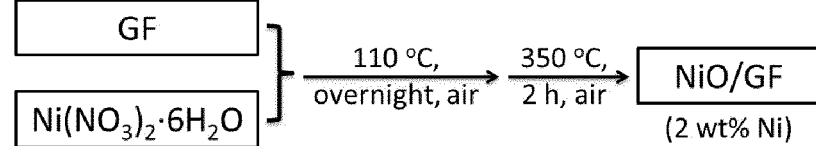
FIG. 1 is a schematic representation of a process for the preparation of a CNF/GF carbon-based catalyst.
Figure 1:
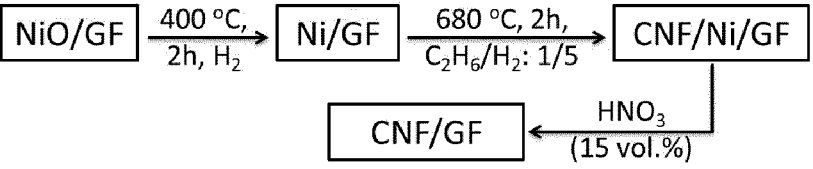

When describing the invention, the terms used are to be construed in accordance with the following definitions, unless a context dictates otherwise.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art.

The terms "comprising", "comprises" and "comprised of" as used herein are synonymous with "including", "includes" or "containing", "contains", and are inclusive or open-ended and do not exclude additional, non-recited members, elements, or method steps. It will be appreciated that the terms "comprising", "comprises" and "comprised of" as used herein comprise the terms "consisting of", "consists" and "consists of".

As used in the specification and the appended claims, the singular forms "a", "an," and "the" include plural referents unless the context clearly dictates otherwise. By way of example, "a step" means one step or more than one step.

Unless defined otherwise, all technical and scientific terms used herein have the same meaning as is commonly understood by one of skill in the art.

The recitation of numerical ranges by endpoints includes all integer numbers and, where appropriate, fractions subsumed within that range (e.g. 1 to 5 can include 1, 2, 3, 4 when referring to, for example, a number of elements, and can also include 1.5, 2, 2.75 and 3.80, when referring to, for example, measurements). The recitation of endpoints also includes the end point values themselves (e.g. from 1.0 to 5.0 includes both 1.0 and 5.0). Any numerical range recited herein is intended to include all sub-ranges subsumed therein.

The term "about" as used herein when referring to a measurable value such as a parameter, an amount, a temporal duration, and the like, is meant to encompass variations of +/−10% or less, preferably +/−5% or less, more preferably +/−1% or less, of and from the specified value, insofar such variations are appropriate to perform in the disclosed invention. It is to be understood that the value to which the modifier "about" refers is itself also specifically, and preferably, disclosed.

The terms "wt %", "vol %", or "mol %" refers to a weight percentage of a component, a volume percentage of a component, or molar percentage of a component, respectively, based on the total weight, the total volume of material, or total moles, that includes the component.

When describing the present invention, the terms used are to be construed in accordance with the following definitions, unless a context dictates otherwise.

Preferred statements (features) and embodiments and uses of this invention are set herein below. Each statement and embodiment of the invention so defined may be combined with any other statement and/or embodiment unless clearly indicated to the contrary. In particular, any feature indicated as being preferred or advantageous may be combined with any other feature or features or statements indicated as being preferred or advantageous. Hereto, the present invention is in particular captured by any one or any combination of one or more of the below numbered statements and embodiments, with any other aspect and/or embodiment.

1. A process for the non-oxidative conversion of saturated $C_{1+}$ hydrocarbons into unsaturated $C_{2+}$ hydrocarbons and hydrogen in the presence of at least one carbon-based catalyst, wherein the process comprises the steps of:
   a) supplying said carbon-based catalyst to a reaction zone;
   b) heating the reaction zone containing said carbon-based catalyst to a reaction temperature of at least 350° C. by heating said carbon-based catalyst contained in said reaction zone by induction heating;
   c) supplying a reaction gas comprising saturated $C_{1+}$ hydrocarbons to said heated reaction zone comprising said carbon-based catalyst; and
   d) subjecting said reaction gas to a non-oxidative conversion in the presence of said carbon-based catalyst in said heated reaction zone thereby converting at least a portion of said saturated $C_{1+}$ hydrocarbons into unsaturated $C_{2+}$ hydrocarbons and hydrogen; and
   e) optionally recovering at least a portion of the carbon-based catalyst from said reaction zone after step d), thereby obtaining a graphite derivative.

2. A process for the non-oxidative conversion of saturated $C_{1+}$ hydrocarbons into unsaturated $C_{2+}$ hydrocarbons and hydrogen in the presence of an unsupported carbon-based catalyst, preferably having a carbon content of at least 90.0 wt %, and preferably having a metal concentration which is less than 0.3 wt %; with wt % expressed. based on the total weight of said carbon-based catalyst,
   wherein the process comprises the steps of:
   a) supplying said carbon-based catalyst to a reaction zone,
   b) directly heating of said carbon-based catalyst contained in said reaction zone by means of induction heating thereby indirectly heating the reaction zone containing said carbon-based catalyst to a reaction temperature of at least 350° C.;
   c) supplying a reaction gas comprising saturated $C_{1+}$ hydrocarbons to said heated reaction zone comprising said carbon-based catalyst; and
   d) subjecting said reaction gas to a non-oxidative conversion in the presence of said carbon-based catalyst in said heated reaction zone thereby converting at least a portion of said saturated $C_{1+}$ hydrocarbons into unsaturated $C_{2+}$ hydrocarbons and hydrogen.

3. A process for producing a graphite derivative comprising the steps of:
   a) supplying a carbon-based catalyst to a reaction zone;
   b) supplying a reaction gas comprising saturated $C_{1+}$ hydrocarbons to said reaction zone comprising said carbon-based catalyst;
   c) heating the reaction zone containing said carbon-based catalyst to an effective reaction temperature; and preferably directly heating of said carbon-based catalyst contained in said reaction zone by means of induction heating thereby indirectly heating the reaction zone containing said carbon-based catalyst to a reaction temperature of at least 350° C.;
   d) subjecting said reaction gas to a non-oxidative conversion in the presence of said carbon-based catalyst in said heated reaction zone thereby converting at least a portion of said saturated $C_{1+}$ hydrocarbons into unsaturated $C_{2+}$ hydrocarbons, and hydrogen, and thereby depositing carbonaceous material on said carbon-based catalyst; and
   e) recovering at least a portion of said carbon-based catalyst having carbonaceous material deposited thereon from said reaction zone thereby obtaining said graphite derivative.

4. A process for producing a graphite derivative comprising the steps of:
   a) supplying a carbon-based catalyst to a reaction zone;
   wherein said carbon-based catalyst is an unsupported carbon-based catalyst preferably having a carbon content of at least 90.0 wt %, and preferably having a metal concentration which is less than 0.3 wt %; with wt % expressed based on the total weight of said carbon-based catalyst, b) supplying a reaction gas comprising saturated $C_{1+}$ hydrocarbons to said reaction zone comprising said carbon-based catalyst;

c) directly heating of said carbon-based catalyst contained in said reaction zone by means of induction heating thereby indirectly heating the reaction zone containing said carbon-based catalyst to an effective reaction temperature; preferably a reaction temperature of at least 350° C.;

d) subjecting said reaction gas to a non-oxidative conversion in the presence of said carbon-based catalyst in said heated reaction zone thereby converting at least a portion of said saturated $C_{1+}$ hydrocarbons into unsaturated $C_{2+}$ hydrocarbons, and hydrogen, and thereby depositing carbonaceous material on said carbon-based catalyst; and e) recovering at least a portion of said carbon-based catalyst having carbonaceous material deposited thereon from said reaction zone thereby obtaining said graphite derivative.

5. Process according to any one of the previous statements wherein said carbon-based catalyst is directly heated by means of induction heating.

6. Process according to any one of the previous statements, wherein said carbon-based catalyst is heated by generating an alternating electromagnetic field within the reaction zone containing said carbon-based catalyst upon energization by a power source supplying alternating current, where the alternating electromagnetic field passes through the reaction zone thereby generating an electric current in said carbon-based catalyst and heating the carbon-based catalyst.

7. Process according to any one of the previous statements, wherein said reaction zone containing said carbon-based catalyst is heated to a reaction temperature of at least 350° C., or at least 400° C., or at least 450°, or at least 500° C., or at least 550° C., or at least 650° C., or at least 700° C., or at least 750° C., or at least 800° C.

8. Process according to any one of the previous statements, wherein said reaction zone containing said carbon-based catalyst is heated to a reaction temperature which is lower than 2000° C., or lower than 1500° C., or lower than 1300° C., or lower than 1100° C.

9. Process according to any one of the previous statements, wherein said non-oxidative hydrocarbon conversion process is carried out at a reaction pressure comprised between 0.1 and 30.0 bar, such as between 0.1 and 20.0 bar, and preferably between 0.1 and 15.0 bar, such as between 0.1 and 10.0 bar or between 0.5 and 5.0 bar.

10. Process according any one of the previous statements, wherein said reaction gas is supplied to said reaction zone at a weight hourly space velocity (WHSV) of between 0.1 and 100 h⁻¹, or between 0.1 and 50 h⁻¹, or between 0.1 and 10 h⁻¹.

11. Process according to any one of the previous statements, wherein said carbon-based catalyst comprises less than 10.0 wt %, based on the total weight of the carbon-based catalyst, of inorganic oxide(s), preferably less than 5.0 wt %, preferably less than 3.0 wt %, preferably less than 1.0 wt %, more preferably less than 0.1 wt % of inorganic oxide(s).

12. Process according to any one of the previous statements, wherein said carbon-based catalyst comprises at least 92.0 wt %, more preferably at least 95.0 wt %, more preferably at least 96.0 wt %, more preferably at least 97.0 wt %, more preferably at least 98.0 wt %, more preferably at least 99.0 wt %, more preferably at least 99.5 wt %, more preferably at least 99.9 wt %, of carbon, based on the total weight of said carbon-based catalyst.

13. Process according to any one of the previous statements, wherein said carbon-based catalyst has a carbon content of at least 80.0 mol %, at least 85.0 mol %, at least 90.0 mol %, or at least 95.0 mol %, at least 97.0 mol %, at least 98.0 mol %, or at least 99.0 mol %, or at least 99.5 mol %, or at least 99.9 mol % of carbon.

14. Process according to any one of the previous statements, wherein said carbon-based catalyst has a metal concentration which is less than 3000 ppm, or less than 2000 ppm, or less than 1000 ppm, or less than 500 ppm, or less than 300 ppm, or less than 100 ppm, or less than 50 ppm based on the total weight of the carbon-based catalyst.

15. Process according to any one of the previous statements, wherein said carbon-based catalyst has a metal concentration which is less than 0.3 wt %, or less than 0.2 wt %, or less than 0.1 wt %, or less than 0.05 wt %, or less than 0.03 wt %, or less than 0.01 wt %, or less than 0.005 wt %, based on the total weight of the carbon-based catalyst.

16. Process according to any one of the previous statements, wherein said carbon-based catalyst consists of (based on the weight of the catalyst):

at least 95.0 wt %, preferably at least 97.0 wt %, more preferably at least 99.0 wt %, most preferably at least 99.5 wt % of carbon; with wt % based on the total weight of the carbon-based catalyst;

from 0 to 5.0 wt %, preferably from 0 to 1.0 wt %, more preferably from 0 to 0.5 wt %, most preferably from 0 to 0.1 wt % of inorganic oxide components; with wt % based on the total weight of the carbon-based catalyst; and from 0 to 0.3 wt %, preferably from 0 to 0.1 wt %, more preferably from 0 to 0.01 wt %, most preferably from 0 to 0.001 wt % of metal, with wt % based on the total weight of the carbon-based catalyst.

17. Process according to any one of the previous statements, wherein said carbon-based catalyst is metal-free.

18. Process according to any one of the previous statements, wherein said carbon-based catalyst consists of carbon.

19. Process according to any one of the previous statements, wherein said carbon-based catalyst is characterised by a Raman spectrum, as determined by Raman Spectroscopy using an excitation wavelength of about 532 nm and exciting laser power of about 100 milliwatt (mW); showing a first peak (D peak) at a wavenumber of about 1350 cm⁻¹ and a second peak (G peak) at a wavenumber from about 1585 to about 1600 cm⁻¹, and wherein said carbon-based catalyst has a Raman coefficient $I_D/I_G$ which is higher than 0.10, such as higher than 0.20 or higher than 0.30, wherein $I_D$ corresponds to the intensity of the Raman spectrum in said D peak; and $I_G$ corresponds to the intensity of the Raman spectrum in said G peak.

20. Process according to any one of the previous statements, wherein said carbon-based catalyst has a BET surface area of at most 500 $m^2/g$, or at most 200 $m^2/g$, or at most 50 $m^2/g$, or at most 20 $m^2/g$, or at most 15 $m^2/g$, or at most 10 $m^2/g$, as determined by ASTM-D-3663 (2020).

21. Process according to any one of the previous statements, wherein said carbon-based catalyst has a BET surface area of at most 5.0 $m^2/g$ as determined by ASTM-D-3663 (2020), and preferably from 0.10 to 5.0 $m^2/g$, or from 0.5 to 3.0 $m^2/g$, or from 1.0 to 5.0 $m^2/g$, or from 1.0 to 3.0 $m^2/g$.

22. Process according to any one of the previous statements, wherein said carbon-based catalyst is non-porous.

23. Process according to any one of the previous statements, wherein said carbon-based catalyst is a non-porous carbon-based catalyst having a BET surface area of at most 5.0 $m^2/g$ as determined by ASTM-D-3663 (2020), and preferably from 0.10 to 5.0 $m^2/g$, or from 0.5 to 3.0 $m^2/g$, or from 1.0 to 5.0 $m^2/g$, or from 1.0 to 3.0 $m^2/g$.

24. Process according to any one of the previous statements, wherein said carbon-based catalyst is a non-porous carbon-based catalyst selected from the group consisting of graphite (G), carbon felt (CF), graphite felt (GF), expanded graphite (EG), graphite fabric, graphite cloth, graphene, and any combinations thereof.

25. Process according to any one of the previous statements, wherein said carbon-based catalyst has an electric resistivity of between $10^{-7}$ and $10^2$ ohm·m at 20° C. as determined by ASTM C611-98(2016).

26. Process according to any one of the previous statements, wherein said reaction gas is supplied to said reaction zone in step c) at a temperature which is lower than the reaction temperature.

27. Process according to any one of the previous statements, wherein said reaction gas is heated prior to being supplied to said reaction zone in step c).

28. Process according to any one of the previous statements, wherein said reaction gas is not heated prior to being supplied to said reaction zone in step c).

29. Process according to any one of the previous statements, wherein said carbon-based catalyst is provided in said reaction zone in a fixed reactor bed.

30. Process according to any one of the previous statements, wherein said carbon-based catalyst is provided in said reaction zone in a moving reactor bed.

31. Process according to any one of the previous statements, wherein said carbon-based catalyst is selected from the group consisting of graphite (G), carbon felt (CF), graphite felt (GF), expanded graphite (EG), graphite fabric, graphite cloth, carbon nanofiber (CNF), carbon nanotubes (CNTs), graphene, few-layer graphene (FLG), and any combinations thereof, and preferably is selected from expanded graphite, graphite felt, carbon nanofiber (CNF), or a combination thereof, and preferably wherein said carbon-based catalyst is a non-porous catalyst selected from the group consisting of graphite (G), carbon felt (CF), graphite felt (GF), expanded graphite (EG), graphite fabric, graphite cloth, graphene, and any combinations thereof.

32. Process according to any one of the previous statements, wherein said carbon-based catalyst is graphite felt.

33. Process according to any one of the previous statements, wherein said saturated $C_{1+}$ hydrocarbons comprise saturated $C_1$-$C_{12}$ hydrocarbons, preferably saturated $C_1$-$C_1$ hydrocarbons, preferably saturated $C_1$-$C_8$ hydrocarbons, preferably saturated $C_1$-$C_6$ hydrocarbons, preferably saturated $C_1$-$C_4$ hydrocarbons, preferably saturated $C_1$-$C_3$ hydrocarbons.

34. Process according to any one of the previous statements, wherein said saturated $C_{1+}$ hydrocarbons comprise saturated hydrocarbons selected from the group consisting of methane, ethane, propane, butane, pentane, cyclopropane, cyclopentane, cyclohexane, and any combinations of two or more thereof.

35. Process according to any one of the previous statements, wherein said saturated $C_{1+}$ hydrocarbons are selected from the group consisting of methane, ethane, propane, or any combinations of two or more thereof.

36. Process according to any one of the previous statements, wherein said saturated $C_{1+}$ hydrocarbons is methane and/or ethane.

37. Process according to any one of the previous statements, wherein said reaction gas comprises at least 50.0 mol % of said saturated $C_{1+}$ hydrocarbons, and preferably at least 75.0 mol %, or preferably at least 90.0 mol %, or preferably at least 95.0 mol %, or preferably at least 99.0 mol % of $C_{1+}$ saturated hydrocarbons.

38. Process according to any one of the previous statements, wherein said reaction gas comprises at least 80.0 mol %, such as at least 85.0 mol %, or at least 90.0 mol % of methane.

39. Process according to any one of the previous statements, wherein said reaction gas comprises:
from 80.0 to 100 mol % of methane, and preferably from 85.0 to 100 mol % of methane,
from 0 to 5.0 mol % of nitrogen, or from 0 to 3.0 mol % of nitrogen; and
from 0 to 20.0 mol % of hydrogen, or from 0 to 10.0 mol % of hydrogen.

40. Process according to any one of the previous statements, wherein said reaction gas comprises:
from 80.0 to 100 mol % of methane, and preferably from 85.0 to 100 mol % of methane,
from 0 to 15.0 mol % of ethane, such as from 0 to 10.0 mol % of ethane, or from 0 to 5.0 mol % of ethane, and
from 0 to 15.0 mol % of propane, such as from 0 to 10.0 mol % of propane, or from 0 to 5.0 mol % of propane, or from 0 to 3.0 mol % of propane, and
from 0 to 5.0 mol %, or from 0 to 3.0 mol % of butane, and
from 0 to 5.0 mol %, or from 0 to 3.0 mol % of pentane, and
from 0 to 5.0 mol % of nitrogen, or from 0 to 3.0 mol % of nitrogen.
from 0 to 20.0 mol % of hydrogen, or from 0 to 10.0 mol % of hydrogen.

41. Process according to any one of the previous statements, wherein said reaction gas comprises at least 80.0 mol %, such as at least 85.0 mol %, or at least 90.0 mol % of ethane.

42. Process according to any one of the previous statements, wherein said reaction gas comprises:
from 80.0 to 100 mol % of ethane, and preferably from 85.0 to 100 mol % of ethane,
from 0 to 5.0 mol % of nitrogen, or from 0 to 3.0 mol % of nitrogen; and
from 0 to 20.0 mol % of hydrogen, or from 0 to 10.0 mol % of hydrogen.

43. Process according to any one of the previous statements, wherein said reaction gas comprises:
from 80.0 to 100 mol % of ethane, and preferably from 85.0 to 100 mol % of ethane,
from 0 to 15.0 mol % of methane, such as from 0 to 10.0 mol % of methane, or from 0 to 5.0 mol % of methane, and
from 0 to 15.0 mol % of propane, such as from 0 to 10.0 mol % of propane, or from 0 to 5.0 mol % of propane, or from 0 to 3.0 mol % of propane, and
from 0 to 5.0 mol %, or from 0 to 3.0 mol % of butane, and
from 0 to 5.0 mol %, or from 0 to 3.0 mol % of pentane, and
from 0 to 5.0 mol % of nitrogen, or from 0 to 3.0 mol % of nitrogen; and
from 0 to 20.0 mol % of hydrogen, or from 0 to 10.0 mol % of hydrogen.

44. Process according to any one of the previous statements, wherein said unsaturated $C_{2+}$ hydrocarbons comprise alkenes, preferably $C_2$-$C_{12}$ alkenes, preferably $C_2$-$C_{10}$ alkenes, preferably $C_2$-$C_8$ alkenes, preferably $C_2$-$C_6$ alkenes, preferably $C_2$-$C_4$ alkenes.

45. Process according to any one of the previous statements, wherein said unsaturated $C_{2+}$ hydrocarbons comprise ethylene.

46. Process according to any one of the previous statements, wherein said unsaturated $C_{2+}$ hydrocarbons comprise alkynes, preferably $C_2$-$C_{12}$ alkynes, preferably $C_2$-$C_{10}$ alkynes, preferably $C_2$-$C_8$ alkynes, preferably $C_2$-$C_6$ alkynes, preferably $C_2$-$C_4$ alkynes.

47. Process according to any one of the previous statements, wherein said unsaturated $C_{2+}$ hydrocarbons comprise acetylene.

48. Process according to any one of the previous statements, wherein said unsaturated $C_{2+}$ hydrocarbons comprise aromatic hydrocarbons, preferably $C_{5+}$ aromatic hydrocarbons, preferably aromatic $C_6$-$C_{12}$ hydrocarbons, and more preferably comprise aromatic hydrocarbons selected from the group consisting of benzene, toluene, naphthalene, and any combinations of two or more thereof.

49. Process according to any one of the previous statements, wherein said unsaturated $C_{2+}$ hydrocarbons comprise:
from 0.5 to 70.0 mol %, or from 0.5 to 50.0 mol %, or from 0.5 to 30.0 mol %, or from 0.5 to 20.0 mol % of alkenes, preferably $C_2$-$C_{12}$ alkenes, preferably $C_2$-$C_1$ alkenes, preferably $C_2$-$C_8$ alkenes, preferably $C_2$-$C_6$ alkenes, preferably $C_2$-$C_4$ alkenes, and preferably ethylene; and
from 0.5 to 70.0. mol % of alkynes, or from 0.5 to 50.0 mol %, or from 0.5 to 30.0 mol %, or from 0.5 to 20.0 mol % of alkynes, and preferably $C_2$-$C_{12}$ alkynes, preferably $C_2$-$C_1$ alkynes, preferably $C_2$-$C_8$ alkynes, preferably $C_2$-$C_6$ alkynes, preferably $C_2$-$C_4$ alkynes, and preferably acetylene, and
optionally from 0 to 50.0 mol %, or from 0 to 25.0 mol %, or from 0 to 10.0 mol % of aromatic hydrocarbons, preferably $C_6+$ aromatic hydrocarbons, preferably aromatic $C_6$-$C_{12}$ hydrocarbons, and more preferably aromatic hydrocarbons selected from the group consisting of benzene, toluene, naphthalene, and any combinations of two or more thereof.

50. Process according to any one of the previous statements, wherein said unsaturated $C_{2+}$ hydrocarbons comprise

20 from 1.0 to 10.0 mol % of ethylene, such as from 1.5 to 9.0 mol % of ethylene, or from 4.5 to 7.5 mol % of ethylene, and
from 1.0 to 10.0 mol % of acetylene, such as from 1.5 to 9.0 mol % of acetylene, or from 4.5 to 7.5 mol % of acetylene, and
from 0 to 4.5 mol % of benzene, such as from 1.0 to 4.0 mol % of benzene, or from 1.5 to 3.6 mol % of benzene, and
from 0 to 1.5 mol % of toluene, such as from 0.1 to 1.3 mol % of toluene, or from 0.3 to 1.2 mol % of toluene, and
from 0 to 3.0 mol % of naphthalene, such as from 0.3 to 2.5 mol % of naphthalene, or from 0.6 to 2.1 mol % of naphthalene.

51. Process according to any one of the previous statements, wherein said reaction gas comprises a natural gas, preferably wherein said natural gas is of fossil origin, of renewable origin or a combination thereof.

52. A process according to any one of the previous statements 1-2, and 5 to 51, for the non-oxidative conversion of methane into unsaturated $C_{2+}$ hydrocarbons and hydrogen in the presence of an unsupported carbon-based catalyst, as defined in any one of the previous statements, wherein the process comprises the steps of:
a) supplying said carbon-based catalyst to a reaction zone;
b) directly heating of said carbon-based catalyst contained in said reaction zone by means of induction heating thereby indirectly heating the reaction zone containing said carbon-based catalyst to a reaction temperature of at least 350° C.;
c) supplying a reaction gas comprising methane to said heated reaction zone comprising said carbon-based catalyst; and
d) subjecting said reaction gas to a non-oxidative conversion in the presence of said carbon-based catalyst in said heated reaction zone thereby converting at least a portion of said methane into unsaturated $C_{2+}$ hydrocarbons and hydrogen; and
e) optionally recovering at least a portion of the carbon-based catalyst from said reaction zone after step d), thereby obtaining a graphite derivative.

53. A process according to any one of statements 1-2, and 5 to 51, for the non-oxidative conversion of ethane into unsaturated $C_{2+}$ hydrocarbons and hydrogen in the presence of an unsupported carbon-based catalyst, as defined in any one of the previous statements, wherein the process comprises the steps of:
a) supplying said carbon-based catalyst to a reaction zone;
b) directly heating of said carbon-based catalyst contained in said reaction zone by means of induction heating thereby indirectly heating the reaction zone containing said carbon-based catalyst to a reaction temperature of at least 350° C.;
c) supplying a reaction gas comprising ethane to said heated reaction zone comprising said carbon-based catalyst; and
d) subjecting said reaction gas to a non-oxidative conversion in the presence of said carbon-based catalyst in said heated reaction zone thereby converting at least a portion of said ethane into unsaturated $C_{2+}$ hydrocarbons and hydrogen; and e) optionally recovering at least a portion of the carbon-based catalyst from said reaction zone after step d), thereby obtaining a graphite derivative.

54. A process according to any one of statements 3 to 52, for producing a graphite derivative comprising the steps of:

a) supplying an unsupported carbon-based catalyst as defined in any one of the previous statements, to a reaction zone;

b) supplying a reaction gas comprising methane to said reaction zone comprising said carbon-based catalyst;

c) directly heating of said carbon-based catalyst contained in said reaction zone by means of induction heating, thereby indirectly heating the reaction zone containing said carbon-based catalyst to an effective reaction temperature;

d) subjecting said reaction gas to a non-oxidative conversion in the presence of said carbon-based catalyst in said heated reaction zone thereby converting at least a portion of said methane into unsaturated $C_{2+}$ hydrocarbons, and hydrogen, and thereby depositing carbonaceous material on said carbon-based catalyst; and e) recovering at least a portion of said carbon-based catalyst having carbonaceous material deposited thereon from said reaction zone thereby obtaining said graphite derivative.

55. A process according to any one of statements 3 to 51 and 53, for producing a graphite derivative comprising the steps of:

a) supplying an unsupported carbon-based catalyst as defined in any one of the previous statements to a reaction zone;

b) supplying a reaction gas comprising ethane to said reaction zone comprising said carbon-based catalyst;

c) directly heating of said carbon-based catalyst contained in said reaction zone by means of induction heating, thereby indirectly heating the reaction zone containing said carbon-based catalyst to an effective reaction temperature;

d) subjecting said reaction gas to a non-oxidative conversion in the presence of said carbon-based catalyst in said heated reaction zone thereby converting at least a portion of said ethane into unsaturated $C_{2+}$ hydrocarbons and hydrogen; and thereby depositing carbonaceous material on said carbon-based catalyst; and e) recovering at least a portion of said carbon-based catalyst having carbonaceous material deposited thereon from said reaction zone thereby obtaining said graphite derivative.

56. A process according to any one of the previous statements, wherein said unsaturated $C_{2+}$ hydrocarbons comprise ethylene and/or acetylene, and optionally aromatic hydrocarbons selected from the group consisting of benzene, toluene, naphthalene, and any combinations of two or more thereof.

57. Process according to any one of the previous statements, wherein said carbon-based catalyst has a fibrous, a spherical or a random morphology.

58. Process according to any one of the previous statements, wherein said carbon-based catalyst has a spherical morphology and has an average particle diameter of at least 0.1 μm, and preferably between 0.1 and 1000 μm; or between 1 and 1000 μm, as determined by SEM microscopy or by sieving according to ASTM D4513-11.

59. Process according to any one of the previous statements, further comprising the step of subjecting the recovered graphite derivate to a mechanical treatment to reduce the size of the said graphite derivative.

60. Process according to any one of the previous statements, further comprising the step of processing at least a portion of the recovered graphite derivative into graphite.

61. Process according to any one of the previous statements, further comprising the step of using at least a portion of the recovered graphite derivative as a carbon-based catalyst.

62. Process according to statement 61, wherein the recovered graphite derivative is used as a carbon-based catalyst without prior treatment to remove carbonaceous material deposited thereon.

63. Process according to any one of statements 61 or 62, comprising the step of using at least a portion of said recovered graphite derivative as a carbon-based catalyst in a hydrocarbon conversion process, preferably in a non-oxidative hydrocarbon conversion process, and more preferably in a non-oxidative hydrocarbon conversion process for converting saturated $C_{1+}$ hydrocarbons into unsaturated $C_{2+}$ hydrocarbons and hydrogen.

64. Process according to any one of the previous statements, comprising the step of supplying the recovered graphite derivative as a carbon-based catalyst in step a) of the process according to any one of statements 1 to 63.

65. Graphite derivative obtained or obtainable by the process of any one of the previous statements.

66. Graphite derivative according to the previous statement, wherein the graphite derivative comprises a carbon-containing material selected from the group consisting of graphite (G), carbon felt (CF), graphite felt (GF), expanded graphite (EG), graphite fabric, graphite cloth, carbon nanofiber (CNF), carbon nanotubes (CNTs), graphene, few-layer graphene (FLG), and any combinations thereof, and preferably is selected from expanded graphite, graphite felt, carbon nanofiber (CNF), or a combination thereof.

67. Graphite derivative according to any one of the previous statements, wherein the graphite derivative has a metal concentration which is less than 3000 ppm, or less than 2000 ppm, or less than 1000 ppm, or less than 500 ppm, or less than 300 ppm, or less than 100 ppm, or less than 50 ppm, based on the total weight of the graphite derivative.

68. Graphite derivative according to any one of the previous statements, wherein the graphite derivative has a metal concentration which is less than 0.3 wt %, or less than 0.2 wt %, or less than 0.1 wt %, or less than 0.05 wt %, or less than 0.03 wt %, or less than 0.01 wt %, or less than 0.005 wt %, based on the total weight of the graphite derivative.

69. Graphite derivative according to any one of the previous statements, wherein the graphite derivative is metal-free.

70. Graphite derivative according to any one of the previous statements, wherein said graphite derivative is characterised by a Raman spectrum, as determined by Raman Spectroscopy using an excitation wavelength of about 532 nm and exciting laser power of about 100 milliwatt (mW); showing a first peak (D peak) at a wavenumber of about 1350 $cm^{-1}$ and a second peak (G peak) at a wavenumber from about 1585 to about 1600 $cm^{-1}$, and wherein said carbon-based catalyst has a Raman coefficient $I_D/I_G$ which is higher than 0.10, or higher than 0.20, or higher than 0.30, wherein $I_D$ corresponds to the intensity of the Raman spectrum in said D peak; and $I_G$ corresponds to the intensity of the Raman spectrum in said G peak.

71. Graphite derivative according to any one of the previous statements, wherein the graphite derivative has a BET surface area of at most 500 $m^2$/g, or at most 200 $m^2$/g, or at most 50 $m^2$/g, or at most 20 $m^2$/g, or at most 15 $m^2$/g, or at most 10 $m^2$/g, as determined by ASTM-D-3663 (2020).

72. Graphite derivative according to any one of the previous statements, wherein the graphite derivative has an electric resistivity of between $10^{-7}$ and $10^2$ ohm·m at 20° C. as determined by ASTM C611-98 (2016).

73. Graphite derivative according to any one of the previous statements, wherein said graphite derivative comprises one or more layers of carbon-containing material, and preferably from 2 to 5 layers of carbon-containing material.

74. Use of a graphite derivative according to any one of the previous statements, or obtained by the process according to any one of the previous statements for preparing graphite.

75. Use of a graphite derivative according to any one of the previous statements, or obtained by the process as defined in any one of the previous statements as a carbon-based catalyst.

76. Use of a graphite derivative according to any one of the previous statements, as a carbon-based catalyst in a non-oxidative hydrocarbon conversion process, preferably in a non-oxidative hydrocarbon conversion process for converting saturated $C_{1+}$ hydrocarbons into unsaturated $C_{2+}$ hydrocarbons and hydrogen.

77. Use of a graphite derivative according to any one of the previous statements, as a carbon-based catalyst in a process as defined in any one of the previous statements.

78. System for a non-oxidative conversion reaction of saturated $C_{1+}$ hydrocarbons into unsaturated $C_{2+}$ hydrocarbons and hydrogen, wherein the system comprises:

at least one reaction zone configured to receive a carbon-based catalyst, at least one inlet line for feeding a reaction gas comprising saturated $C_{1+}$ hydrocarbons into said reaction zone;

at least one flow controlling means for controlling reaction gas flow rate to the reaction zone;

at least one outlet line for recovering a reacted product stream comprising unsaturated $C_{2+}$ hydrocarbons and hydrogen from said reaction zone, and at least one induction heating device configured for inductively heating a carbon-based catalyst contained within a reaction zone to a reaction temperature effective for the non-oxidative conversion of saturated $C_{1+}$ hydrocarbons into unsaturated $C_{2+}$ hydrocarbons and hydrogen in the presence of said carbon-based catalyst;

at least one temperature setting device, such as an optical laser pyrometer, for regulating the set temperature of the reaction;

optionally, at least one temperature measuring device for determining the reaction temperature, and optionally, at least one heating device for pre-heating the reaction gas before entering said reaction zone; and optionally, at least one recovery unit for recovering at least a portion of the carbon-based catalyst spent during said non-oxidative conversion from said reaction zone.

79. System for producing a graphite derivative, wherein the system comprises:

at least one reaction zone configured to receive a carbon-based catalyst (as defined herein), at least one inlet line for feeding a reaction gas (as defined herein) comprising saturated $C_{1+}$ hydrocarbons into said reaction zone;

at least one flow controlling means for controlling reaction gas flow rate to the reaction zone;

at least one outlet line for recovering a reacted product stream comprising unsaturated $C_{2+}$ hydrocarbons and hydrogen from said reaction zone, and at least one induction heating device configured for inductively heating a carbon-based catalyst contained within a reaction zone to a reaction temperature effective for the non-oxidative conversion of saturated $C_{1+}$ hydrocarbons into unsaturated $C_{2+}$ hydrocarbons and hydrogen in the presence of said carbon-based catalyst;

at least one temperature setting device for regulating the set temperature of the reaction;

optionally, at least one temperature measuring device for determining the reaction temperature, and optionally, at least one heating device for pre-heating the reaction gas before entering said reaction zone;

optionally at least one recovery unit for recovering at least a portion of the carbon-based catalyst spent during said non-oxidative conversion from said reaction zone.

80. System according to any one of the previous statements, wherein said induction heating device comprises at least one induction coil defining a space provided within said induction coil capable of receiving said carbon-based catalyst, and an AC power supply electrically connected to said induction coil and capable of supplying an alternating current having a suitable frequency to said induction coil, such as a frequency alternating between 2 and 500 kHz.

81. System according to any one of the previous statements, wherein said reaction zone is a fixed bed reactor.

82. System according to any one of the previous statements, wherein said reaction zone is a moving bed reactor.

83. System according to any one of the previous statements wherein said temperature measuring device comprises a device capable of measuring the reaction temperature within the reaction zone, such as for instance a thermocouple, or a laser pyrometer.

84. System according to any one of the previous statements wherein said temperature measuring device comprises a device capable of measuring the temperature at the outer surface of the reaction zone, such as for instance a laser pyrometer.

In a first aspect, the present invention is directed to a process for the non-oxidative conversion of saturated $C_{1+}$ hydrocarbons into unsaturated hydrocarbons having two or more carbon atoms and hydrogen which takes place in the presence of a specific type of catalyst, i.e. a carbon-based catalyst as defined herein. During such non-oxidative hydrocarbon conversion process certain amounts of carbonaceous materials, e.g. heavy aromatics and carbonaceous species, also known as "coke", are formed, and are deposited on the carbon-catalyst catalyst used in the process. The present invention found a way to effectively perform such hydrocarbon conversion reaction under optimal conditions using induction heating technology for providing the necessary reaction heat. In addition, the present invention found a way to exploit this undesired side-effect of the non-oxidative hydrocarbon conversion process, as it found a way to re-use and hence valorise the undesired "waste-product" formed during such reaction.

A process for the non-oxidative conversion of saturated $C_{1+}$ hydrocarbons into unsaturated $C_{2+}$ hydrocarbons and hydrogen in the presence of at least one carbon-based catalyst according to the invention in particular comprises the steps of:

a) supplying said carbon-based catalyst to a reaction zone;

b) heating the reaction zone containing said carbon-based catalyst to a reaction temperature of at least 350° C., by heating said carbon-based catalyst contained in said reaction zone by induction heating;

c) supplying a reaction gas comprising saturated $C_{1+}$ hydrocarbons to said heated reaction zone comprising said carbon-based catalyst; and d) subjecting said reaction gas to a non-oxidative conversion in the presence of said carbon-based catalyst in said heated reaction zone thereby converting at least a portion of said saturated $C_{1+}$ hydrocarbons into unsaturated $C_{2+}$ hydrocarbons and hydrogen.

It may be noted that the sequence of the steps b) and c) is not meant to be limiting. Step b) and c) may happen simultaneously, or step b) may be initiated before stop c), or step c) may be initiated before step b).

A process for the non-oxidative conversion of saturated $C_{1+}$ hydrocarbons may comprise a further step e) wherein at least a portion of the carbon-based catalyst is recovered from said reaction zone after step d), thereby obtaining a graphite derivative.

The present invention addresses the catalytic conversion of saturated $C_{1+}$ hydrocarbons into hydrogen and unsaturated $C_{2+}$ hydrocarbons, such as e.g. alkenes (olefins), alkynes (acetylenes), and optionally aromatic hydrocarbons; and is in particular directed to a non-oxidative hydrocarbons conversion process which is carried out in the presence of a carbon-based catalyst as defined herein.

The term "hydrocarbon conversion" refers to a change in a molecular structure or composition of a hydrocarbon. In certain instances, the term "hydrocarbon conversion" and "dehydrogenation" are used herein as synonym and intend to refer to a chemical reaction involving removal of hydrogen from an organic molecule. Hydrocarbon conversion in the present invention is in particular non-oxidative. The term "non-oxidative" as used herein is understood to mean that the hydrocarbon conversion proceeds in the absence of an oxidizing agent such as oxygen or sulphur. The term "oxygen" in this context intends to include air, $O_2$, $H_2O$, CO, and $CO_2$.

The reaction conditions applied during a non-oxidative hydrocarbon conversion process in the presence of said carbon-based catalyst cause the deposition of carbonaceous materials on said carbon-based catalyst. The terms "carbonaceous material", "coke" and "carbon deposits" are used herein interchangeably to mean carbon-containing materials, which are essentially non-volatile solids at the reaction conditions, with a low hydrogen content relative to carbon content (such as a H/C molar ratio of less than 0.8; preferably less than 0.5). These may include for instance crystalline graphite, graphitic sheets, graphitic fragments, or other carbon containing structures which are essentially non-volatile solids at the reaction conditions. Carbonaceous materials, as defined herein, in particular include the carbonaceous materials that are adsorbed on the carbon-based catalyst used in the present processes.

In another aspect, the present invention also relates to a process for preparing a graphite derivative. Thereto, the present invention provides a process for producing a graphite derivative comprising the steps of:

a) supplying a carbon-based catalyst to a reaction zone;

b) supplying a reaction gas comprising saturated $C_{1+}$ hydrocarbons to said reaction zone comprising said carbon-based catalyst;

c) heating the reaction zone containing said carbon-based catalyst to an effective reaction temperature;

d) subjecting said reaction gas to a non-oxidative conversion in the presence of said carbon-based catalyst in said heated reaction zone thereby converting at least a portion of said saturated $C_{1+}$ hydrocarbons into unsaturated $C_{2+}$ hydrocarbons, and hydrogen, and thereby depositing carbonaceous material on said carbon-based catalyst; and e) recovering at least a portion of said carbon-based catalyst having carbonaceous material deposited thereon from said reaction zone thereby obtaining said graphite derivative.

It may be noted that the sequence of the steps b) and c) is not meant to be limiting. Step b) and c) may happen simultaneously, or step b) may be initiated before stop c), or step c) may be initiated before step b).

The method for preparing a graphite derivative according to the invention is advantageously integrated in a process for the non-oxidative conversion of hydrocarbons which takes place in the presence of a specific type of catalyst, i.e. a carbon-based catalyst as defined herein.

During such non-oxidative hydrocarbon conversion process certain amounts of carbonaceous materials, e.g. heavy aromatics and carbonaceous species, also known as "coke", are formed, and are deposited on the carbon-catalyst catalyst used in the process. The present invention also found a way to exploit this undesired side-effect of non-oxidative hydrocarbon conversion processes, and found a way to re-use and hence valorise the undesired "waste-product" formed during such reaction.

A process for preparing a graphite derivative according to the invention has the advantage that it permits to use diverse hydrocarbon sources, e.g. fossil natural gas and/or renewable sources of natural gas, to generate graphite derivatives. The present processes allow to produce graphite derivatives that have beneficial characteristics, such as e.g. improved morphology, high electro-resistivity, improved composition, including a higher purity and limited levels of contaminants such as inorganic (e.g. Si, Al) or metallic (e.g. Ni, Mo, etc) contaminants.

A process for making a graphite derivative according to the invention is also characterised by an improved carbon efficiency and high energy efficiency, especially since the graphite derivative can be readily obtained as a side stream in a non-oxidative hydrocarbon conversion processes as defined herein. Graphite derivative preparation according to the invention, and as compared for instance to preparation starting from petroleum coke, results in reduced $CO/CO_2$ emissions and has lower temperature requirements. The present invention allows resource recovery, cyclic utilization and environmental protection in the whole operation of the processes.

Processes as disclosed herein comprise the step of supplying a reaction gas comprising saturated hydrocarbons, having at least one carbon atom, to a reaction zone in which a carbon-based catalyst as defined herein has been supplied. Hence, a reaction gas is brought into contact with a carbon-based catalyst as defined herein to form hydrocarbons having two or more carbon atoms and hydrogen.

The term "reaction gas" as used herein includes a gas comprising or consisting of a saturated hydrocarbon or a mixture of saturated hydrocarbons as defined herein. The term "reacted product" or "reacted product stream" is defined as the stream comprising or consisting of hydrocarbons and optionally unreacted reactants produced after the hydrocarbon conversion reaction.

The term "hydrocarbon" refers to an organic compound consisting of the elements hydrogen and carbon. Hydrocarbons generally fall into two classes: aliphatic, or straight chain hydrocarbons, and cyclic, or closed ring hydrocarbons, including cyclic terpenes. Examples of hydrocarbon-containing materials for use in the present processes include any form of natural gas or oil.

The term "saturated hydrocarbons" refers to hydrocarbons having no carbon-carbon double bonds. In the present invention, the terms "saturated hydrocarbons" and "saturated $C_{1+}$ hydrocarbons" are used herein interchangeably, and these terms refer to saturated hydrocarbons having at least one carbon atom. Saturated hydrocarbons may be linear or cyclic hydrocarbons. Preferred example of saturated $C_{1+}$ hydrocarbons for use in the present invention may be saturated $C_1$-$C_{12}$ hydrocarbons, preferably saturated $C_1$-$C_{10}$ hydrocarbons, preferably saturated $C_1$-$C_8$ hydrocarbons, preferably saturated $C_1$-$C_6$ hydrocarbons, preferably saturated $C_1$, $C_2$, $C_3$, $C_4$, $C_5$, $C_6$ hydrocarbons. When a subscript is used herein following a carbon atom, the subscript refers to the number of carbon atoms that the named group may contain.

In certain preferred embodiments, saturated $C_{1+}$ hydrocarbons in this invention comprise saturated hydrocarbons selected from the group consisting of methane, ethane, propane, butane, pentane, cyclopropane, cyclopentane, cyclohexane, and any combinations of two or more thereof. In certain preferred embodiments, said saturated $C_{1+}$ hydrocarbons are selected from methane, ethane, propane, or any combinations of two or more thereof. In certain preferred embodiments, said saturated $C_{1+}$ hydrocarbons comprise or consist of methane. In certain preferred embodiments, said saturated $C_{1+}$ hydrocarbons comprise or consist of ethane. In certain preferred embodiments, said saturated $C_{1+}$ hydrocarbons comprise or consist of propane. In certain preferred embodiments, said saturated $C_{1+}$ hydrocarbons comprise or consist of butane.

In the present processes, a reaction gas comprising saturated $C_{1+}$ hydrocarbons, as defined hereinabove, is provided to a reaction zone comprising said carbon-based catalyst. The reaction gas comprises at least 50.0 mol % of saturated hydrocarbons, as defined hereinabove, such as at least 75.0 mol %, or at least 80.0 mol %, or at least 90.0 mol %, or at least 95.0 mol %, or at least 99.0 mol % of saturated hydrocarbons, or at least 99.5 mol %, or at least 99.9 mol % of saturated hydrocarbons as defined herein, based on the total reaction gas. For instance, the reaction gas comprises from 50.0 to 100 mol % of saturated hydrocarbons as defined herein, or from 75.0 to 99 mol %, or from 80.0 to 97.0 mol % based on the total reaction gas of saturated $C_{1+}$ hydrocarbons as defined herein. In certain embodiments of a process according to the invention, the applied reaction gas comprises a mixture of different saturated hydrocarbons. For instance, in certain embodiments the applied reaction gas comprises a mixture of methane and ethane, or a mixture of methane and propane, or a mixture of ethane and propane, or a mixture of methane, ethane and propane.

In certain other embodiments of a process according to the invention, the applied reaction gas essentially consists of one saturated hydrocarbon species, e.g. only methane, or only ethane, or only propane, or only butane. The term "essentially consists of" as used in this context indicates that said one saturated hydrocarbon species, e.g. methane, or ethane, or propane, makes up at least 90.0 mol %, such as least 92.0 mol %, or at least 95.0 mol %, or at least 97.0 mol %, or at least 99.0 mol % of the total amount of saturated hydrocarbons in said reaction gas. In other words, in certain preferred embodiments, a reaction gas essentially consisting of one saturated $C_{1+}$ hydrocarbon species, e.g. methane, or ethane, or propane, comprises less than 10 mol %, based on the total amount of saturated hydrocarbons in said reaction gas, of saturated $C_{1+}$ hydrocarbons different from said one hydrocarbon species; such as less than 8.0 mol %, or less than 5.0 mol %, or less than 3.0 mol %, or less than 1.0 mol % of saturated $C_{1+}$ hydrocarbons different from of said one saturated hydrocarbon species.

In certain preferred embodiments, the reaction gas applied a process according to the invention consists of one saturated hydrocarbon species, e.g. only methane, or only ethane, or only propane.

In certain embodiments, said reaction gas comprises at least 80.0 mol %, such as at least 85.0 mol %, or at least 90.0 mol % of methane.

In certain embodiments, said reaction gas comprises at least 80.0 mol %, such as at least 85.0 mol %, or at least 90.0 mol % of ethane.

In certain embodiments, said reaction gas comprises at least 80.0 mol %, such as at least 85.0 mol %, or at least 90.0 mol % of propane.

In certain embodiments, said reaction gas comprises at least 80.0 mol %, such as at least 85.0 mol %, or at least 90.0 mol % of butane.

Optionally, a reaction gas as applied in a process according to the invention may also comprise hydrogen. Preferably, the molar ratio of this optional hydrogen to saturated $C_{1+}$ hydrocarbon in said reaction gas may be in the range from about 1:4 to 0:1.

Optionally, a reaction gas as applied in a process according to the invention may also comprise minor amounts of other components selected from oxygen, nitrogen, or carbon dioxide. Preferably such other component may be present in an amount lower than 2.0 mol %, such as lower than 1.5 mol %, or lower than 1.0 mol % or lower than 0.5 mol %, based on the total reaction gas.

Optionally, in certain embodiments an inert gas is also fed to the reaction zone comprising the carbon-based catalyst. The inert gas may be chosen from the group consisting of helium, nitrogen, argon, and mixtures thereof, and preferably is nitrogen or argon. The inert gas does not comprise water or oxygen species (e.g. carbon monoxide or carbon dioxide). The reaction gas and the inert gas may be provided to the reaction zone simultaneously or not, preferably simultaneously. An inert gas may be used to dilute the reaction gas. For example, the flow ratio of reaction gas to inert gas may be in the range from about 1:0 to about 1:1, and preferably from about 1:0 to 1:0.2.

Preferably, the reaction gas is substantially free of oxygen, e.g. it contains less than 1.0 mol %, or less than 0.5 mol %, or less than 0.1 mol %, or less than 0.01 mol %, or less than 0.001 mol %, or less than 0.0001 mol %, or less than 0.00001 mol % of oxygen, as defined herein. In an example, the reaction gas is free of oxygen, as defined herein.

Preferably, the reaction gas is substantially free of sulphur species, e.g. it contains less than 1.0 mol %, or less than 0.5 mol %, or less than 0.1 mol %, or less than 0.01 mol %, or less than 0.001 mol %, or less than 0.0001 mol %, or less than 0.00001 mol % of sulphur species. In an example, the reaction gas is free of sulphur species. Sulphur species may for instance be present in the form of $H_2S$, COS, $CS_2$.

In certain embodiments, the composition of the reaction gas is comparable to the composition of a natural gas, a biogas, or a fuel/off gas stream.

In certain embodiments of a process according to the invention, the applied reaction gas is a natural gas. The term "natural gas" refers to a multi-component gas obtained from a crude oil well (associated gas) or from a subterranean gas-bearing formation (non-associated gas). The composition and pressure of natural gas can vary significantly. A typical natural gas stream contains methane as a significant component. Natural gas may also contain ethane, higher molecular weight hydrocarbons, acid gases (such as carbon dioxide, hydrogen sulphide, carbonyl sulphide, carbon disulphide, and mercaptans), and minor amounts of contaminants such as water, nitrogen, iron sulphide, wax, and crude oil. As used herein, "natural gas" may also include gas resulting from the regasification of a liquefied natural gas, which has been purified to remove contaminates, such as water, acid gases, and most of the higher molecular weight hydrocarbons (e.g. $C_{12}$+ hydrocarbons). Conventional methods can be used for removing impurities and/or adjusting the relative amount of hydrocarbon compounds present in the reaction gas. The term "biogas" refers to a multi-component gas, primarily consisting of methane and carbon dioxide, produced from raw materials such as but not limited to agricultural waste, manure, municipal waste, plant material, sewage, green waste or food waste. Biogas may be purified to remove oxygen containing compounds, prior to application as reaction gas in the present processes.

In an Embodiment, a Reaction Gas as Applied in a Process According to the Invention May have the Following Composition:

from 80.0 to 100 mol % of methane, and preferably from 90.0 to 100 mol % of methane from 0 to 50.0 mol % ethane, and preferably from 0.01 to 25.0 mol % ethane, and from 0 to 25.0 mol % propane, and preferably from 0.01 to 15.0 mol % propane, and from 0 to 15.0 mol % butane, and preferably from 0.01 to 5.0 mol % butane.

In Another Embodiment, a Reaction Gas as Applied in a Process According to the Invention May Have the Following Composition:

from 80.0 to 100 mol % of methane, and preferably from 90.0 to 100 mol % of methane from 0 to 15.0 mol % of ethane, such as from 0 to 10 mol % of ethane, or from 0 to 5 mol % of ethane, and from 0 to 15.0 mol % of propane, such as from 0 to 10.0 mol % of propane, or from 0 to 5.0 mol % of propane, or from 0 to 3.0 mol % of propane, and from 0 to 5.0 mol %, or from 0 to 3.0 mol % of butane, and from 0 to 5.0 mol %, or from 0 to 3.0 mol % of pentane, and from 0 to 5.0 mol % of nitrogen, or from 0 to 3.0 mol % of nitrogen.

One Example of a Suitable Reaction Gas for Use in a Process According to the Invention Comprises for Instance:

3.0 mol % to 70.0 mol % methane;

10.0 mol % to 50.0 mol % ethane;

10.0 mol % to 40.0 mol % propane;

5.0 mol % to 40.0 mol % butane; and 1.0 mol % to 10.0 mol % of $C_5$-$C_9$ hydrocarbons.

Another example of a suitable reaction gas for use in a process according to the invention comprises for instance: 94.9 mol % methane; 2.5 mol % ethane; 0.2 mol % propane, 0.06 mol % butane, 0.02 mol % pentane, 0.01 mol % $C_6$+ alkanes, 1.6 mol % of nitrogen, 0.7 mol % of carbon dioxide, 0.02 mol % of oxygen and traces of hydrogen.

In certain embodiments, said natural gas may be of fossil origin. In certain embodiments, said natural gas may be of renewable origin. Natural gas of renewable origin for instance includes gas produced from existing waste streams and a variety of renewable and sustainable biomass sources, including but not limited to animal waste, crop residuals and food waste, organic waste from dairies and farm, and naturally-occurring biological breakdown of organic waste at facilities such as wastewater treatment plants and landfills. In certain embodiments, said natural gas may comprise a combination of natural gas from fossil origin and from renewable source.

A process according to the invention involves a reaction step in which at least a portion of saturated $C_{1+}$ hydrocarbons as defined herein are converted into unsaturated hydrocarbons having two or more carbon atoms and hydrogen.

"Hydrocarbon having two or more carbon atoms" or "$C_2$+ hydrocarbons" are used herein as synonyms and refer to hydrocarbons having at least two carbon atoms. The term "unsaturated hydrocarbon having two or more carbon atoms" or "unsaturated $C_2$+ hydrocarbons" are used herein as synonyms and refer to hydrocarbons having at least two carbon atoms and having at least one carbon-carbon double bond. Unsaturated $C_2$+ hydrocarbons include, but are not limited to, alkenes, alkynes, and aromatic hydrocarbons.

The term "alkene," alternatively referred to as "olefin," as used herein refers to an unsaturated hydrocarbon, which may be linear, or branched, and comprise carbon-carbon double bonds. Generally, alkenes of this invention comprise unsaturated $C_2$-$C_{12}$ hydrocarbons, preferably unsaturated $C_2$-$C_{10}$ hydrocarbons, preferably unsaturated $C_2$-$C_8$ hydrocarbons, preferably unsaturated $C_2$-$C_6$ hydrocarbons, preferably unsaturated $C_2$, $C_3$, $C_4$, $C_5$, $C_6$ hydrocarbons. When a subscript is used herein following a carbon atom, the subscript refers to the number of carbon atoms that the named group may contain. Examples of alkenes include, but are not limited to ethylene, propylene, butylene, pentene, hexene, heptene, 1,2-propadiene, 1,3-butadiene, 1,3-pentadiene. "Alkene" is intended to embrace all structural isomeric forms of an alkene. For example, butylene encompasses but-1-ene, (Z)-but-2-ene, etc.

The term "alkyne", as used herein refers to an unsaturated hydrocarbon, which may be linear, or branched, and comprise carbon-carbon triple bonds. Generally, alkynes of this invention comprise unsaturated $C_2$-$C_{12}$ hydrocarbons, preferably unsaturated $C_2$-$C_{10}$ hydrocarbons, preferably unsaturated $C_2$-$C_8$ hydrocarbons, preferably unsaturated $C_2$-$C_6$ hydrocarbons, preferably unsaturated $C_2$, $C_3$, $C_4$, $C_5$, $C_6$ hydrocarbons. Examples of alkynes include, but are not limited to acetylene (ethyne), 1-butyne, 2-butyne, linear or branched pentyne, linear or branched hexyne, etc.

The term "aromatic hydrocarbons" and "$C_6$+ aromatic hydrocarbons" are used herein as synonyms and refer to unsaturated hydrocarbons with at least one closed ring of at least 6 atoms, with all of the ring atoms being co-planar or almost co-planar and covalently linked, and with all of the ring atoms being part of a mesomeric system. As used herein, the term aromatic encompasses hydrocarbons containing aromatic ring(s), including, but not limited to, benzene, toluene, and xylene, and polynuclear aromatics (PNAs), which include naphthalene, anthracene, chrysene.

In certain preferred embodiments of a process according to the invention, said unsaturated hydrocarbons having two or more carbon atoms comprise alkenes, and preferably comprise $C_2$-$C_{12}$ alkenes, or $C_2$-$C_{10}$ alkenes, or $C_2$-$C_8$ alkenes, or $C_2$-$C_6$ alkenes, or $C_2$-$C_4$ alkenes. In certain preferred embodiments of a process according to the invention, said unsaturated hydrocarbons having two or more carbon atoms comprise alkenes selected from the group consisting of ethylene, propylene, butylene, pentene, hexene, and heptene and any combinations of two or more thereof.

In certain embodiments of the present processes, said unsaturated hydrocarbons having two or more carbon atoms comprise alkynes, and preferably comprise $C_2$-$C_{12}$ alkynes, or $C_2$-$C_{10}$ alkynes, or $C_2$-$C_8$ alkynes, or $C_2$-$C_6$ alkynes, or $C_2$-$C_4$ alkynes. In certain preferred embodiments of the present processes said unsaturated hydrocarbons having two or more carbon atoms comprise alkynes selected from the group consisting of acetylene, 1-butyne, 2-butyne, pentyne, hexyne and any combinations of two or more thereof.

In certain embodiments of the present processes, said unsaturated hydrocarbons having two or more carbon atoms comprise $C_6$+ aromatic hydrocarbons, preferably aromatic $C_6$-$C_{12}$ hydrocarbons, and more preferably aromatic hydrocarbons selected from the group consisting of benzene, toluene, naphthalene, and any combinations of two or more thereof.

In certain embodiments of the present processes, said hydrocarbons having two or more carbon atoms comprise unsaturated hydrocarbons having two or more carbon atoms, and preferably comprise alkenes and/or alkynes as defined herein, and optionally $C_6$+ aromatic hydrocarbons as defined herein.

In certain preferred embodiments, said hydrocarbons having two or more carbon atoms comprise a combination of the above indicated embodiments. For example, hydrocarbons having two or more carbon atoms, such unsaturated hydrocarbons having two or more carbon atoms, may include combinations of alkenes selected from the group consisting of ethylene, propylene, butylene, pentene, hexene and heptene and any combinations of two or more thereof; and alkynes selected from the group comprising acetylene, 1-butyne, 2-butyne, pentyne, hexyne, any combinations of two or more thereof, and optionally $C_6$+ aromatic hydrocarbons as defined herein, such as $C_6$+ aromatic hydrocarbons selected from the group consisting of benzene, toluene, naphthalene, and any combinations of two or more thereof.

In certain preferred embodiments, said hydrocarbons having two or more carbon atoms, and preferably said unsaturated hydrocarbons having two or more carbon atoms, comprise ethylene and/or acetylene, optionally $C_6$+ aromatic hydrocarbons as defined herein, such as $C_6$+ aromatic hydrocarbons selected from the group consisting of benzene, toluene, naphthalene, and any combinations thereof.

In certain embodiments, said unsaturated hydrocarbons having two or more carbon atoms, as obtained by a process according to the invention comprise:

from 0.5 to 70.0 mol %, or from 0.5 to 50.0 mol %, or from 0.5 to 30.0 mol %, or from 0.5 to 20.0 mol % of alkenes, preferably $C_2$-$C_{12}$ alkenes, preferably $C_2$-$C_1$ alkenes, preferably $C_2$-$C_8$ alkenes, preferably $C_2$-$C_6$ alkenes, preferably $C_2$-$C_4$ alkenes, and more preferably ethylene; and from 0.5 to 70.0 mol % of alkynes, or from 0.5 to 50.0 mol %, or from 0.5 to 30.0 mol %, or from 0.5 to 20.0 mol % of alkynes, and preferably $C_2$-$C_{12}$ alkynes, preferably $C_2$-$C_{10}$ alkynes, preferably $C_2$-$C_8$ alkynes, preferably $C_2$-$C_6$ alkynes, preferably $C_2$-$C_4$ alkynes, and more preferably acetylene, and optionally from 0 to 50.0 mol %, or from 0 to 25.0 mol %, or from 0 to 10.0 mol % of aromatic hydrocarbons, preferably $C_6$+ aromatic hydrocarbons, preferably aromatic $C_6$-$C_{12}$ hydrocarbons, and more preferably aromatic hydrocarbons selected from the group consisting of benzene, toluene, naphthalene, and any combinations of two or more thereof.

In an example, unsaturated hydrocarbons having two or more carbon atoms as obtained by the present processes may comprise:

from 1.0 to 10.0 mol % of ethylene, such as from 1.5 to 9.0 mol % of ethylene, or from 4.5 to 7.5 mol % of ethylene, from 1.0 to 10.0 mol % of acetylene, such as from 1.5 to 9.0 mol % of acetylene, or from 4.5 to 7.5 mol % of acetylene, from 0 to 4.5 mol % of benzene, such as from 1.0 to 4.0 mol % of benzene, or from 1.5 to 3.6 mol % of benzene, from 0 to 1.5 mol % of toluene, such as from 0.1 to 1.3 mol % of toluene, or from 0.3 to 1.2 mol % of toluene, and from 0 to 3.0 mol % of naphthalene, such as from 0.3 to 2.5 mol % of naphthalene, or from 0.6 to 2.1 mol % of naphthalene.

In an example, unsaturated hydrocarbons having two or more carbon atoms as obtained by the present processes comprise from 4.5 to 7.5 mol % of ethylene, from 4.5 to 7.5 mol % of acetylene, from 1.5 to 3.6 mol % of benzene, from 0.3 to 1.2 mol % of toluene, and from 0.6 to 2.1 mol % of naphthalene.

In another example, unsaturated hydrocarbons having two or more carbon atoms as obtained by the present processes may comprise:

from 0.1 to 7.0 mol % of ethylene, such as from 0.5 to 3.0 mol % of ethylene, such as from 1.5 to 2.5 mol % of ethylene, from 0.3 to 7.0 mol % of acetylene, such as from 0.5 to 5.0 mol % of acetylene, such as from 1.5 to 4.5 mol % of acetylene, from 0 to 3.0 mol % of benzene, such as from 0 to 1.5 mol % of benzene, such as from 0.5 to 1.2 mol % of benzene, from 0 to 1.5 mol % of toluene, such as from 0 to 0.5 mol % of toluene, such as from 0.1 to 0.4 mol % of toluene, from 0 to 1.5 mol % of toluene, such as from 0 to 1.0 mol % of naphthalene, such as from 0.2 to 0.7 mol % of naphthalene.

In another example, unsaturated hydrocarbons having two or more carbon atoms as obtained by the present processes comprise from 1.5 to 2.5 mol % of ethylene, from 1.5 to 4.5 mol % of acetylene, from 0.5 to 1.2 mol % of benzene, from 0.1 to 0.4 mol % of toluene, and from 0.2 to 0.7 mol % of naphthalene.

The percentage of saturated hydrocarbons in the reaction gas converted into unsaturated $C_2$+ hydrocarbons is preferably greater than 5.0%, or greater than 7.0%, or greater than 10.0%, or greater than 15.0%, or greater than 20.0%, or greater than 30.0%. Conversion percentage is defined as explained in the example section below, taking methane as example. Conversions can be determined by using conventional methods such as gas chromatography or the like. In an example, the amount of methane in the reaction gas converted to unsaturated hydrocarbons having two or more carbon atoms as defined herein is preferably greater than 5.0%, or greater than 7.0%, or greater than 10.0%, or greater than 15.0%, or greater than 20.0%, or greater than 30.0%.

The present invention further allows to produce unsaturated $C_2+$ hydrocarbons at high yields. Product (i.e. $C_2+$ hydrocarbons) yields are defined as explained in the example section below, taking benzene as example. In certain embodiments, a process according to the invention provides a yield of an unsaturated $C_{2+}$ hydrocarbon as defined herein, which is greater than 5%, or greater than 10%, or greater than 15%, or greater than 20%, or greater than 30%. In an example, a process according to the invention provides an ethylene yield greater than 5%, or greater than 10%, or greater than 15%, or greater than 20%, or greater than 30%. In another example, a process according to the invention provides an acetylene yield greater than 5%, or greater than 10%, or greater than 15%, or greater than 20%, or greater than 30%.

In accordance with the present processes, a reaction gas as defined herein and comprising saturated $C_{1+}$ hydrocarbons is supplied to the reaction zone comprising a carbon-based catalyst as defined herein. As understood herein, a reaction zone may be an individual reactor or a reactor may comprise reaction zones, which are for instance kept at different temperatures. The step of contacting the saturated hydrocarbon with the carbon-based catalyst of the invention may be performed in any suitable reactor, as known to a skilled man, for example in a fixed bed reactor or moving bed reactor. Hence, the carbon-based catalyst may be provided in said reaction zone in a fixed reactor bed or in a moving reactor bed.

As used herein, the term "fixed bed reactor" refers to a reactor or reactor zone where a catalyst material (e.g. particulate catalyst material) is substantially immobilized within the reactor/reactor zone and reactant(s) flows through the catalyst bed. A fixed bed reactor may include vessel(s) containing the catalyst material. Vessels may be cylindrical or spherical. Vessels may be horizontally oriented or vertically oriented.

As used herein, the term "moving bed reactor" refers to a reactor or reactor zone wherein a catalyst material (e.g. particular catalyst material) travels through the reactor and may be removed from the reactor. Typically the catalyst material enters at one end of the reactor and flows out the opposite end of the reactor. The moving bed reactor may be connected to a regeneration system as to regenerate the spent catalyst. The regenerated catalyst may then be returned to the moving bed reactor for further use in the reaction, as described herein.

Process according to the invention are performed at conditions effective for the hydrocarbon conversion, i.e. the non-oxidative conversion of saturated hydrocarbons (e.g., methane) into unsaturated $C_2+$ hydrocarbons (e.g. ethylene and/or acetylene) and hydrogen. To that end, the reaction zone containing said carbon-based catalyst is operated under effective reaction conditions to convert at least a portion of the saturated hydrocarbons in the reaction gas. The term "effective," as used in the specification and/or claims, means adequate to accomplish a desired, expected, or intended result. The term "effective reaction conditions" as used in the specification and/or claims, means conditions selected from but not limited to reaction temperature, reaction pressure, flow rate(s) of reaction gas, molar ratio of components, amount of catalyst, etc. that are effective to convert at least a portion of saturated $C_{1+}$ hydrocarbons into unsaturated $C_{2+}$ hydrocarbons and hydrogen under non-oxidative conditions.

The hydrocarbon conversion of saturated hydrocarbons as described herein is accomplished via endothermic reactions, which present various challenges, such as maintaining sufficient temperatures required for the reactions, including transferring a large amount of heat to the carbon-based catalyst.

In certain embodiments, the present processes comprise heating of the interior of said reaction zone containing said carbon-based catalyst to an effective reaction temperature by heating the catalyst material which is provided inside the reaction zone. Induction heating (IH) technology is thus applied to heat a carbon-based catalyst as defined herein, which is provided within the reaction zone. Thus, in a process according to the invention, a reaction zone containing said carbon-based catalyst is heated by heating the carbon-based catalyst contained in said reaction zone by induction heating.

Induction heating in general involves a process in which a reaction medium (here the reaction gas) is brought into contact with a heating medium (here a carbon-based catalyst) that can be heated by electromagnetic induction. This process enables heat to be generated within the body of the reactor or reaction zone (by heating the catalyst provided in the body of the reactor).

Induction heating is the process of heating an electrically conducting object (here a carbon-based catalyst as defined herein) by magnetic induction, through heat generated in the object by eddy currents (also called Foucault currents) and/or hysteresis loss. An induction heater typically consists of an electromagnet, and an electronic oscillator which passes a high-frequency alternating current (AC) through the electromagnet. The rapidly alternating magnetic field penetrates the object, generating electric currents inside the conductor called eddy currents. The eddy currents flowing through the resistance of the material heat it by Joule heating. Eddy current heating is also denoted ohmic heating. Eddy current heating is thus a process by which the passage of an electric current through a conductor (here the carbon-based catalyst material) releases heat.

In an example of the present processes, said carbon-based catalyst is heated by generating an alternating electromagnetic field within the reaction zone containing said carbon-based catalyst upon energization by a power source supplying alternating current, where the alternating electromagnetic field passes through the reaction zone thereby generating an electric current in said carbon-based catalyst and heating the carbon-based catalyst.

In an example, a bed of a carbon-based catalyst as defined herein is heated in a reaction zone by means of an induction coil surrounding said zone. The heat is generated in the bed itself by passing through said coil an alternating current having a suitable frequency.

In the above embodiments of a process according to the invention; the carbon-based catalyst is heated by induction. This provides the heat necessary for the endothermic chemical conversion reaction. The heating of the reactant(s) in the reaction gas is provided by conduction when the reactant(s) is(are) brought into contact with the carbon-based catalyst, typically by being adsorbed onto the surface of the carbon-based catalyst, as well as by convection prior to the reactant(s) contacting the surface of the carbon-based catalyst.

An important advantage of applying the induction heating process in the present invention is that the heat is generated inside the object itself (i.e. the catalyst), and the catalyst material can be very rapidly heated. The heat is generated locally in the reaction zone at the site where the heat is required. A direct heating mode associated with a high heating rate allows to operate endothermic reaction without facing its intrinsic drawback, i.e. temperature loss within the catalyst bed as a function of conversion of the reactant. Fast temperature regulation of induction heating allows to maintain the catalyst bed temperature as close as possible to the targeted one, regardless the reactant conversion level.

Another advantage of the induction heating, as applied in the present processes, is that heat transfer is proportional to the amount of conductor localized within the induction coil. In other words, the power supply to maintain the catalyst bed temperature decreases as coke deposit increases inside the catalyst bed. Thus, the overall power to operate the reaction slightly decreases with time-on-stream where higher amount of carbonaceous species accumulate within the reactor.

In accordance with the present processes, a reaction zone containing said carbon-based catalyst is heated to a reaction temperature of at least 350° C. by heating said carbon-based catalyst contained in said reaction zone by induction heating, such as to a reaction temperature of at least 400° C., or at least 450°, or at least 500° C., or at least 550° C., or at least 650° C., or at least 700° C., or at least 750° C., or at least 800° C. by heating said carbon-based catalyst contained in said reaction zone by induction heating. In certain preferred embodiments, said reaction zone containing said carbon-based catalyst is heated to a reaction temperature which is lower than 2000° C., or lower than 1500° C., such as lower than 1300° C., or lower than 1100° C. by heating said carbon-based catalyst contained in said reaction zone by induction heating. In an example a process according to the invention is characterised in that said carbon-based catalyst is heated by means of induction heating thereby heating the reaction zone containing said carbon-based catalyst to a reaction temperature which is comprised between 35° and 1500° C., such as between 50° and 1200° C., or between 60° and 1000° C., or between 55° and 900° C., or between 65° and 800° C.

The reaction gas may be optionally heated prior to supplying it to the reaction zone. It is however preferred that the reaction gas may be supplied to said reaction zone in step c) at a temperature which is lower than the reaction temperature applied in step b) of the present processes. In certain embodiments, wherein the reaction zone containing said carbon-based catalyst is heated in said reaction zone by induction heating, it is preferred that the reaction gas is supplied to the reaction zone in step c) of the present processes at a temperature lower than 500° C., or lower than 450° C., or lower than 400° C., or lower than 350° C., or lower than 300° C., or lower than 250° C., or lower than 200° C., or lower than 150° C., or lower than 100° C.

It will be understood that suitable temperatures of the reaction gas to be supplied in step c) of process according to the invention will depend on the reaction temperature as applied in the process.

In certain embodiments, the reaction gas is not heated prior to being supplied to said reaction zone in step c).

The pressure within the reactor in which the non-oxidative hydrocarbon conversion is carried out is preferably comprised between 0.1 and 30.0 bar, such as between 0.1 and 20 bar (0.01 to 2 MPa), and preferably between 0.1 and 15 bar (0.01 to 1.5 MPa), such as between 0.1 and 10 bar (0.01 to 1 MPa), or between 0.5 and 5 bar (0.05 to 0.5 MPa). For example, the pressure is from 0.01 to 0.3 MPa. In some embodiments, a process according to the invention can be also operated at atmospheric pressure.

The reaction gas is preferably supplied to the reaction zone at a weight hourly space velocity (WHSV), i.e. the weight of saturated hydrocarbons flowing per unit weight of the catalyst per hour, in the range of between 0.1 and 100 $h^{-1}$, or between 0.1 and 50 $h^{-1}$, or from 0.1 to 10 $h^{-1}$, or from 0.1 to 5 $h^{-1}$. In certain embodiments, a WHSV is fixed at the beginning of the process and can be varied depending on the carbon deposit onto the catalyst with time-on-stream. In other embodiments, the reactant gaseous space velocity can be changed as a function of time-on-stream in order to maintain the WHSV at a constant level during operation.

The carbon-based catalyst applied in a process of the invention is suitable for catalysing a non-oxidative conversion of a saturated hydrocarbon, in particular for the non-oxidative conversion of alkanes, such as methane, ethane, propane, etc. to hydrogen and unsaturated $C_2$+ hydrocarbons, particularly to hydrogen and unsaturated $C_2$+ hydrocarbons such as ethylene, acetylene, propene, etc. as it can form unsaturated $C_2$+ hydrocarbons in a high yield and with a high selectivity. By using a carbon-based catalyst of the invention in non-oxidative conversion of saturated hydrocarbons as defined herein, has the important advantages, including (i) that cokes/carbonaceous materials formed on the carbon-based catalyst during a process according to the invention do not significantly reduce catalyst activity; (ii) that the carbon-based catalyst having carbonaceous materials deposited thereon may therefore be recycled and re-used: (iii) that cokes/carbonaceous deposits on the catalyst improve heat harvesting from the induction heating, thus lowering the overall energy input to a process according to the invention as a function of time-on-stream. Also, a carbon catalyst displays better resistance towards deactivation by trace amounts of sulphur or nitrogen-containing compounds in the processing feed, as compared to metal-based catalysts.

The terms "carbon-based catalyst" or "carbon-catalyst" are used herein as synonyms and refer to compounds that are—as such—catalytically active, i.e. that act as a catalyst and facilitate a chemical reaction. As generally used herein, the term "carbon-based catalyst" refers to a carbon-containing compound which can enhance the rate and/or efficiency of a chemical reaction process as compared to the rate and/or efficiency of the same chemical reaction process in the absence of the catalyst. Such catalyst materials modify and increase the rate of chemical reactions without being consumed in the process. The term "carbon-based catalyst" as used herein does not intend to refer to materials based on carbon that are used as coating layer on other materials.

In some embodiments, a "carbon-based catalyst" or "carbon catalyst" as used herein comprises, and preferably consists of, carbon. In certain embodiments a carbon-based catalyst as used herein has a carbon content (mol %) of at least about 75.0, at least 80.0, at least 85.0, at least 90.0, at least 95.0, at least 97.0, at least 99.0, at least 95.5, or at least 99.9 mol % of carbon.

In certain embodiments, a carbon-based catalyst as used in the present process comprises at least 90.0 wt %, more preferably at least 92.0 wt %, more preferably at least 95.0 wt %, more preferably at least 96.0 wt %, more preferably at least 97.0 wt %, more preferably at least 98.0 wt %, more preferably at least 99.0 wt %, more preferably at least 99.5 wt %, more preferably at least 99.9 wt %, of carbon, based on the total weight of said catalyst. In certain preferred embodiments, a carbon-based catalyst as used in the present process consists of carbon.

In certain preferred embodiments, said carbon-based catalyst is entirely made of carbon (i.e. consists of carbon). In other words, in such preferred embodiments, the carbon-based catalyst as applied in the present process is a "single-component" catalyst, i.e. a catalyst that is made solely of carbon component (100 mol % C or 100 wt % of C). Carbon content of materials may be determined using techniques that are well known in the art, such as quantitative X-Ray fluorescence (XRF) or Induced Coupled Plasma-Mass Spectrometry (ICP-MS) or Thermogravimetry (TG) analysis.

In preferred embodiments of the present invention the carbon-based catalyst applied in the process is a "fresh" carbon-based catalyst. The term "fresh" catalyst is conventional in the art, and intends to refer to a catalyst that is used for a first time, i.e. that has not been previously subjected to a catalysed reaction or that is not recycled. The term "fresh" catalyst may be understood as a "starting" catalyst, or "initial" catalyst or "original" catalyst in the context of the present invention.

In contrast therewith, the term "spent catalyst composition" or "spent catalyst" is also well known in the art, and in general refers to a catalyst that has been previously used in a catalysed reaction. The terms "spent catalyst" and "spent carbon catalyst" are used herein interchangeably.

In certain preferred embodiments, a carbon-based catalyst as used in the present process herein is non-porous. The term "non-porous" or "nonporous" as used herein refers to a carbon based catalyst that has a BET surface area of at most 5.0 m$^2$/g, such as from 0.10 to 5.0 m$^2$/g, or from 0.5 to 3.0 m$^2$/g, or from 1.0 to 5.0 m$^2$/g, or from 1.0 to 3.0 m$^2$/g, as determined by ASTM-D-3663 (2020).

Several forms of carbon can be applied as a carbon-based catalyst in the present invention. In some preferred embodiments, said carbon-based catalyst is selected from the group comprising, and preferably consisting of, graphene, few-layer graphene (FLG), graphite (G), graphite felt (GF), carbon felt (CF), graphite cloth, graphite fabric, expanded graphite (EG), carbon nanofiber (CNF), carbon nanotubes (CNTs), and any combinations thereof.

In certain other preferred embodiments, the present invention is carried out using a non-porous carbon catalyst which is selected from the group consisting of graphite (G), carbon felt (CF), graphite felt (GF), expanded graphite (EG), carbon fabric, graphite fabric, carbon cloth, graphite cloth, graphene, and any combinations thereof, as has been exemplified in the example section below.

In certain preferred embodiments, said carbon-based catalyst is graphene. As used herein, the term "graphene" intends to refer to a molecule in which a plurality of carbon atoms (e.g., in the form of five-membered rings, six-membered rings, and/or seven-membered rings) are covalently bound to each other to form a (typically sheet-like) polycyclic aromatic molecule. Consequently, and at least from one perspective, a graphene may be viewed as a single layer of carbon atoms that are covalently bound to each other (most typically sp$^2$ bonded). It should be noted that under the scope of this definition, the term "graphene" also includes molecules in which several (e.g., two, three, four, five to ten, one to twenty, one to fifty, or one to hundred) single layers of carbon atoms are stacked on top of each other, preferably to a maximum thickness of about 100 nanometres. Consequently, the term "graphene" as used herein refers to a single layer of aromatic polycyclic carbon as well as to a plurality of such layers having a thickness of preferably of less than about 100 nanometres. The term "few-layer graphene (FLG)" as used herein intends to refer to graphene with about 2 to 10 layers.

In certain preferred embodiments, said carbon-based catalyst is graphite. The term "graphite" as used herein, describes the well-known crystalline form of the element carbon with its atoms arranged in a hexagonal structure. A graphitic carbon has the characteristics of an ordered three-dimensional graphite crystalline structure consisting of layers of hexagonally arranged carbon atoms stacked parallel to each other as determined by X-ray diffraction. The term graphite herein used includes both, natural graphite, i.e. essentially in its geologically occurring natural crystalline form) and synthetic graphite, i.e. synthetically prepared or processed graphite. Examples of natural graphite include so-called amorphous (nanocrystalline) graphite, flake graphite, and vein graphite. Examples of synthetic graphite include pyrolytic graphite, highly oriented pyrolytic graphite (HOPG), synthetic graphite flakes. The term "synthetic graphite" as used herein unless further qualified also intends to include non-expanded and expanded forms of graphite (including expanded graphite that has been exfoliated).

In certain preferred embodiments, said carbon-based catalyst is expanded graphite. The term "expanded graphite" (EG) as used herein refers to graphite or graphite flakes that have been expanded, i.e., increased in volume. Expansion may include exposure to an intercalation agent, formation of a graphite salt between graphite layers, and exposure to a high temperature shock treatment in which the intercalation agent escapes, leaving behind a gap between the graphite layers. Expanded graphite for use in the present processes may be produced by any fabrication method known in the art, including for instance chemical insertion followed by thermal expansion.

For instance, expanded graphite may be formed by heat treatment of expandable graphite. Generally, expanded graphite, differently from expandable graphite, shows an increased interlayer spacing and higher carbon content both due to the heat treatment procedure. The term "expandable graphite" refers to pre-treated graphite in which the layered crystal graphite structure is intercalated with small molecules such as sulphur or nitrogen compounds. The layered, planar structure of graphite allows that atoms or small molecules can intercalate between the carbon layers. Expandable graphite appears as a dry material with a minimal acidity since the intercalant is sealed within its carbon lattice. During this process so-called expandable graphite is produced. Expandable graphite is commercially available, or can be manufactured for example by acid treatment of graphite flake in nitric and sulphuric acid. The expandable graphite still retains the interlayer distance of natural flake graphite, and is chemically stable under air condition and can be easily stored. Graphite, particularly flake graphite, can be treated with acid such as sulphuric acid, nitric acid, or acetic acid to intercalate into the crystal layers of the graphite. The introduction of acid into the graphite layers can be supported by treatment with oxidants or by electrochemical treatment. After the reaction, the expandable graphite can be neutralized, washed, and dried. While the carbon atoms are tightly bound to each other within a layer, the layers themselves can be expanded and separated. When expandable graphite is then exposed to heat treatment an expansion of the intercalated graphite layers is induced. Generally, expanded graphite, differently from expandable graphite, shows an increased interlayer spacing and higher carbon content both due to the heat treatment procedure.

In certain preferred embodiments, said carbon-based catalyst is graphite felt. The term "graphite felt" (GF) as used herein refers to carbon felt, i.e. a textile material that predominantly comprises randomly oriented and intertwined carbon filaments or fibers, that has been subjected to a graphitisation process, which may involve heat treating the carbon felt at high temperatures, such as in the range of about 2600° C. to about 3300° C. During the graphitising process, the randomly oriented and intertwined carbon filaments or fibers may be converted into a three-dimensionally ordered graphite structure.

In certain preferred embodiments, said carbon-based catalyst is carbon felt. The term "carbon felt" (CF) as used herein refers to a textile material that predominantly comprises randomly oriented and intertwined carbon filaments or fibers. The term "felt" refers to a non-woven textile formed from natural (e.g., plant (e.g., bamboo) or animal (e.g., wool)) fibers or synthetic (e.g., polyester, polypropylene, fluoropolymers (e.g., PTFE), polyacrylonitrile, any combination thereof, or the like) fibers, wherein the fibers are compressed and matted together until they connect to form a fabric (e.g., cloth). Without limitation, carbon felt suitable for use in the instant invention is commercially available e.g. from Avcarb or Cera Materials. In some embodiments, the carbon felt has a thickness of from about 2 mm to about 20 mm. For example, the carbon felt may have a thickness of from about 4 to about 15 mm, from about 6 to about 10 mm, or from about 2 to about 6 mm. The CF can be also used with different configurations, e.g. as such, or in "rolled" configuration, for giving a different surface contact.

In certain preferred embodiments, said carbon-based catalyst is carbon nanofiber. As used herein, the term "carbon nanofiber" or "CNF" means and includes a carbon-containing material comprising a solid cylindrical shape, with prismatic planes exposure, substantially free of voids (e.g., without a hollow central portion). A carbon nanofiber may be similar to a carbon nanotube (CNT), but may include a solid core rather than a hollow central portion, and prismatic planes exposure instead of basal ones. Carbon nanofibers may exhibit a rod-like shape and may exhibit a greater density than CNTs. In some embodiments, carbon nanofibers may exhibit a greater density than CNTs having the same diameter. Carbon nanofibers may also be in the form of stacked graphene sheets. Carbon nanofibers may be formed through any method known in the art, including deposition from carbon vapour, such as by catalytic chemical vapour deposition (CCVD) wherein carbon is deposited in the presence of a transition metal catalyst on a substrate, or other methods of forming carbon nanofibers known in the art.

In certain embodiment, carbon nanofibers as used herein have a length of about 100-1000 nm, such as about 150-500 nm. In certain embodiment, carbon nanofibers as used herein have the aspect ratio, i.e. the ratio of length to the outer diameter, of preferably more than about 10, such as more than about 50, or more than about 100, or more than about 1000, or more than about 2000.

In certain embodiments, carbon nanofibers as used herein comprise carbon nanofibers having a mean average diameter less than 1000 nm. In certain embodiments, the carbon nanofibers have a mean average diameter less than 500 nm, such as less than 300 nm. For example, carbon nanofibers may have a mean average diameter between about 50 and 300 nm, such as between about 50 and 250 nm.

In certain preferred embodiments, said carbon-based catalyst is a carbon nanotube. As used herein, the term "carbon nanotube" or "CNT" means and includes a hollow cylindri-cal or tube shape carbon molecule, defining a void therein, which may be empty or filled with another material. CNTs may be closed at one or both ends. CNTs may be conceptualized as rolled graphene sheets, having a hexagonal lattice of carbon molecules with basal planes exposure. Depending on the rolling degree and the way the original graphene sheet is formed, carbon nanotubes of different diameter and internal geometry can be formed. Carbon nanotubes formed by rolling up of a single sheet forming the aforementioned cylinder, are called "single-walled" carbon nanotubes. The carbon nanotubes formed by rolling up more than one sheet of graphene with a structure that resembles a series of concentric cylinders of increasing diameters from the centre to the periphery are called "multi-walled" carbon nanotubes. Suitable carbon nanotubes for use in the present invention encompass single-walled carbon nanotubes as well as multi-walled carbon nanotubes. In certain embodiments wherein carbon nanotubes are multi-walled carbon nanotubes, the multi-walled carbon nanotubes comprise include 2 or more, such as from 2 to 5, graphitic layers.

In certain embodiments, carbon nanotubes as used herein have a high aspect ratio, i.e. length-to-diameter ratio, preferably an aspect ratio of between 10 and 10,000,000 to 1, such as between 100 and 10,000 to 1.

In certain embodiments, carbon nanotubes as used herein have an average outer diameter of about 2 to 20 nm, such as about 5 to 15 nm, such as about 8 to 12 nm, such as about 10 nm. The average inner diameter of carbon nanotubes as used herein can be about 0.5 to 100 nm, or about 1 nm to 50 nm.

It will be understood that a "carbon-based catalyst" as defined herein is meant to be used as such in a process according to the invention, and is not provided on or combined with a support. In other words, the carbon-based catalyst applied in the present process is an unsupported catalyst. The terms "unsupported" and "non-supported" may be used as synonyms and thus refer to a carbon-based catalyst that is not provided on a support material.

In accordance with the invention, the carbon-based catalyst applied in the present process is thus not combined with or provided on a support. A carbon-based catalyst as applied in the present process is for instance not coated on, or not impregnated on, or not mixed with, or not provided as a phase on a support, such as an organic support and/or inorganic support.

Organic and inorganic catalyst support materials are well known by the skilled person. Such support materials excluded from the present invention may for instance include aluminas, silicas, titanias, zirconias, aluminosilicates (such as clays and/or zeolites), spinels (such as zinc aluminate, zinc titanate, and/or magnesium aluminate), or combinations thereof. Examples of catalyst supports that are excluded from the present invention also include inorganic carrier materials such as magnesium halides, or the like, inorganic oxides (e.g. silica, alumina, or silica-alumina are magnesia, titania, zirconia, and mixtures thereof), metals or metal oxides. Specific examples that are excluded from use in the present invention include alpha-alumina supports, gamma-alumina support (e.g. gamma-$Al_2O_3$), $SiO_2$ supports, silicon carbide supports, etc.

It will also be understood from the present invention that a "carbon-based catalyst" as disclosed herein does not encompass carbon-based material that is used as support material for another catalyst. A "carbon-based catalyst" as used herein does not refer to a support (used to support another catalyst) comprising or consisting of carbon or carbon material. Consequently, it will also be understood that the term "carbon-based catalyst" refers to a component which is free of any other catalyst material.

The term "carbon-based catalyst" does not refer to metallic compounds or metal-containing catalysts, such as but not limited to zeolites, iron catalysts, metal nitrides, metal oxide catalysts, etc. which are coated or covered or deposited on a carbon-based support, or which are coated with a material or layer containing carbon. It will also be understood that the term "carbon-based catalyst" does not intend to include coke, which is obtained or made by heating coal, or petroleum coke or carbon black or any mixture thereof.

In certain embodiments, a process according to the invention is carried out in the absence of any other catalyst material which is not a carbon-based catalyst as defined herein. For instance, a process according to the invention is carried out in the absence of a metal-containing catalyst. A process according to the invention is carried out in the absence of a zeolite catalyst. A process according to the invention is carried out in the absence of a metal catalyst.

A carbon-based catalyst as defined herein is "substantially free of metal", or preferably is free of metal.

"Metals" as used in this context refers to metals selected from the group consisting of transition metals, alkali metals and alkaline earth metals. The "metals" also encompass compounds of metal thereof, e.g., metal oxides. In the present invention, the term "transition metal" as used herein refers to any element in the d-block of the periodic table, including the elements of the $3^{rd}$ to $12^{th}$ group of the periodic table. Exemplary elements of these groups include e.g. V, Cr, Mn, Fe, Co, Mo, Ni, Au, Pt, Pd, Ru and Rh. The term "transition metal" further includes any element in the f-block of the periodic table, including the elements of the lanthanide and actinide series.

In the present invention, the term "alkali metal" as used refers to any element in group 1 excluding hydrogen in the periodic table, including lithium (Li), sodium (Na), potassium (K), rubidium (Rb), Caesium (Cs) and francium (Fr). In the present invention, the term "alkaline-earth metal" as used refers to any element in group 2 in the periodic table, including beryllium (Be), magnesium (Mg), calcium (Ca), strontium (Sr), barium (Ba) and radium (Ra).

In certain preferred embodiments of the invention, a carbon-based catalyst as defined herein has a concentration of metal (as defined herein above) which is less than 3000 ppm, or less than 2000 ppm, or less than 1000 ppm. In certain preferred embodiments, a carbon-based catalyst as defined herein has a concentration of metal (as defined herein above) of less than 500 ppm. In certain preferred embodiments, a carbon-based catalyst as defined herein has a concentration of metal (as defined herein above) of less than 300 ppm. In certain preferred embodiments, a carbon-based catalyst as defined herein has a concentration of metal (as defined herein above) of less than 100 ppm. In certain preferred embodiments, a carbon-based catalyst as defined herein has a concentration of metal (as defined herein above) of less than 50 ppm. In certain preferred embodiments, a carbon-based catalyst as defined herein has a concentration of metal (as defined herein above) of less than 10 ppm.

In certain preferred embodiments of the invention, a carbon-based catalyst as defined herein has a concentration of metal (as defined herein above) which is less than 0.3% by weight, based on the total weight of the catalyst, such as less than 0.2 wt %, or less than 0.1 wt %, or less than 0.05 wt %, or less than 0.03 wt %, or less than 0.01 wt %, or less than 0.005 wt %, based on the total weight of the carbon-based catalyst.

In certain preferred embodiments, a carbon-based catalyst as used herein is free of any metal (as defined herein above). A carbon-based material as defined herein has therefore not been impregnated with metals (as defined above).

Metal content of a carbon-based catalyst as provided herein may be determined by techniques known in the art such as atomic absorption spectroscopy (AAS) or other elemental analysis technique, such as x-ray photoelectron spectroscopy (XPS), or mass spectrometry (e.g., inductively coupled plasma mass spectrometry, or "ICP-MS") or X-ray fluorescence (XRF).

The skilled person is aware of which method to use to determine the level metal in a carbon-based catalyst as used herein. "Free of any metal" in this context is meant to refer to the absence of detection of a metal (as defined) using the most sensitive technique available for that purpose.

In certain embodiments, a carbon-based catalyst as used in the present process comprises less than 10.0 wt %, preferably less than 5.0 wt %, preferably less than 3.0 wt %, more preferably as less than 1.0 wt %, more preferably as less than 0.1 wt %, of inorganic oxide(s), based on the total weight of the carbon-based catalyst. In certain preferred embodiments, a carbon-based catalyst as used in the present process does not comprise inorganic oxide(s).

"Inorganic oxides" are well known to the skilled person and refer to binary oxygen compounds where the inorganic component is the cation and the oxide is the anion. Examples of inorganic oxides include for instance silica, alumina, silica-alumina, titania, zirconia, ceria, yttria, and magnesia components, and mixtures thereof. "Inorganic oxides" may include metals (metal oxides); and metalloids (metalloid oxides). Examples of inorganic oxides include for instance $Al_2O_3$, $Ga_2O_3$, $GeO_2$; $SiO_2$, etc.

In certain embodiments, the present invention provides a process for the non-oxidative conversion of saturated $C_{1+}$ hydrocarbons into unsaturated $C_{2+}$ hydrocarbons and hydrogen in the presence of an unsupported carbon-based catalyst having a carbon content of at least 75.0 mol %, based on the total weight of the carbon-based catalyst, such as at least 80.0, 85.0, 90.0, 95.0, 97.0, 99.0, or 99.9 mol % of carbon, wherein the process comprises the steps of:

a) supplying said carbon-based catalyst to a reaction zone, b) directly heating of said carbon-based catalyst contained in said reaction zone by means of induction heating thereby indirectly heating the reaction zone containing said carbon-based catalyst to a reaction temperature of at least 350° C.;

c) supplying a reaction gas comprising saturated $C_{1+}$ hydrocarbons to said heated reaction zone comprising said carbon-based catalyst; and d) subjecting said reaction gas to a non-oxidative conversion in the presence of said carbon-based catalyst in said heated reaction zone thereby converting at least a portion of said saturated $C_{1+}$ hydrocarbons into unsaturated $C_{2+}$ hydrocarbons and hydrogen.

In certain embodiments, the present invention provides a process for the non-oxidative conversion of saturated $C_{1+}$ hydrocarbons into unsaturated $C_{2+}$ hydrocarbons and hydrogen in the presence of an unsupported carbon-based catalyst having a carbon content of at least 75.0 mol %, based on the total weight of the carbon-based catalyst, such as at least 80.0, 85.0, 90.0, 95.0, 97.0, 99.0, or 99.9 mol % of carbon, and a metal content which is less than 3000 ppm, such as less than 2000 ppm, or less than 1000 ppm, or less than 500 ppm, or less than 300 ppm, or less than 100 ppm, or less than 50 ppm based on the total weight of the carbon-based catalyst, Wherein the Process Comprises the Steps of:

a) supplying said carbon-based catalyst to a reaction zone, b) directly heating of said carbon-based catalyst contained in said reaction zone by means of induction heating thereby indirectly heating the reaction zone containing said carbon-based catalyst to a reaction temperature of at least 350° C.;

c) supplying a reaction gas comprising saturated $C_{1+}$ hydrocarbons to said heated reaction zone comprising said carbon-based catalyst; and d) subjecting said reaction gas to a non-oxidative conversion in the presence of said carbon-based catalyst in said heated reaction zone thereby converting at least a portion of said saturated $C_{1+}$ hydrocarbons into unsaturated $C_{2+}$ hydrocarbons and hydrogen In certain embodiments, the present invention provides a process for the non-oxidative conversion of saturated $C_{1+}$ hydrocarbons into unsaturated $C_{2+}$ hydrocarbons and hydrogen in the presence of an unsupported carbon-based catalyst, preferably having a carbon content of at least 90.0 wt %, preferably at least 92.0 wt %, preferably at least 95.0 wt %, preferably at least 97.0 wt %, preferably at least 99.0 wt %, preferably at least 99.5 wt %, preferably at least 99.9 wt % of carbon, with wt % based on the total weight of the carbon-based catalyst; and preferably having a metal concentration which is less than 0.3 wt %, preferably less than 0.3 wt %; preferably less than 0.2 wt %, preferably less than 0.1 wt %, preferably less than 0.05 wt %, preferably less than 0.03 wt %, preferably less than 0.01 wt %, preferably less than 0.005 wt %, based on the total weight of the carbon-based catalyst, Wherein the Process Comprises the Steps of:

a) supplying said carbon-based catalyst to a reaction zone, b) directly heating of said carbon-based catalyst contained in said reaction zone by means of induction heating thereby indirectly heating the reaction zone containing said carbon-based catalyst to a reaction temperature of at least 350° C.;

c) supplying a reaction gas comprising saturated $C_{1+}$ hydrocarbons to said heated reaction zone comprising said carbon-based catalyst; and d) subjecting said reaction gas to a non-oxidative conversion in the presence of said carbon-based catalyst in said heated reaction zone thereby converting at least a portion of said saturated $C_{1+}$ hydrocarbons into unsaturated $C_{2+}$ hydrocarbons and hydrogen.

In certain embodiments of the invention, a carbon-based catalyst as applied in the present process consists of (based on the weight of the catalyst):

(i) at least 95.0 wt %, preferably at least 97.0 wt %, more preferably at least 99.0 wt %, most preferably at least 99.5 wt % of carbon; with wt % based on the total weight of the carbon-based catalyst;

(ii) from 0 to 5.0 wt %, preferably from 0 to 1.0 wt %, more preferably from 0 to 0.5 wt %, most preferably from 0 to 0.1 wt % of inorganic oxide(s); with wt % based on the total weight of the carbon-based catalyst; and (iii) from 0 to 0.3 wt %, preferably from 0 to 0.1 wt %, more preferably from 0 to 0.01 wt %, most preferably from 0 to 0.001 wt % of metal, with wt % based on the total weight of the carbon-based catalyst.

In an example of an embodiments of the invention, a carbon-based catalyst as applied in the present process consists of (based on the weight of the catalyst):

(i) at least 99.0 wt %, preferably at least 99.5 wt % of carbon; with wt % based on the total weight of the carbon-based catalyst;

(ii) from 0 to 0.5 wt %, preferably from 0 to 0.1 wt % of inorganic oxide(s); with wt % based on the total weight of the carbon-based catalyst; and (iii) from 0 to 0.01 wt %, preferably from 0 to 0.001 wt % of metal, with wt % based on the total weight of the carbon-based catalyst.

In another example of an embodiments of the invention, a carbon-based catalyst as applied in the present process consists of (based on the weight of the catalyst):

(i) at least 99.0 wt %, preferably at least 99.5 wt % of carbon; with wt % based on the total weight of the carbon-based catalyst;

(ii) preferably from 0 to 0.01 wt %, preferably from 0 to 0.001 wt % of metal, with wt % based on the total weight of the carbon-based catalyst.

In some embodiments of the present invention, a carbon-based catalyst as used herein may be characterised in terms of how it resists electric current. The term "electric resistivity" refers to a parameter with Greek letter ρ, which is expressed as ohm-m at 20° C. A low resistivity indicates that a material readily allows electric current. In certain preferred embodiments, a carbon-based catalyst as used in the present invention has an electric resistivity comprised between $10^{-7}$ and $10^{2}$ ohm·m at 20° C. as determined by ASTM C611-98 (2016).

The term "electric conductivity" is the reciprocal of electrical resistivity and represents a material's ability to conduct electric current. It is commonly signified by the Greek letter σ, and is expressed as Siemens per metre (S/m).

A carbon-based catalyst as used in the present invention may have different morphologies. For instance, in certain embodiments, a carbon-based catalyst as used herein has a random morphology. In certain embodiments, a carbon-based catalyst as used herein has a fibrous shape, e.g. with aspect ratios of about 1000:1 (i.e. 10-100 nm wide×100-1,000,000 nm long).

In certain embodiments, a carbon-based catalyst as used herein has a spherical morphology, e.g. is provided as spherical particles, and has an average particle diameter of at least 0.1 μm, and preferably between 0.1 and 1000 μm; or between 1 and 1000 μm, as determined by SEM microscopy or by sieving according to ASTM D4513-11. For instance, a carbon-based catalyst as used herein is provided in the form of spherical particles having an average particle diameter from 0.25 to 1000 μm, or from 0.3 to 800 μm, or from 0.5 to 500 μm, or from 1 to 300 μm.

In certain embodiments, a carbon-based catalyst as used herein is characterised by its surface area. In a preferred embodiment, a carbon-based catalyst as used herein has a BET surface area, as determined by ASTM-D-3663 (2020) of at most 500 m²/g, or at most 200 m²/g, or at most 100 m²/g, or at most 50 m²/g, or at most 20 m²/g, or at most 15 m²/g, or at most 10 m²/g, or at most 5.0 m²/g. The BET surface area may be determined by $N_2$ adsorption techniques (ASTM D-3663-20, ASTM International, 2020). In an example, a carbon-based catalyst as used herein has a BET surface area of between 0.5 and 100 m²/g, and preferably between 1 and 20 m²/g, and more preferably between 1 to 10 m²/g.

In certain preferred embodiments, a carbon-based catalyst as used herein is non-porous. The term "non-porous" or "nonporous" as used herein refers to a carbon based catalyst that has a BET surface area of at most 5.0 m²/g, such as from 0.10 to 5.0 m²/g, or from 0.5 to 3.0 m²/g, or from 1.0 to 5.0 m²/g, or from 1.0 to 3.0 m²/g, as determined by ASTM-D-3663 (2020).

Another distinguishing feature of a carbon-based catalyst used in the present invention is that it is rich is defects, such as points, lines, interface and/or bulk defects. This feature may be determined by means of Raman spectroscopy. Raman spectroscopy is a well-known, rapid, and quantitative method of analysis that involves measuring the Raman effect or Raman scattering. Preferably a carbon-based catalyst as used herein is characterized by a Raman spectrum having at first peak (herein D peak or D band) at a wavenumber of about 1350 cm$^{-1}$, and a second peak (herein G peak or G band) at a wavenumber from about 1585 to about 1600 cm$^{-1}$. It is noted that the frequencies of the Raman spectrum mentioned above are given as Raman shifts abbreviated as cm$^{-1}$, thus, they are actually differential values between an excitation and a detected wavenumber. Raman spectra can be measured using a conventional laboratory Raman spectrometer (such as a Chromex Sentinel II fiber optic Raman spectrometer, a Horiba Jobin Yvon LabRAM spectrometer or a Horiba Jobin Yvon double or triple Raman spectrometer or a ThermoFisher Scientific ATmega XR Raman spectrometer or any other suitable Raman spectrometer than will provide substantially the same test results) under the conditions that include: an excitation wavelength of about 532 nanometres with an exciting laser power at the sample of about 100 mW. A Raman spectrometer should be capable of a spectral resolution of less than 2 nm/mm. In certain preferred embodiments, a carbon-based catalyst for use in the present invention is characterised by a Raman coefficient $I_D/I_G$ which is higher than 0.10, such as higher than 0.20, or higher than 0.30, wherein $I_D$ corresponds to the intensity of the Raman spectrum in said D peak; and $I_G$ corresponds to the intensity of the Raman spectrum in said G peak.

In certain preferred embodiments, a process of the invention may comprise the additional step of recovering at least a portion of the carbon-based catalyst from the reaction zone after step d) of a process, as described herein, thereby obtaining a graphite derivative.

The terms "graphite derivative" and "graphite-based compound" are used in the invention as synonyms and refer to the graphite compound that is obtained as side-product in a process of the invention, i.e. a carbon-based catalyst on which carbonaceous materials have been deposited. The "graphite derivative" may also be denoted herein as a "spent carbon-based catalyst" or a "modified carbon-based catalyst" or a "spent catalyst". It will be understood that the term "graphite derivative" as used herein refers to a graphite compound that contains the carbonaceous materials deposited thereon.

In certain preferred embodiments a process according to the invention may comprise the further step of subjecting the recovered graphite derivate to a mechanical treatment to reduce the size of the said graphite derivative.

The graphite derivative obtained in a process according to the invention can be used in further downstream processing, e.g. to make graphite or as a (carbon) catalyst.

One way to use the recovered graphite derivative is as a (carbon-based) catalyst. This is unexpected, as deposition of carbonaceous material on a catalyst applied during a non-oxidative hydrocarbon conversion process (e.g. dehydrogenation) is generally understood to deactivate the catalyst. The inventors have found that the graphite derivative obtained in a process of the invention retains relevant catalytic activity, despite the presence of coke material deposited thereon. Therefore, in some embodiments, a process according to the invention may comprise the further step of using at least a portion of the recovered graphite derivative as a carbon-based catalyst.

Preferably, a graphite derivative recovered in a process of the invention is applied as a carbon-based catalyst without prior treatment to remove carbonaceous material deposited thereon. In other words, in certain embodiments, it is not required to have an expensive, energy consuming (e.g. combustion), and/or polluting (e.g. resulting in unwanted CO and/or CO$_2$ emissions) treatment of the recovered graphite derivative. The present invention therefore beneficially adopts a closed production process which makes the operation easy, more cost effective, and avoids discharging (polluting) side reaction wastes in the whole process, such as e.g. CO and/or CO$_2$ emissions. The present invention allows resource recovery, cyclic utilization and environmental protection in the whole operation of the process.

In certain preferred embodiments, at least a portion of graphite derivative recovered in a process of the invention is applied as a carbon-based catalyst in a hydrocarbon conversion process, preferably in a non-oxidative hydrocarbon conversion process, and more preferably in a non-oxidative hydrocarbon conversion process for converting saturated $C_{1+}$ hydrocarbons into unsaturated $C_{2+}$ hydrocarbons and hydrogen. In a preferred embodiment, a process of the invention encompasses the further step of supplying recovered graphite precursor as a carbon-based catalyst in step a) of a process of the invention as described herein. It will be understood that in accordance with the invention, a graphite derivative as obtained in accordance with a process of the invention, is used as carbon-based catalyst provided that the deposited carbonaceous materials deposited thereon are not removed prior to its use.

By means of the present invention, an uncommon and effective process for producing a graphite derivative is provided, and at the same time the present processes also allow to overcome at least some of the drawbacks of a catalytic conversion, e.g. dehydrogenation, of saturated $C_{1+}$ hydrocarbons. The processes according to the present invention advantageously allows for a co-production of desired chemicals such as unsaturated $C_2+$ hydrocarbons, and hydrogen, and carbonaceous species, which can be directly valorised.

Another way to use the recovered graphite derivative is as a source for making graphite. In certain preferred embodiments, a process according to the invention may comprise the further step of processing the recovered graphite derivative, optionally mechanically pre-treated to reduce its size, into graphite. In other words, the present invention also relates to the use of a graphite derivative according to the invention, or obtained by a process according to the invention, for preparing graphite. Methods for preparing graphite starting from graphite derivatives are generally known in the art. For instance, graphite may be prepared starting from graphite derivative according to the invention by calcining/heating the graphite derivative to a temperature which is sufficiently high to produce graphite, e.g. to a temperature of at least 1200° C. or higher. A great advantage of the present invention is that it provides a way to produce a graphite derivative, and thus to produce graphite starting from "wastes" containing carbonaceous materials, i.e. here from a side-product in a non-oxidative hydrogenation reaction.

In another aspect, the invention also relates to a graphite derivative obtained or obtainable by a process as defined herein. A graphite derivative as obtained in the present processes may be characterised by a number of features, such as e.g. improved morphology, high electro-resistivity, improved composition, including a higher purity and limited levels of contaminants such as inorganic (e.g. Si, Al) or metallic (e.g. Ni, Mo, etc) contaminants.

In some embodiments, said graphite derivative comprises a carbon-containing material (as defined herein above) selected from the group consisting of graphite (G), carbon felt (CF), graphite felt (GF), expanded graphite (EG), carbon nanofiber (CNF), carbon nanotubes (CNTs), graphite fabric, graphite cloth, graphene, few-layer graphene (FLG), and any combinations thereof, and preferably a carbon-containing material selected from expanded graphite, graphite, or a combination thereof.

In some embodiments, said graphite derivative is substantially metal-free, (as defined hereinabove), and preferably has a metal concentration which is less than 3000 ppm, or less than 2000 ppm, or less than 1000 ppm. In a preferred embodiment, a graphite derivative according to the invention has a metal concentration which is less than 3000 ppm, or less than 2000 ppm, or less than 1000 ppm. In certain preferred embodiments, a graphite derivative according to the invention is free of any metal (as defined herein above). Metal content of a graphite derivative as provided herein may be determined by the same techniques as mentioned above for the carbon-based catalyst.

In a preferred embodiment, a graphite derivative according to the invention has a Si content which is less than 2000 ppm, or less than 1800 ppm, or less than 1500 ppm. In certain preferred embodiments, a graphite derivative according to the invention is free of Si.

In a preferred embodiment, a graphite derivative according to the invention has an Al content which is less than 2000 ppm, or less than 1500 ppm, or less than 1000 ppm, or less than 800 ppm, or less than 500 ppm. In certain preferred embodiments, a graphite derivative according to the invention is free of Al.

In a preferred embodiment, a graphite derivative according to the present invention comprises, preferably consists of non-porous material. In a preferred embodiment, a graphite derivative according to the present invention comprises, preferably consists of non-porous material, with non-porous as defined herein.

In some embodiments, said graphite derivative has a bulk density of between 2.00 and 2.25 g/cm$^3$, as determined by ASTM C-559-16 (2020). The bulk (or apparent) density (D) refers to the ratio of mass (m) to its volume (V) of the graphite derivative (D=m/V).

In some embodiments, said graphite derivative is characterised by a Raman spectrum, as determined by Raman Spectroscopy using an excitation wavelength of about 532 nm and exciting laser power of about 100 milliwatt (mW); showing a first peak (D peak) at a wavenumber of about 1350 cm$^{-1}$ and a second peak (G peak) at a wavenumber from about 1585 to about 1600 cm$^{-1}$, and wherein said carbon-based catalyst has a Raman coefficient $I_D/I_G$ which is higher than 0.10, such as higher than 0.20, or higher than 0.30, wherein $I_D$ corresponds to the intensity of the Raman spectrum in said D peak; and $I_G$ corresponds to the intensity of the Raman spectrum in said G peak.

In some embodiments, said graphite derivative has a BET surface area of at most 500 m$^2$/g, or at most 200 m$^2$/g, or at most 50 m$^2$/g, or at most 20 m$^2$/g, or at most 15 m$^2$/g, or at most 10 m$^2$/g, as determined by ASTM-D-3663 (2020).

In some embodiments, said graphite derivative according to the present invention may also be characterised in terms of how it resists electric current. In a preferred embodiment, a graphite derivative of the present invention has an electric resistivity of between 10$^{-7}$ and 10$^2$ ohm·m at 20° C. as determined by ASTM C611-98 (2016).

In some embodiments, said graphite derivative comprises more than on layers of carbon-containing material, and preferably from 2 to 50 layers of carbon-containing material. The presence of different layers of carbon material and thickness thereof in a graphite derivative may be measured using techniques known in the art, such as by means of Scanning electron microscopy (SEM). For instance, the thickness of deposited carbon layers on the original catalyst can measured through subtraction of (i) SEM measurement of the layer thickness before from (ii) SEM measurement of the layer thickness after the process.

By means of the present invention, an uncommon and effective process for the catalytic conversion, e.g. dehydrogenation, of saturated hydrocarbons is provided which at the same time allows to produce a graphite derivative is provided. Processes according to the present invention hence advantageously allow for a co-production of desired chemicals such as $C_{2}$+ (unsaturated) hydrocarbons, and hydrogen, and carbonaceous materials (carbonaceous species), which can be directly valorised. Processes according to the invention is also characterised by an improved carbon efficiency and high energy efficiency, especially since a graphite derivative can be readily obtained as a side stream in a non-oxidative hydrocarbon conversion processes as defined herein.

The present invention further provides a system for a non-oxidative conversion reaction of saturated $C_{1+}$ hydrocarbons into unsaturated $C_{2+}$ hydrocarbons and hydrogen, wherein the system comprises:

at least one reaction zone configured to receive a carbon-based catalyst (as defined herein), at least one inlet line for feeding a reaction gas (as defined herein) comprising saturated $C_{1+}$ hydrocarbons into said reaction zone;

at least one flow controlling means for controlling reaction gas flow rate to the reaction zone;

at least one outlet line for recovering a reacted product stream comprising unsaturated $C_{2+}$ hydrocarbons and hydrogen from said reaction zone, and at least one induction heating device configured for inductively heating a carbon-based catalyst contained within a reaction zone to a reaction temperature effective for the non-oxidative conversion of saturated $C_{1+}$ hydrocarbons into unsaturated $C_{2+}$ hydrocarbons and hydrogen in the presence of said carbon-based catalyst;

at least one temperature setting device for regulating the set temperature of the reaction;

optionally, at least one temperature measuring device for determining the reaction temperature, and optionally, at least one heating device for pre-heating the reaction gas before entering said reaction zone;

optionally at least one recovery unit for recovering at least a portion of the carbon-based catalyst spent during said non-oxidative conversion from said reaction zone.

The Present Invention Also Provides a System for Producing a Graphite Derivative, Wherein the System Comprises:

at least one reaction zone configured to receive a carbon-based catalyst (as defined herein), at least one inlet line for feeding a reaction gas (as defined herein) comprising saturated $C_{1+}$ hydrocarbons into said reaction zone;

at least one flow controlling means for controlling reaction gas flow rate to the reaction zone;

at least one outlet line for recovering a reacted product stream comprising unsaturated $C_{2+}$ hydrocarbons and hydrogen from said reaction zone, and at least one induction heating device configured for inductively heating a carbon-based catalyst contained within a reaction zone to a reaction temperature effective for the non-oxidative conversion of saturated $C_{1+}$ hydrocarbons into unsaturated $C_{2+}$ hydrocarbons and hydrogen in the presence of said carbon-based catalyst;

at least one temperature setting device for regulating the set temperature of the reaction;

optionally, at least one temperature measuring device for determining the reaction temperature, and optionally, at least one heating device for pre-heating the reaction gas before entering said reaction zone;

optionally at least one recovery unit for recovering at least a portion of the carbon-based catalyst spent during said non-oxidative conversion from said reaction zone.

For example, an induction heating device (herein also "induction heater") may be advantageously configured to directly heat the carbon-based catalyst provided within the reaction zone. The induction heating device (induction heater) may for instance extend around a portion of the exterior surface of the reaction zone. The heat from the carbon-based catalyst (acting as susceptor) can advantageously be used to directly heat the reaction gas within the reaction zone. Direct heating of reaction gas within the reaction zone is energetically efficient and allows great control over the rate at which the gas within the reaction zone is heated.

In preferred embodiments of a system as provided herein, said induction heating device comprises at least one induction coil defining a space provided within said induction coil capable of receiving said carbon-based catalyst, and an AC power supply electrically connected to said induction coil and capable of supplying an alternating current having a suitable frequency to said induction coil, such as a frequency alternating between 2 and 500 kHz.

Preferably, the induction heater includes an induction coil which is arranged to be powered by a power source supplying alternating current and which is positioned to generate an alternating magnetic field within the reactor zone upon energization by the power source, whereby the catalyst material is heated to a given temperature by means of said alternating magnetic field. The induction coil can for instance be placed around the reaction zone. An induction heating device for use in the invention may be configured to provide an alternating current having a frequency of at least 2 Khz. The induction heating device may be configured to provide an alternating current having a frequency of up to 0.5 MHz. Preferably, the induction heater may be configured to provide an alternating current between 2 and 500 kHz. The frequency of the alternating current provided by the induction heater is advantageously selected to facilitate uniform and localised heating of the carbon-based catalyst material within the reaction zone in order to obtain a highly efficient process.

In an example, an induction heater (e.g. Power Cube 45/400 industrial LINE HI-PE, 3.5 kW, CEIA international) is constituted by a spiral 4-turn induction coil (length=0.90 m, pure coil resistance=$2.066 \times 10^3 \Omega$), cooled by means of water circulation. A reactor containing the carbon-based catalyst can be housed inside the induction heater coils and temperature real-time control/regulation can be ensured by a manager unit (e.g. CEIA Master controller V3+ unit) connected to a laser pyrometer (e.g. CEIA SH15/SLE, diameter laser beam: about 1-5 mm, power <1 mW, located at about 24 cm from the carbon-based catalyst) shot up on the catalyst bed, and working in the 120-900° C. range (accuracy ±1° C.). The heating/cooling rate allowed for the system is for instance 60-80° C. $min^{-1}$ in the operational temperature range. The catalyst may for instance be housed in a quartz tubular reactor (e.g. inner diameter of 22 mm, length of 600 mm) between quartz wool plugs to ensure the homogeneous flow distribution. The reactor can then be purged with an inert gas, e.g. a pure argon flow at room temperature for 30 minutes, and then the inert gas flow is replaced by the reaction gas. The exit line can be heated with heating tape maintained at e.g. 150° C. to prevent condensation of heavy products before the gas chromatography analyser.

As indicated hereinabove, a reaction zone may be an individual reactor, or a reactor may comprise reaction zones in series or in parallel. Any reactor configured to allow the contact of a reaction gas with the carbon-based catalyst provided in said reaction zone/reactor may be used. For example, reactors with a fixed bed or moving bed may be applied.

A system according to the invention may also comprises a temperature measuring device capable of measuring the reaction temperature within the reaction zone, for instance at different points of the catalyst bed, such as a thermocouple.

In another example said temperature measuring device comprises a device capable of measuring the temperature at the outer surface of the reaction zone, such as for instance a laser pyrometer.

A system according to the invention may further comprise a heating device for pre-heating the reaction gas before entering said reaction zone.

A system according to the invention may further comprise a recovery unit for recovering at least a portion of the carbon-based catalyst spent during said non-oxidative conversion from said reaction zone. Such recovery unit may comprise means for mechanically reducing the size of a graphite derivate recovered in a system according to the invention. The following examples serve to merely illustrate the invention and should not be construed as limiting its scope in any way. While the invention has been shown in only some of its forms, it should be apparent to those skilled in the art that it is not so limited, but is susceptible to various changes and modifications without departing from the scope of the invention.

EXAMPLES

Materials

The following carbon-based catalysts were applied as carbon-based catalysts in the below reported examples:

Graphite felt (denoted as "GF" in the example section) was obtained from Mersen SA. Prior to the catalytic reaction, the graphite felt (GF) was cut into the form of disks (diameter×thickness of 28×6 mm, 0.37 g). This felt consists of randomly organized microfilaments with an external diameter of about 10 μm.

Graphite Felt 2 (denoted as "GF2" or "new GF" in the example section herein), is commercially available as "GFA 10" and was obtained from Final Advanced Materials Sarl.

Graphite (denoted as "G" in the example section) used in the present examples is commercially available from Merck.

Expanded graphite (denoted as "EG" in the example section) used in the present examples is commercially available from Mersen SA.

A carbon nanofiber/graphite felt (denoted as "CNF/GF" in the example section) was prepared following the reaction and the reaction conditions as shown in FIG. 1. First, Ni supported on graphite felt (GF: see above) was synthesized by impregnation with 2 wt. % of nickel nitrate. Ni is introduced through impregnation. Next, a carbon nanofiber was grown on the impregnated graphite felt via chemical vapor deposition using ethane as carbon source. The resulting sample was treated (washed) with nitric acid to remove traces of nickel.

Methods

Catalyst morphology: the morphology of a sample of a carbon-based catalyst can be explored by utilizing Scanning electron microscopy (SEM) (ZEISS GeminiSEM 500 microscope with a resolution of 5 nm) according to techniques well known in the art. A sample of carbon-based catalyst is deposited onto a double face graphite tape in order to avoid charging effect problems during the analysis.

Catalyst average particle diameter can be determined by scanning electron microscopy (SEM) (ZEISS GeminiSEM 500 microscope with a resolution of 5 nm) according to techniques well known in the art or as by sieving according to ASTM D4513-11.

Catalyst surface area is determined according to ASTM-D-3663 (2020). The specific surface area of a sample of a carbon-based catalyst can be calculated from the nitrogen isotherm using the BET method and t-plot method, respectively. The latter was performed on a ASAP2420 (Micromeritics) using $N_2$ adsorption at 77 K. Before the $N_2$ adsorption, samples are heated at 250° C. for 3 h under dynamic vacuum to desorb surface impurities.

The level of defects, such as points, lines, interfaces and/or bulk defects, of a carbon-based catalyst or graphite derivative according to the invention was determined using Raman spectroscopy. The Raman spectra were recorded using a LabRAM ARAMIS Horiba Raman spectrometer equipped with a Peltier cooled CCD detector. A laser line (532 nm/100 mW (YAG) with Laser Quantum MPC600 PSU) was used to excite the catalyst sample.

Electric-resistivity (in ohm·m) of a carbon-based catalyst or graphite derivative at room temperature (20° C.) according to the invention is determined according to ASTM C611-98(2016).

Density of the carbonaceous species/graphite derivative may be determined as defined in by ASTM-C559-16 (2020).

X-ray diffraction analyses (XRD) were done according to methods that are known in the art, and using e.g., using a Bruker advanced D8 analyser.

Thermogravimetric analyses (TGA) were performed under air (25 mL/min) on a TGA Q5000 Sorption Analyzer (TA Instrument). The temperature was raised to 1000° C. at a heating rate of 10° C./min.

Temperature-programmed reduction of hydrogen ($H_2$-TPR) was conducted on a Micromeritics ASAP-2100 setup equipped with a multichannel mass spectrometer (Thermo-Star™ GSD 301 T (Pfeiffer Vacuum)). In a typical procedure, 50 mg of the sample was heated for 1 h at 130° C. under an Ar-stream, and then cooled to room temperature. Next, the stream was switched from Ar to a 10% $H_2$/Ar mixture (50 mL/min), while increasing the sample temperature at a rate of 10° C./min. The evolved species were monitored through the intensities of m/z=2 ($H_2$).

Determination of specific hydrocarbons: detection of acetylene and ethylene was conducted by connecting the reactor outlet to a multichannel mass spectrometer (ThermoStar™ GSD 301 T (Pfeiffer Vacuum)). The outlet gas was monitored with intensities of m/z 26 ($C_2H_2$) and m/z 28 ($C_2H_4$).

Reactor Set-Up with Induction Heater Coil

In the below given examples, the reaction was carried out in a tubular quartz reactor with an inner diameter of 24 mm and a length of 800 mm. The non-isolated quartz reactor containing the catalyst was placed inside an induction heater coil with an inner diameter of 34 mm. The temperature of the set-up was monitored and controlled with a laser pyrometer, aimed on the outside of the reactor. The induction heating device with laser pyrometer (Master Controller V3+ and Power Cube 45/900) was purchased from CEIA Ltd. All gas flows were controlled using Brooks 5850TR mass flow controllers. The reactions were carried out at a reference condition of 700° C. with a total flow set to 25 ml/min of $CH_4$/Ar (1:1), unless differently specified. Because the density of the different carbon-based catalysts used was not the same, the catalyst volume was kept constant. Therefore, the WHSV (weight of feed flowing per unit weight of the catalyst per hour) of each sample was different. For this, catalyst weight is measured prior to catalyst loading and flow is determined by mass flow controllers. The reactor outlet lines were kept at 150° C. to prevent the condensation of naphthalene.

The reaction products were analysed on-line by thermal conductivity detector (TCD) and flame ionization detector (FID) with a gas chromatography (GC Varian 3800 equipped with DP-1 and Carbobond capillary columns). The Dietz factor method was used for the calculation of gas concentration by FID. A soap film flowmeter was used to measure the gas flow rate. Because the selected GC column cannot separate acetylene and ethylene, only the selectivity and yield of the sum of acetylene and ethylene ($C_2H_2$+$C_2H_4$) can be obtained.

Figure 2:
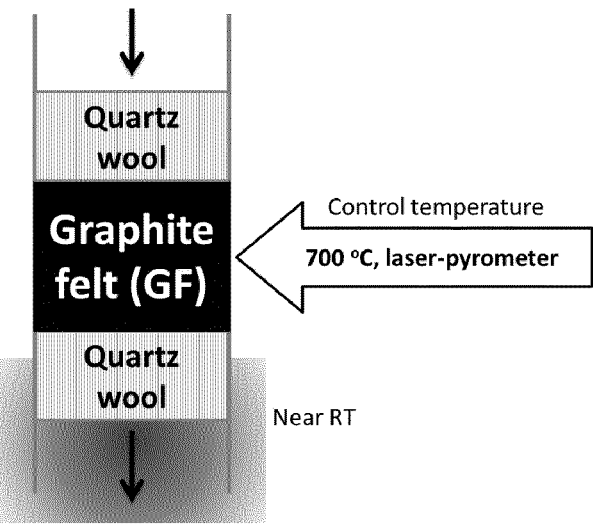
FIG. 2 provides a schematic illustration of an embodiment of a catalytic reactor based on graphite felt as carbon-based catalyst and using induction heating to heat the catalyst. The graphite felt may be heated by an electromagnetic induction heating device, while exposed to a methane-rich stream.

FIG. 2 provides a schematic illustration of the set-up of a catalytic reactor as used in examples 1 to 11. In this figure, a graphite felt is applied as carbon-based catalyst and induction heating is used to heat the catalyst.

Conversion Yields

Methane conversion ($X_{CH4}$), product i selectivity ($S_i$), product i yield ($Y_i$), hydrogen yield ($Y_{H2}$) and carbon balance were calculated according to the following equations (1)-(5):

$$X_{CH_4} = \frac{F_{CH_4,in} - F_{CH_4,out}}{F_{CH_4,in}} \times 100\% \quad (1)$$

$$S_i = \frac{n_i \times F_{i,out}}{F_{CH_4,in} - F_{CH_4,out}} \times 100\% \quad (2)$$

$$Y_i = \frac{n_i \times F_{i,out}}{F_{CH_4,in}} \times 100\% \quad (3)$$

$$Y_{H_2} = \frac{2 \times F_{H_2,out}}{4 \times F_{CH_4,in}} \times 100\% \quad (4)$$

$$\text{Carbon balance} = \frac{F_{CH_4,out} + 2 \times F_{C_2H_2 + C_2H_4,out} + 6 \times F_{C_6H_6,out} + 7 \times F_{C_7H_8,out} + 10 \times F_{C_{10}H_8,out}}{F_{CH_4,in}} \times 100\% \quad (5)$$

wherein $F_{CH4,in/out}$ is the flow rate of $CH_4$ in the feed or effluent, $F_{i,out}$ is the flow rate of product i in the effluent, $n_i$ is the carbon number of the product i.

In the below description, methane ($CH_4$) conversion and benzene ($C_6H_6$) selectivity are used as examples to explain the application of the above calculation equations:

Where C is the concentration of molar, A is the area of GC, Df is the Dietz factor, F is the flow rate (mL/min).

Step 1. Molar Concentration of Inlet $CH_4$ ($C_{CH4,inlet}$)

$$C_{CH4,TCD,inlet} = \frac{A_{CH4,TCD,inlet}}{A_{CH4,100\%,TCD}} \times 1$$

$$C_{CH4,FID,inlet} = \frac{A_{CH4,FID,inlet}}{A_{CH4,100\%,FID}} \times 1$$

$$C_{CH4,inlet} = \frac{1}{2} \times (C_{CH4,TCD,inlet} + C_{CH4,FID,inlet})$$

Step 2. Molar Concentration of Outlet $CH_4$ ($C_{CH4,outlet}$)

$$C_{CH4,TCD,outlet} = \frac{A_{CH4,TCD,outlet}}{A_{CH4,100\%,TCD}} \times 1$$

$$C_{CH4,FID,outlet} = \frac{A_{CH4,FID,outlet}}{A_{CH4,100\%,FID}} \times 1$$

$$C_{CH4,outlet} = \frac{1}{2} \times (C_{CH4,TCD,outlet} + C_{CH4,FID,outlet})$$

Step 3. Molar Concentration of Outlet $C_6H_6$($C_{C6H6,outlet}$)

$$\because C_i = \frac{\dfrac{A_i}{Df_i \times M_i}}{\sum_j \dfrac{A_i}{Df_j \times M_j}}$$

$$\therefore \frac{C_{C6H6,outlet}}{C_{CH4,outlet}} = \frac{\dfrac{A_{C6H6}}{Df_{C6H6} \times M_{C6H6}}}{\dfrac{A_{CH4}}{Df_{CH4} \times M_{CH4}}} = \frac{A_{C6H6,FID,outlet}}{A_{CH4,FID,outlet}} \times \frac{Df_{CH4} \times M_{CH4}}{Df_{C6H6} \times M_{C6H6}}$$

$$\therefore C_{C6H6,outlet=} \frac{A_{C6H6,FID,outlet}}{A_{CH4,FID,outlet}} \times \frac{Df_{CH4} \times M_{CH4}}{Df_{C6H6} \times M_{C6H6}} \times C_{CH4,outlet}$$

Step 4. Flow rate of inlet and outlet $CH_4$ and outlet $C_6H_6$ ($F_{CH4,inlet}$, $F_{CH4,outlet}$, $F_{C6H6,outlet}$)

$$F_{CH4,inlet} = F_{inlet} \times C_{CH4,inlet}$$

$$F_{CH4,outlet} = F_{outlet} \times C_{CH4,outlet}$$

$$F_{C6H6,outlet} = F_{outlet} \times C_{C6H6,outlet}$$

Step 5. $CH_4$ Conversion ($X_{CH4}$) and $C_6H_6$ Selectivity ($S_{C6H6}$)

$$X_{CH4} = \frac{F_{CH4,inlet} - F_{CH4,outlet}}{F_{CH4,inlet}} \times 100\%$$

$$S_{C6H6} = \frac{F_{C6H6,outlet} \times 6}{F_{CH4,inlet} - F_{CH4,outlet}} \times 100\%$$

Below examples report the catalytic non-oxidative conversion of hydrocarbons in a reaction gas containing methane carried out in the presence of a carbon-based catalyst as defined herein.

Example 1: Non-Oxidative Conversion of Methane Using a Graphite Felt as Carbon-Based Catalyst In this example, the catalytic conversion process was carried out in the presence of a graphite felt (see material section above, 0.37 g GF) as carbon-based catalyst. The graphite felt was heated by means of an electromagnetic induction heating device, while exposed to a methane-rich stream.

Catalytic conversion of methane was carried out in tubular quartz reactor as explained in the method section above, and schematically illustrated in FIG. 2. In this example, reactions were carried out with a total flow set to 25 ml/min of $CH_4$/Ar (1:1) at a reaction pressure of 0.1 MPa. Different reaction temperatures and WHSV conditions were tested as explained below.

Figure 3:
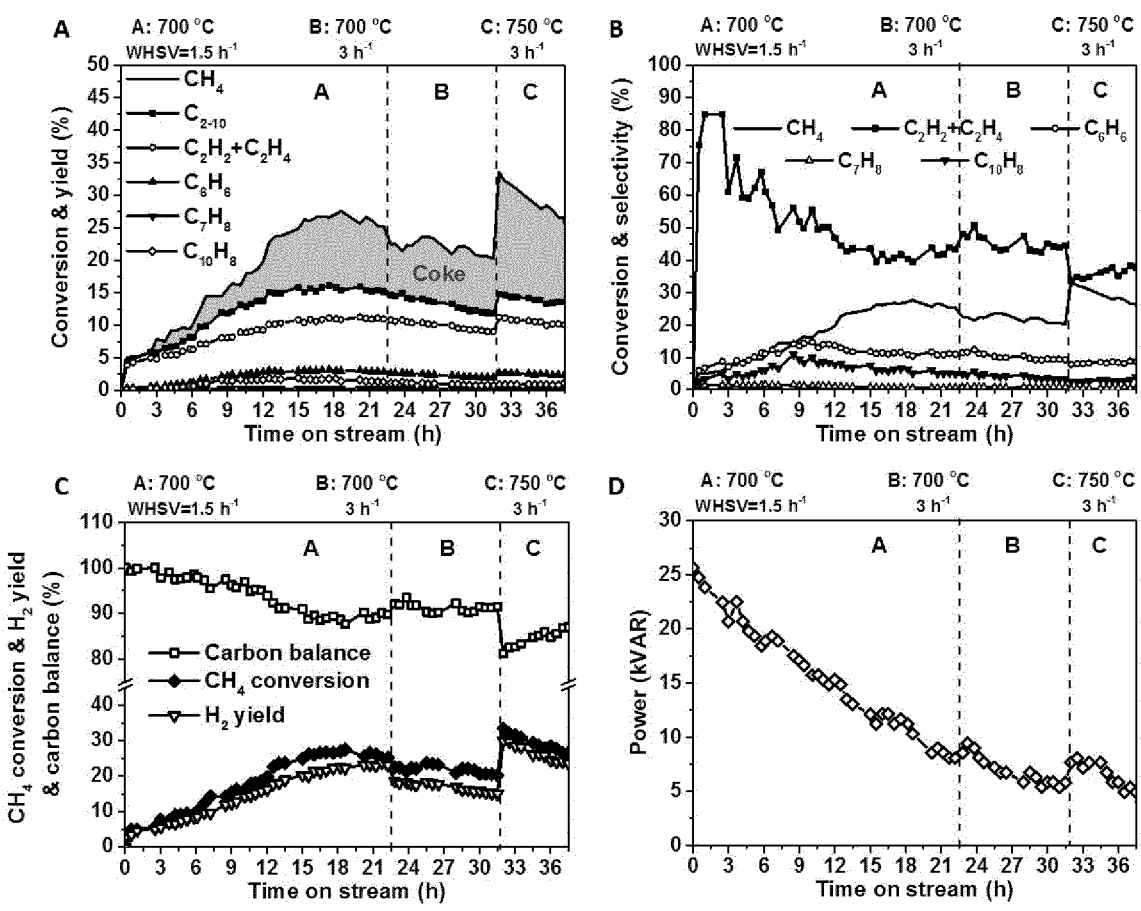

The methane conversion reaction performance on the graphite felt catalyst as a function of time on stream under different reaction conditions is displayed in FIG. 3. FIG. 3 represents product yield (FIG. 3A), product selectivity (FIG. 3B), carbon balance and hydrogen yield (FIG. 3C), and power supplied by induction heating device with time on stream on graphite felt (FIG. 3D). The difference between methane conversion and the sum of all hydrocarbon yields ($C_{2-10}$) represents the yield of coke species deposited on the catalyst surface.

FIG. 3A shows that the conversion reaction was first carried out at 700° C. and 25 mL/min gas flow (WHSV=1.5 $h^{-1}$). There was an induction period in which the methane conversion kept rising until it reached a stable level after about 15 h. Almost no apparent deactivation was observed up to about 22 h of test (part A in FIG. 3). At this point the reactant flow rate was doubled from 25 mL/min to 50 mL/min (WHSV=3 $h^{-1}$) keeping other reaction conditions similar (part B in FIG. 3). The methane conversion was slightly decreased from 27% to ca. 23% and remained almost stable during the period of test from 22 to 31 h. Increasing the reaction temperature from 700 to 750° C. lead to a significant increase of the methane conversion from 23% to about 35% along with a slight increase of hydrocarbon products (part C in FIG. 3).

The reactants including unsaturated $C_2$ hydrocarbons (ethylene and acetylene), benzene, toluene and naphthalene were formed on graphite felt during the conversion reaction. As shown in FIG. 3A, the order of product yield was as follows: $C_2$ hydrocarbons>benzene>naphthalene>toluene.

The difference between methane conversion and the sum of all hydrocarbon yields ($C_{2-10}$) represents the yield of coke formation (FIG. 3A), which was generated from the side reaction of direct methane decomposition into hydrogen and carbonaceous species. At the beginning of the reaction at 700° C., deposition of carbonaceous species increased until it stabilized. Deposition decreased under high gas flow rate. At 750° C., coke yield increased considerably at the beginning of the reaction and then reduced.

Product selectivity is shown in FIG. 3B. This figure shows that reaction selectivity of acetylene ($C_2H_2$) and ethylene ($C_2H_4$) was higher than that of aromatic compounds. Ethylene and acetylene are the primary product of the methane conversion. The benzene selectivity was higher than naphthalene while that of toluene was the lowest. Under the reaction condition of 700° C. and 25 mL/min (WHSV=1.5 $h^{-1}$) the selectivity of acetylene and ethylene initially decreased and then stabilized after 15 h, while the selectivity of aromatic compounds increased until it was stable at about 15 h. When the gas flow rate was doubled to 50 mL/min (WHSV=3 $h^{-1}$) methane molecules converted per unit of time were increased. At 750° C., despite the increased conversion, selectivity of acetylene and ethylene slightly decreased, and at the same time there was a slight decline in aromatic selectivity.

The present example illustrates a selectivity towards $C_2$ hydrocarbons as conversion products as in this example the main conversion products are ethylene and acetylene, while aromatics are retrieved in a relatively low fraction.

As shown in FIG. 3C, the change of conversion was accompanied with the opposite variation of carbon balance under different reaction conditions, indicating a considerable contribution of side reaction in the methane conversion. Meanwhile the variation of hydrogen yield was similar to that of conversion. Power supplied by the induction heating device decreased with time on stream (FIG. 3D).

At a temperature of 700° C., influence of the flow rate was relatively low. This can be attributed to the heating properties of the inductive mode as only the solid catalyst was maintained at the reaction temperature, while no pre-heating of the reactant gaseous products was necessary. Increasing the reaction temperature from 700 to 750° C. led to an increase of methane conversion, and a direct decomposition reaction became predominant, i.e. large rise in carbon deposition.

Summarised, the above example shows that the use of a graphite felt as carbon-based catalyst presented a high catalytic activity and selectivity towards $C_2$ products. The example also demonstrates the formation of carbonaceous species during the conversion reaction, and the deposition thereof on the carbon-based catalyst, yielding a graphite derivative

Example 2: Analysis of the Graphite Derivative Obtained by the Catalytic Reaction of Example 1

In this example, characteristics and morphology of the graphite felt catalyst, before and after (i.e. yielding the graphite derivative) catalytic methane conversion reaction as carried out in example 1, were analysed using different techniques.

Figure 4:
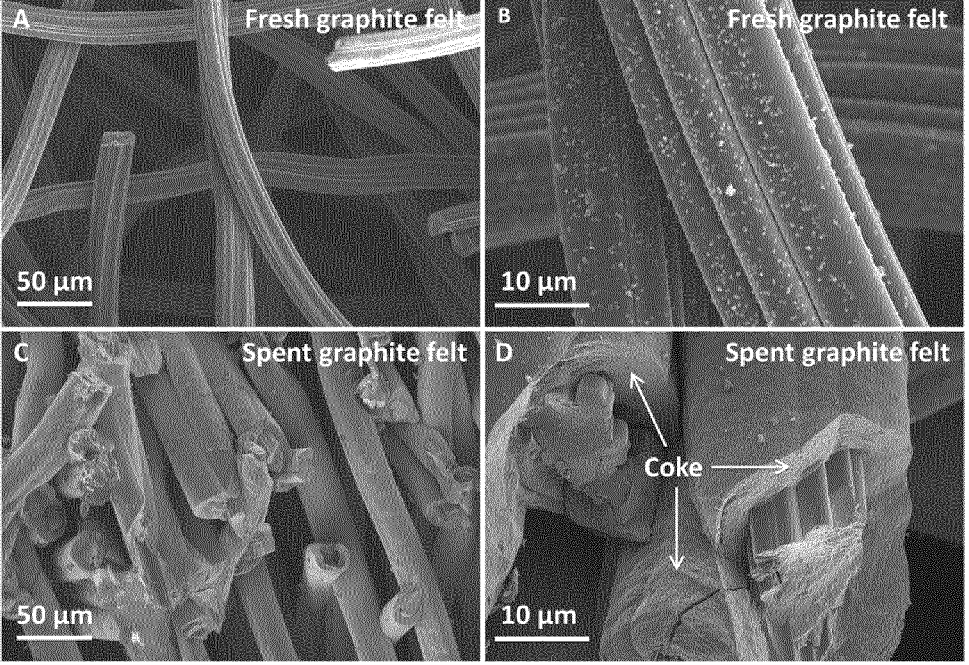
FIG. 4 represents SEM analyses performed on a carbon-based catalyst before (A and B: fresh graphite felt catalyst) and after (C and D: spent graphite felt catalyst) used in the catalytic conversion reaction of example 1.

FIG. 4 represents SEM analyses performed on the graphite felt carbon-based catalyst before (A and B: carbon-based catalyst; fresh graphite felt catalyst) and after (C and D: graphite derivative; spent graphite felt catalyst) used in the above described catalytic conversion reaction. High-resolution SEM micrograph (FIG. 4D) clearly shows the formation of a relatively thick (1 µm) encapsulating carbon layer around the pristine graphite felt microfilaments (indicated by arrows). The carbon layer is formed with a very close interface with the pristine filaments. According to the SEM micrograph (FIG. 4C) a relatively large part of the graphite felt filaments was covered.

Figure 5:
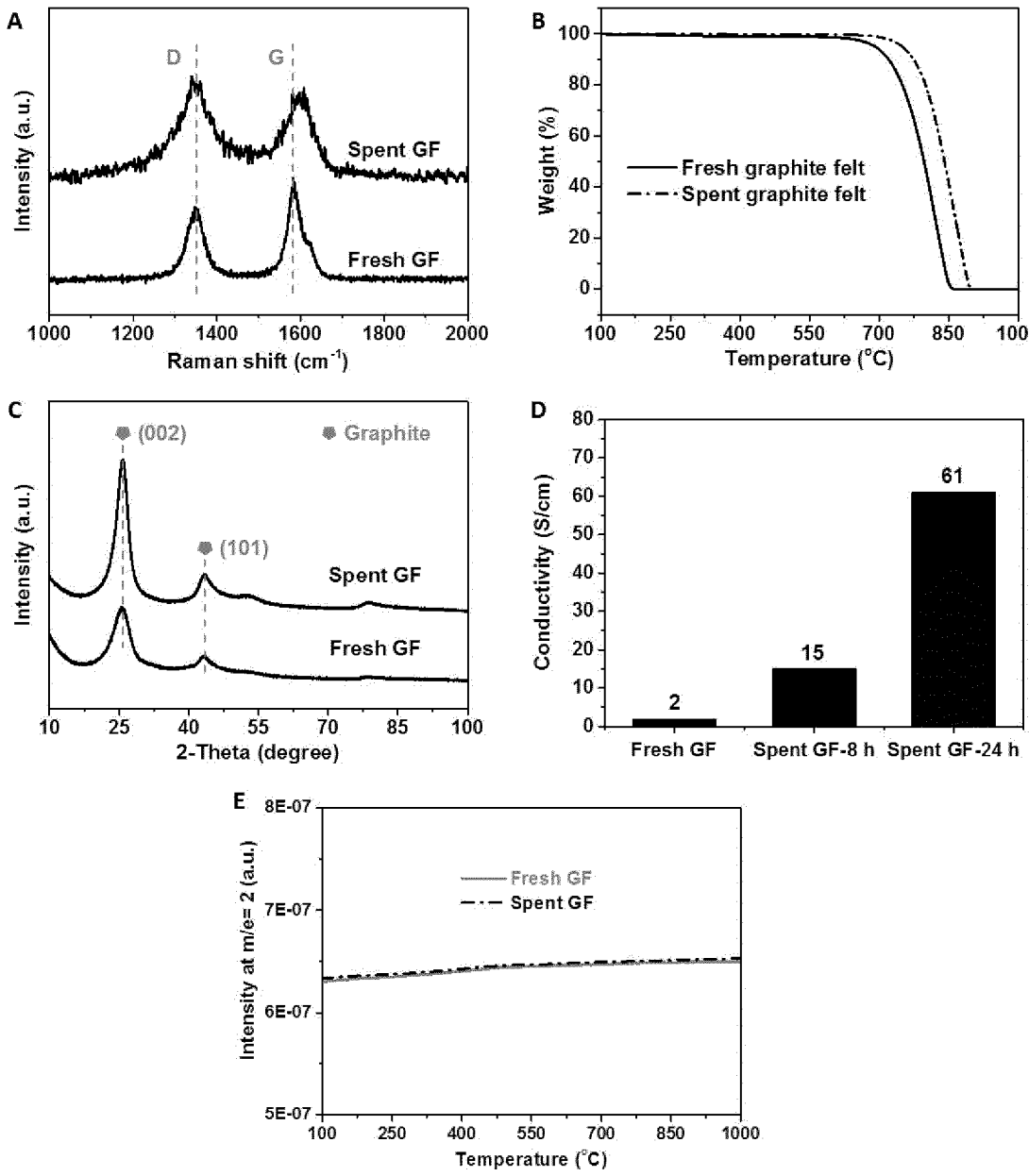
FIG. 5 represents the results of different analyses performed on a carbon-based catalyst before (fresh graphite felt catalyst) and after (spent graphite felt catalyst) used in the catalytic conversion reaction of example 1, including Raman spectrometry (FIG. 5A); thermogravimetric analyses (TG) (FIG. 5B), X-ray diffraction analysis (XRD) (FIG. 5C), conductivity testing (FIG. 5D) and temperature-programmed reduction of hydrogen ($H_2$-TPR) (FIG. 5E).

FIG. 5 represents the results of Raman spectrometry (FIG. 5A); thermogravimetric analyses (TG) (FIG. 5B), X-ray diffraction analyses (XRD) (FIG. 5C), conductivity testing (FIG. 5D) and temperature-programmed reduction of hydrogen ($H_2$-TPR) (FIG. 5E) performed on the graphite felt carbon-based catalyst before (fresh catalyst) and after (graphite derivative, spent catalyst) used in the catalytic conversion reaction of example 1. The analyses were carried as indicated in the method section above.

Raman spectroscopy was performed to investigate the change in the graphitic structure of GF after the conversion process. Results thereof are represented in FIG. 5A. As shown in FIG. 5A, both fresh GF and spent GF showed two bands corresponding to the different carbonaceous structures: the G band is attributed to an ideal graphitic lattice at around 1580 cm$^{-1}$ and the D band (about 1350 cm$^{-1}$) is associated with the structural defects. After the conversion reaction, the intensity of D band on spent GF was increased and the G band of spent GF shifted to a higher wavenumber compared to that of fresh GF. These results can be attributed to the coke, with more defects and disordered graphitic fragments inside the spent sample. The Raman coefficients $I_D/I_G$ retrieved for the fresh and spent GF catalyst were respectively: 0.71 (fresh) and 1.25 (spent).

As shown in FIG. 5B, thermogravimetric analysis (TG) showed a weight loss which occurred on the fresh as well as on the spent graphite felt catalyst. Weight loss temperature of the spent catalyst was higher than the weight loss of the fresh catalyst, indicating that carbon deposition, which decreased the surface area of spent GF, resulted in an increased thermal stability of the catalyst after the methane conversion reaction.

FIG. 5C presents X-ray diffraction patterns of the fresh and spent graphite felt applied in example 1. FIG. 5D represents results of conductivity analyses. Conductivity of fresh graphite felt was 2 S/cm (Siemens/cm), while after 8 h of conversion reaction, conductivity of the catalyst increased to 15 S/cm as shown in FIG. 5D. Moreover, after 24 h of reaction, conductivity of spent GF catalyst increased to 61 S/cm. These results confirm that coke formation during the conversion reaction increased the conductivity of graphite felt with time on stream. A $H_2$-TPR analysis is shown in FIG. 5E. Results for fresh and spent graphite felt were similar, hence there was negligible $H_2$ adsorption or desorption on the fresh or spent graphite felt.

Summarised, the present example demonstrates deposition of carbonaceous species, formed during a methane conversion reaction as described in the present invention, on the carbon-based catalyst used in the conversion process, thereby forming a graphite derivative.

Example 3: Coke Deposition on Carbon-Based Catalyst

In this example, a blank reaction (no methane) was carried out in the same catalytic reactor and using the same graphite felt (0.37 g) catalyst as described in example 1 to test the power supplied by the induction heating device. The reaction was carried out under pure Ar gas stream at a temperature of 700° C., a pressure of 0.1 MPa, and Ar gas flow rate of 25 ml/min.

Figure 6:
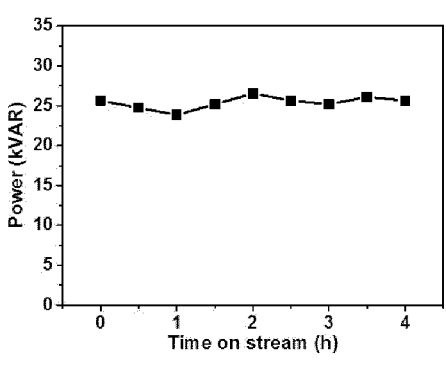
FIG. 6 shows the results of a power test carried out during a blank example (reaction without methane) run using induction heating on graphite felt according to example 3. Conditions were as follows: Induction heating, 700° C., 0.1 MPa, 25 mL/min Ar and 0.37 g GF.

Results of the power test are represented in FIG. 6. As shown in FIG. 6, the blank reaction showed negligible power change with time on stream. The decreased power during the reaction (see FIG. 3D above) can be attributed to coke formation on the graphite felt catalyst, which increased catalyst conductivity.

Example 4: Non-Oxidative Conversion of Methane Using a Graphite Felt as Carbon-Based Catalyst In this example, the catalytic conversion process was carried out in the presence of a graphite felt (see material section above, 0.37 g GF) as carbon-based catalyst in a same manner as described in example 1. The graphite felt was heated by means of an electromagnetic induction heating device, while exposed to a methane-rich stream.

Catalytic conversion of methane was carried out in a tubular quartz reactor as described above for example 1. In this example, the reaction was carried out at 700° C. (obtained by induction heating), a total flow set to 25 ml/min (WHSV=1.5 h$^{-1}$); CH$_4$/Ar (1:1) and a reaction pressure of 0.1 MPa.

Figure 7:
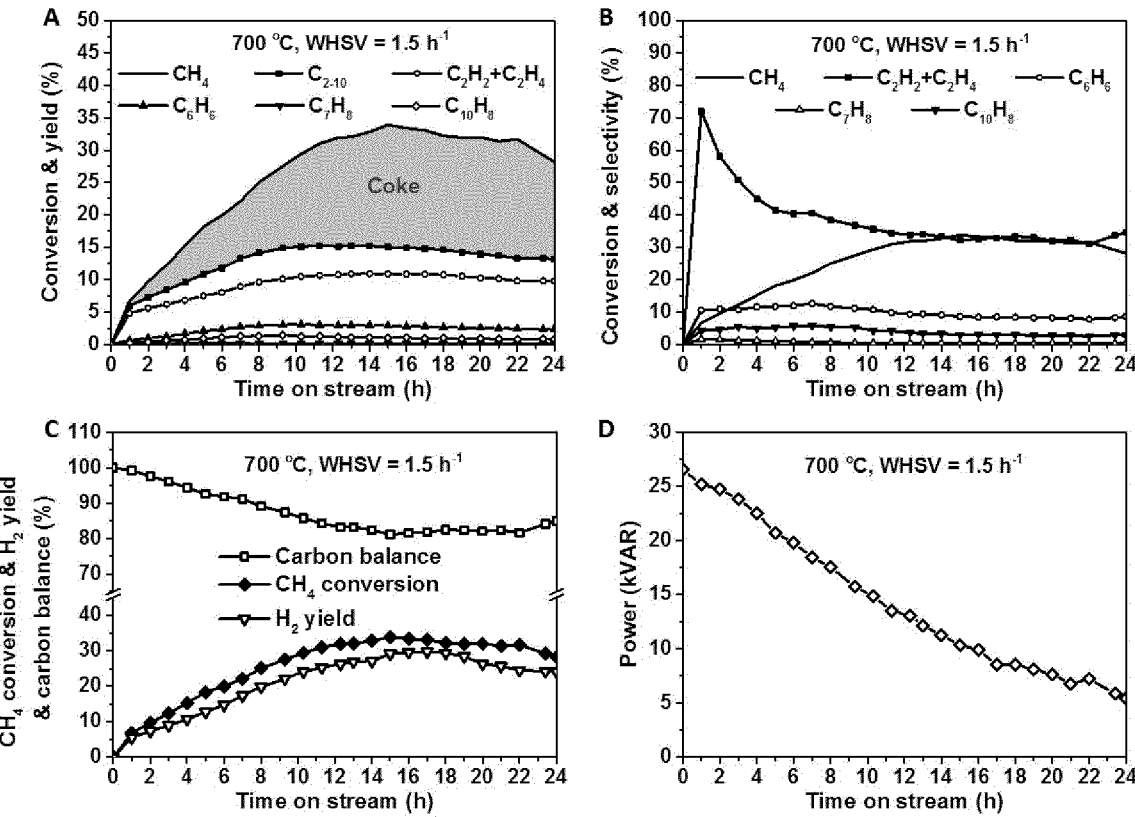

The methane conversion reaction performance on the graphite felt catalyst as a function of time on stream is displayed in FIG. 7. FIG. 7 represents product yield (FIG. 7A), product selectivity (FIG. 7B), carbon balance and hydrogen yield (FIG. 7C), and power supplied by induction heating device with time on stream on graphite felt (FIG. 7D). The difference between methane conversion and the sum of all hydrocarbon yields ($C_{2-10}$) represents the yield of coke species deposited on the catalyst surface.

As shown in FIG. 7, acetylene, ethylene, benzene, and toluene as well as naphthalene were produced during the conversion reaction of this example. Results for methane conversion, product yield and selectivity with time on stream were consistent with those reported for the same conditions in example 1 (see FIG. 3). Orders of yield and selectivity of different products were as follows: acetylene and ethylene>benzene>naphthalene>toluene. There was also an induction period on GF in the present example, during which the methane conversion and product yield kept increasing until they reached a stable level after about 15 h (FIG. 7A). Selectivity of acetylene and ethylene first reduced and then stabilized after 15 h, while selectivity of aromatic compounds increased until stable (FIG. 7B). The evolution of hydrogen yield was similar to that of methane conversion, while the evolution of the carbon balance was opposite to that of methane conversion (FIG. 7C). The power supplied by the induction heating device decreased with time on stream (FIG. 7D).

The results show that the graphite felt catalyst as applied in the present example is particularly suitable as metal-free catalyst for use in methane conversion; yielding an efficient production of acetylene and ethylene as well as a stable catalytic performance over time. The spent catalyst of the illustrated process may be recovered and constitutes a graphite derivative according to the invention.

Example 5: Non-Oxidative Conversion of Methane Using Graphite Felt as Carbon-Based Catalyst This example reports the catalytic conversion process of pure methane as carried out in the presence of a graphite felt catalyst (0.65 g GF—see material section above) in a same tubular quartz reactor set-up as used in example 1.

Figure 8:
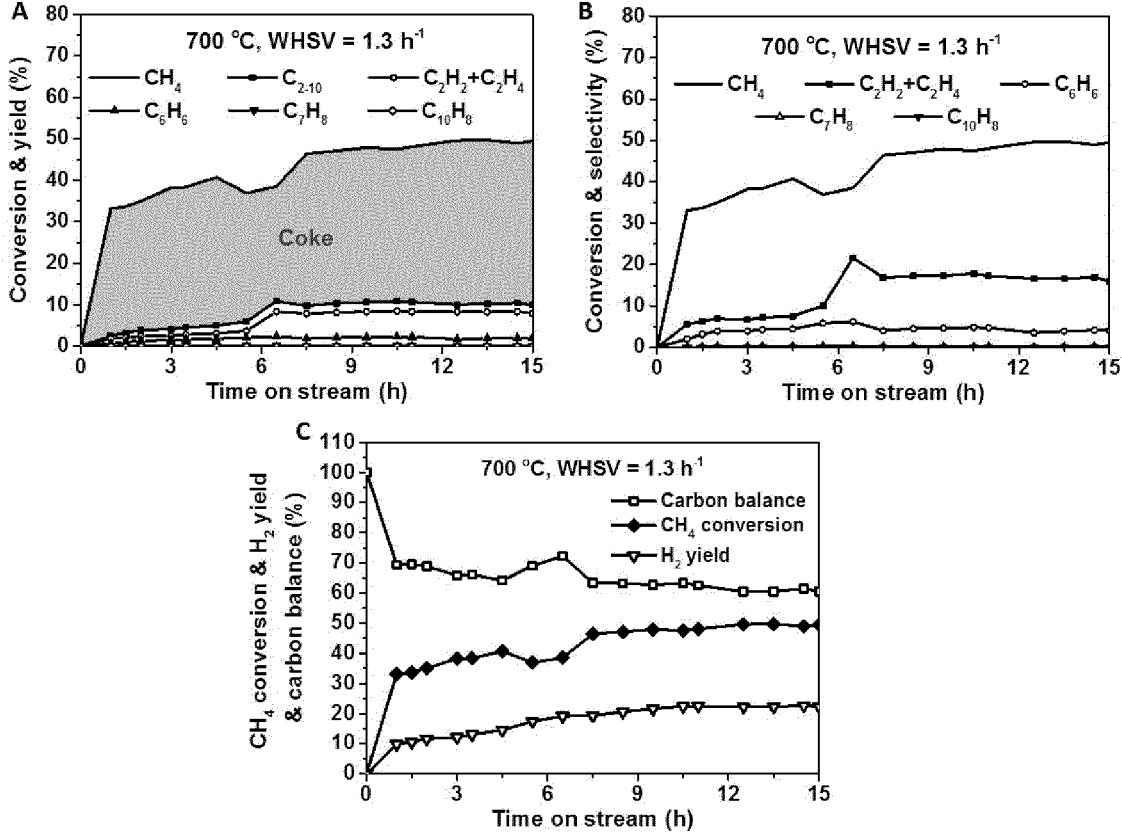

The graphite felt was heated by means of an electromagnetic induction heating device in a same manner as explained for example 1. The conversion reaction was operated under pure methane at 700° C. using induction heating, a total flow set to 20 ml/min methane (WHSV=1.3 $h^{-1}$); and a reaction pressure of 0.1 MPa. The methane conversion reaction performance on the graphite felt catalyst as a function of time on stream in this example is shown in FIG. 8. FIG. 8 represents product yield (FIG. 8A), product selectivity (FIG. 8B), and carbon balance and hydrogen yield (FIG. 8C). The difference between methane conversion and the sum of all hydrocarbon yields ($C_{2-10}$) represents the yield of coke species deposited on the catalyst surface.

As shown in FIG. 8, methane conversion and product yield increased slowly with time on stream, showing a long activation period before reaching stability after ca. 7 h of time-on-stream (FIG. 8A). In this example, $C_2+$ hydrocarbons contributed to about 10% yield (see FIG. 8B). The hydrogen yield slowly increased following the conversion during the reaction, while carbon balance slowly decreased (FIG. 8C). This pattern confirms the formation of coke during the reaction. The spent catalyst of the illustrated process may be recovered and constitutes a graphite derivative according to the invention.

Example 6: Non-Oxidative Conversion of Methane Using Graphite Felt as Carbon-Based Catalyst In this example, two layers of graphite felt (see material section above, 0.74 g, 2*GF) were used in a reaction for the catalytic conversion of methane using induction heating under high flow rate of 50 mL/min (CH$_4$/Ar=1:1) at 700° C. For the catalytic reactor configuration, a same configuration as explained for example 1 and as represented in FIG. 2 was used, with the difference that the graphite felt shown in FIG. 2 was replaced by 2 layers of graphite felt. The reaction was carried out at 700° C. (obtained by induction heating), a total flow set to 50 mL/min (WHSV=1.5 $h^{-1}$); CH$_4$/Ar (1:1) and a reaction pressure of 0.1 MPa.

Figure 9:
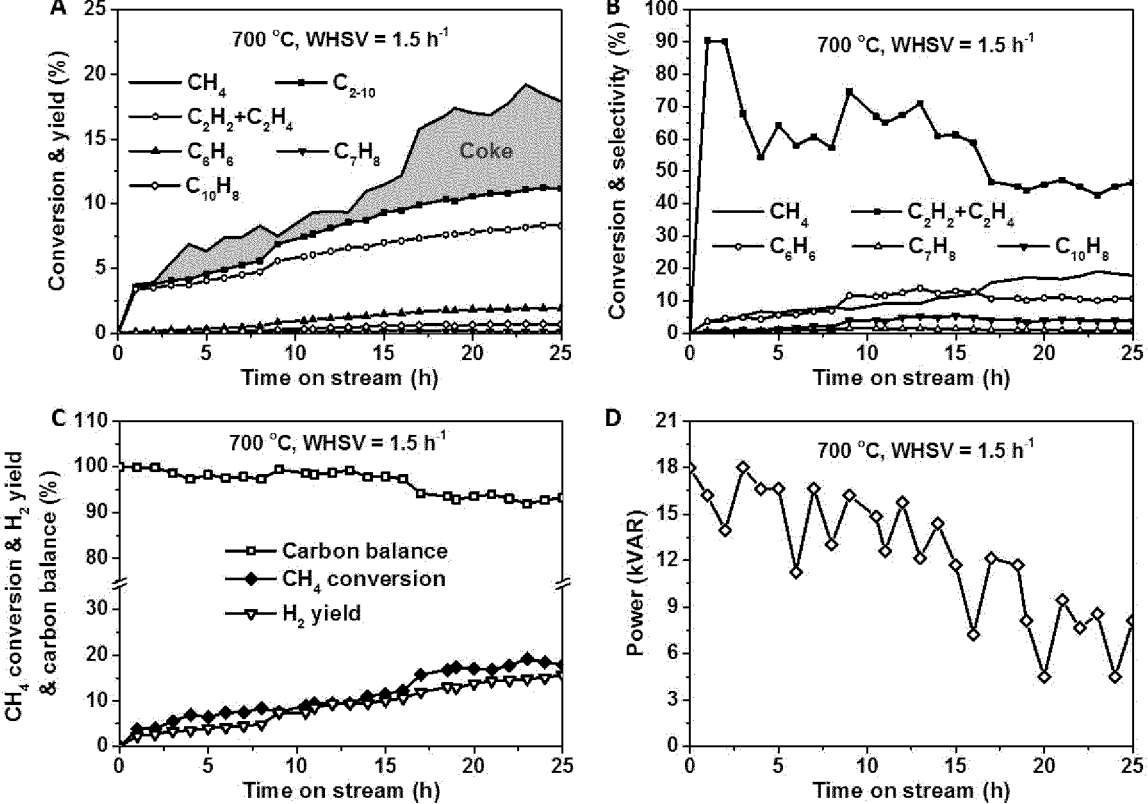

The methane conversion reaction performance on the carbon-based catalyst of graphite felt as a function of time on stream is displayed in FIG. 9. FIG. 9 represents product yield (FIG. 9A), product selectivity (FIG. 9B), carbon balance and hydrogen yield (FIG. 9C), and power supplied by induction heating device with time on stream on the two layers of graphite felt (FIG. 9D). The difference between methane conversion and the sum of all hydrocarbon yields ($C_{2-10}$) represents the yield of coke species deposited on the catalyst surface.

As shown in FIG. 9, methane conversion and product yield increased with time on stream (FIG. 9A). Acetylene and ethylene selectivity decreased at the beginning of the reaction while the aromatic selectivity increased. Selectivity stabilised towards the end of reaction (FIG. 9B). Hydrogen yield increased continuously during the reaction, while carbon balance decreased slowly (FIG. 9C). Furthermore, induction heating power decreased with time on stream during the reaction as shown in FIG. 9D, confirming the formation of coke during the reaction.

This example illustrates that also a double layer of graphite felt shows high catalytic activity and selectivity towards $C_2$ products. The example also demonstrates the formation of carbonaceous species during the reaction using this carbon-based catalyst, and the deposition thereof on the carbon-based catalyst. The spent catalyst of the illustrated process may be recovered and constitutes a graphite derivative according to the invention.

Example 7: Non-Oxidative Conversion of Methane Using a Graphite Felt as Carbon-Based Catalyst In this example, a "graphite felt 2" (0.32 g; GF2 or "new GF") (see material section above) was used as carbon-based catalyst in a non-oxidative conversion process steered by induction heating.

In this example, a same catalytic reactor configuration as used in example 1 and represented in FIG. 2 was used with the difference that the graphite felt shown in FIG. 2 was replaced by GF2. The reaction was carried out at 700° C. (obtained by induction heating), a total flow set to 25 ml/min (WHSV=1.7 $h^{-1}$); CH$_4$/Ar (1:1) and a reaction pressure of 0.1 MPa.

Figure 10:
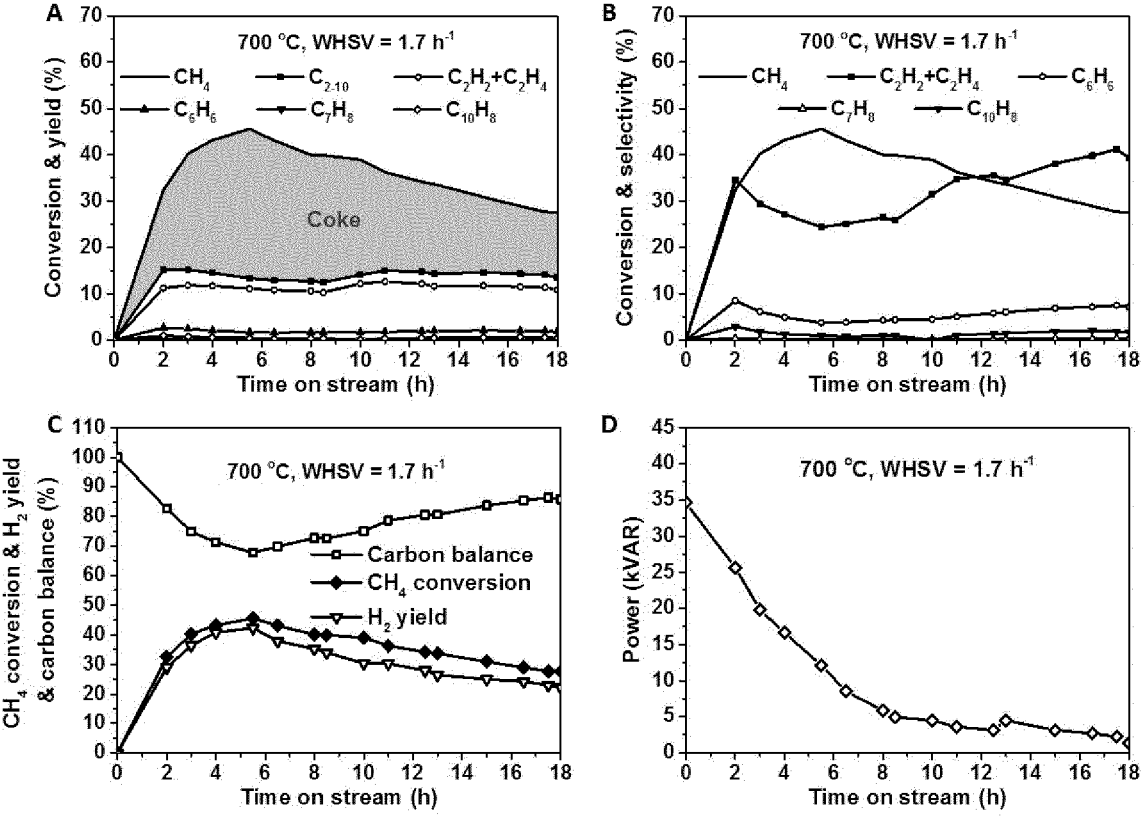

The methane conversion reaction performance on the catalyst as a function of time on stream is displayed in FIG. 10. FIG. 10 represents product yield (FIG. 10A), product selectivity (FIG. 10B), carbon balance and hydrogen yield (FIG. 10C), and power supplied by induction heating device with time on stream on GF2 (FIG. 10D). The difference between methane conversion and the sum of all hydrocarbon yields ($C_{2-10}$) represents the yield of coke species deposited on the catalyst surface.

As shown in FIG. 10, methane conversion first increased and then decreased and stabilised (FIG. 10A). $C_2+$ hydrocarbons were obtained at a yield approaching about 12% under the used reaction conditions. During the reaction product selectivity first decreased and then increased with time on stream due to a change of conversion and yield (FIG.

10B). The hydrogen yield pattern was similar to that of the methane conversion. Carbon balance first decreased and then increased (FIG. 10C). Considering the stable product yield during the reaction the decrease of methane conversion with time on stream is considered due to a decline of methane decomposition to coke. The induction heating power decreased with time on stream as shown in FIG. 10D.

Raman spectroscopy was performed (see method section above) to investigate the change in the graphitic structure of the GF2 after the conversion process. The Raman coefficients $I_D/I_G$ retrieved for the fresh and spent new GF catalyst were respectively: 0.81 (fresh) and 1.33 (spent).

Figure 11:
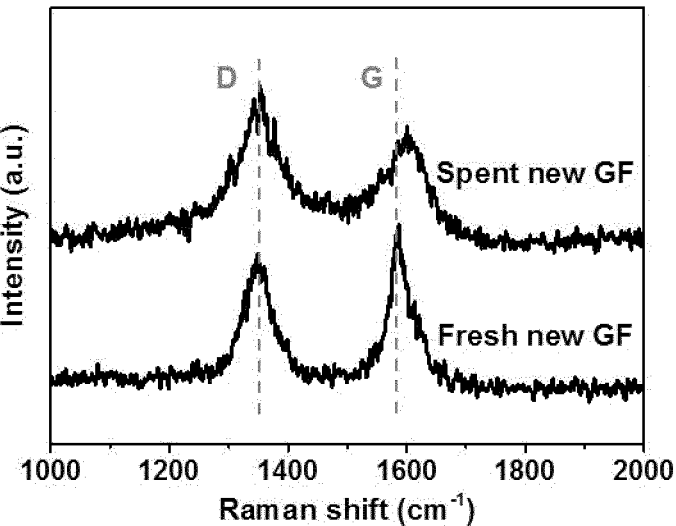
FIG. 11 represents the results of Raman spectrometry performed on a carbon-based catalyst before (fresh catalyst) and after (spent catalyst) the catalytic conversion reaction of example 7.

As shown in FIG. 11, both fresh and spent GF2 showed two bands of G (about 1580 cm$^{-1}$) and D (about 1350 cm$^{-1}$). After the reaction, the intensity of D band on spent GF2 was increased and the G band shifted to the higher wavelength compared to that of fresh GF2, confirming the presence of coke material with more defects and disordered graphitic fragments inside the spent sample. The spent catalyst of the illustrated process may be recovered and constitutes a graphite derivative according to the invention.

Example 8: Non-Oxidative Conversion of Methane Using a Carbon Nanofiber/Graphite Felt Composite as Carbon-Based Catalyst In this example, a carbon nanofiber/graphite felt (CNF/GF) composite as described in the materials section above was used as catalyst in a non-oxidative conversion reaction using induction heating.

In this example, a same catalytic reactor configuration as used in example 1 and represented in FIG. 2 was used with the difference that the graphite felt shown in FIG. 2 was replaced by a CNF/GF composite (0.89 g CNF/GF). The reaction was carried out at 700° C. (obtained by induction heating), a total flow set to 25 ml/min (WHSV=0.6 h$^{-1}$); CH$_4$/Ar (1:1) and a reaction pressure of 0.1 MPa.

Figure 12:
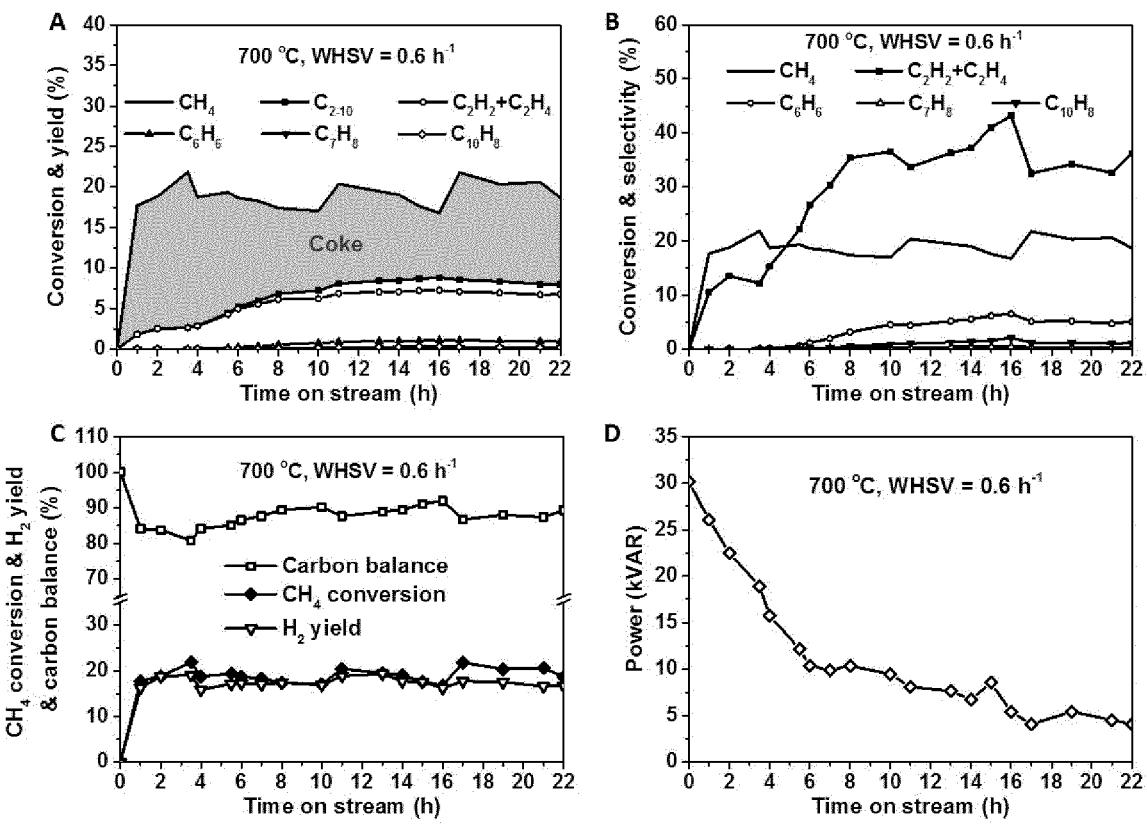

The methane conversion reaction performance on the carbon-based catalyst as a function of time on stream is displayed in FIG. 12. FIG. 12 represents product yield (FIG. 12A), product selectivity (FIG. 12B), carbon balance and hydrogen yield (FIG. 12C), and power supplied by induction heating device with time on stream on the carbon nanofiber/graphite felt (FIG. 12D). The difference between methane conversion and the sum of all hydrocarbon yields (C$_{2-10}$) represents the yield of coke species deposited on the catalyst surface.

As shown in FIG. 12, the CNF/GF catalysed conversion reaction showed stable methane conversion after a relatively short activation period. Product yield increased at the beginning to become stable with time on stream (FIG. 12A). There was an induction period during which product selectivity was increased (FIG. 12B). During such induction period, carbon balance was low, indicating that the dominant reaction was methane decomposition. The stability of hydrogen yield was similar to methane conversion (FIG. 12C). The carbon balance stabilised over time (FIG. 12C) and the induction heating power decreased with time on stream (FIG. 12D).

Figure 13:
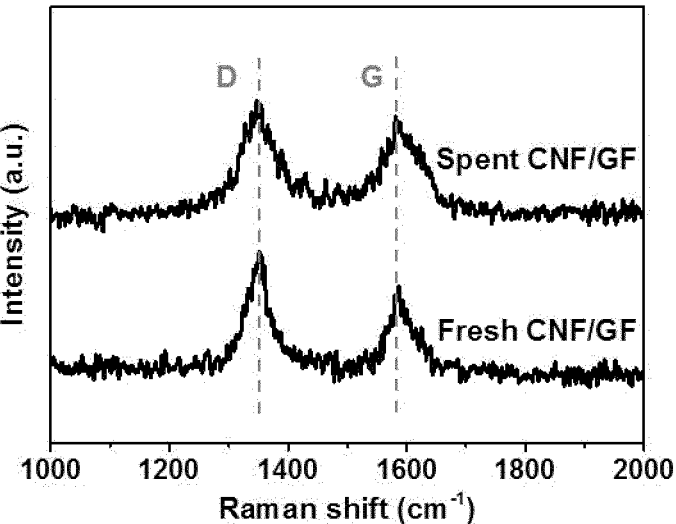
FIG. 13 represents the results of Raman spectrometry performed on a carbon-based catalyst before (fresh catalyst) and after (spent catalyst) the catalytic conversion reaction of example 8.

The spent catalyst of the illustrated process may be recovered and constitutes a graphite derivative according to the invention. Raman spectroscopy was performed to investigate the change in the graphitic structure of the CNF/GF catalyst obtained after the conversion process. As shown in FIG. 13, spent CNF/GF showed G (about 1580 cm$^{-1}$) and D (about 1350 cm$^{-1}$) bands which were similar to those of a sample of the fresh catalyst. The Raman coefficients $I_D/I_G$ retrieved for the fresh and spent CNF/GF catalyst were respectively: 1.43 (fresh) and 1.19 (spent).

Example 9: Non-Oxidative Conversion of Methane Using Natural Graphite as Carbon-Based Catalyst In this example, natural graphite (G) as described in the materials section above was used as carbon-based catalyst in a non-oxidative conversion reaction described herein and controlled by induction heating.

In this example, a same catalytic reactor configuration as used in example 1 and represented in FIG. 2 was used with the difference that the graphite felt shown in FIG. 2 was replaced, with the difference that the graphite felt shown in FIG. 2 was replaced by the present natural graphite (2.16 g G). The reaction was carried out at 700° C. (obtained by induction heating), a total flow set to 25 ml/min (WHSV=0.3 h$^{-1}$); CH$_4$/Ar (1:1) and a reaction pressure of 0.1 MPa.

Figure 14:
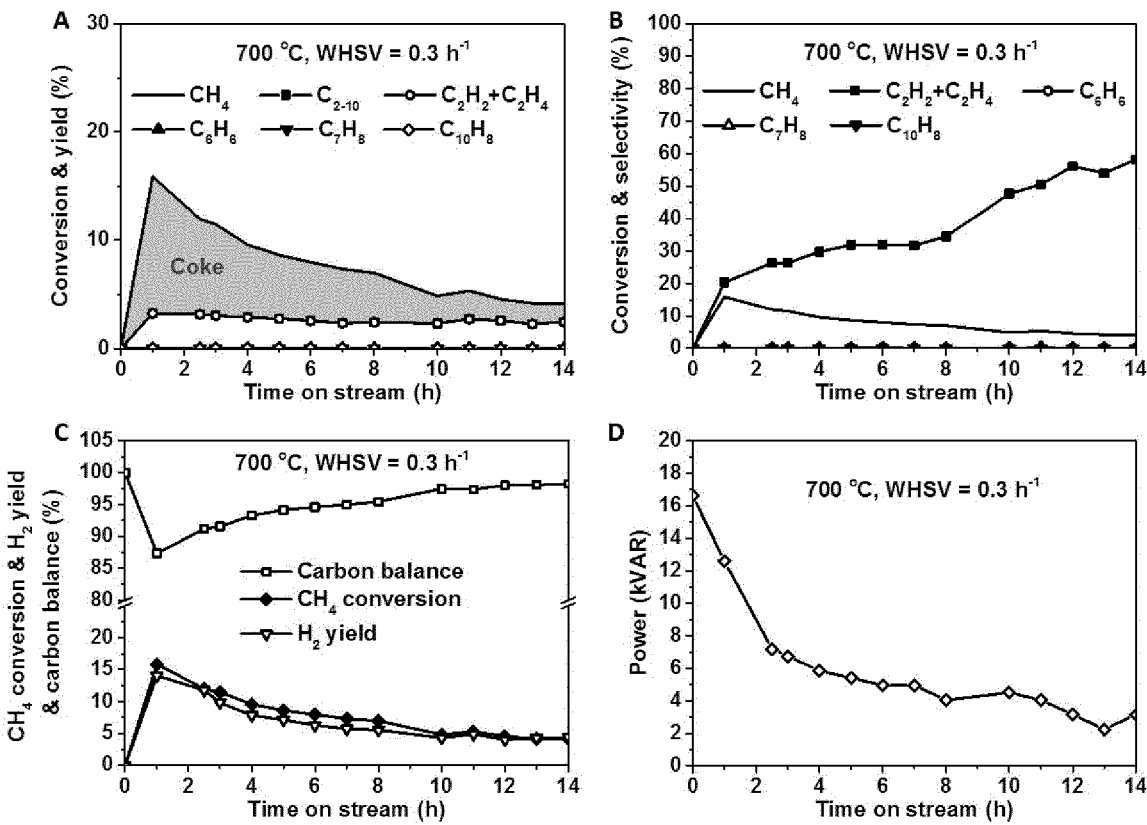

The methane conversion reaction performance on the graphite catalyst as a function of time on stream is displayed in FIG. 14. FIG. 14 represents product yield (FIG. 14A), product selectivity (FIG. 14B), carbon balance and hydrogen yield (FIG. 14C), and power supplied by induction heating device with time on stream on the natural graphite (FIG. 14D). The difference between methane conversion and the sum of all hydrocarbon yields (C$_{2-10}$) represents the yield of coke species deposited on the catalyst surface. As shown in FIG. 14, a stable C2 selectivity and absence of aromatics formation was observed (FIG. 14A-B) in this example. The power supply required from the induction heating device decreased with time on stream (FIG. 14D).

Figure 15:
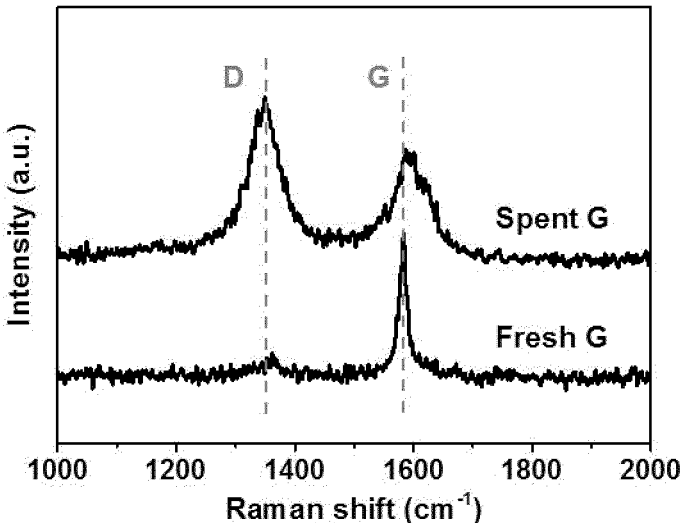
FIG. 15 represents the results of Raman spectrometry performed on a carbon-based catalyst before (fresh catalyst) and after (spent catalyst) the catalytic conversion reaction of example 9.

Raman spectroscopy was performed as explained above to investigate the change in the graphitic structure of the spent natural graphite catalyst used in this example. As shown in FIG. 15, the fresh catalyst showed a G band around 1580 cm$^{-1}$; while the spent catalyst showed two bands: a G band (around 1580 cm$^{-1}$) and a D band (around 1350 cm$^{-1}$), indicating a graphitic structure for the fresh G, and coke with more defects and disordered graphitic fragments inside the spent sample. The Raman coefficients $I_D/I_G$ retrieved for the fresh and spent G catalyst were respectively: 0.17 (fresh) and 1.5 (spent).

Example 10: Non-Oxidative Conversion of Methane Using Expanded Graphite (EG) as Carbon-Based Catalyst In this example, expanded graphite ("EG") as described in the materials section above was used as carbon-based catalyst in the non-oxidative conversion of methane steered by induction heating.

In this example, a same catalytic reactor configuration as used in example 1 and represented in FIG. 2 was used with the difference that the graphite felt shown in FIG. 2 was replaced by the expanded graphite (0.12 g EG). The reaction was carried out at total flow set to 25 ml/min (WHSV=4.6 h$^{-1}$); CH$_4$/Ar (1:1) and a reaction pressure of 0.1 MPa. The reaction was carried out at different reaction temperatures (see FIG. 16).

Figure 16:
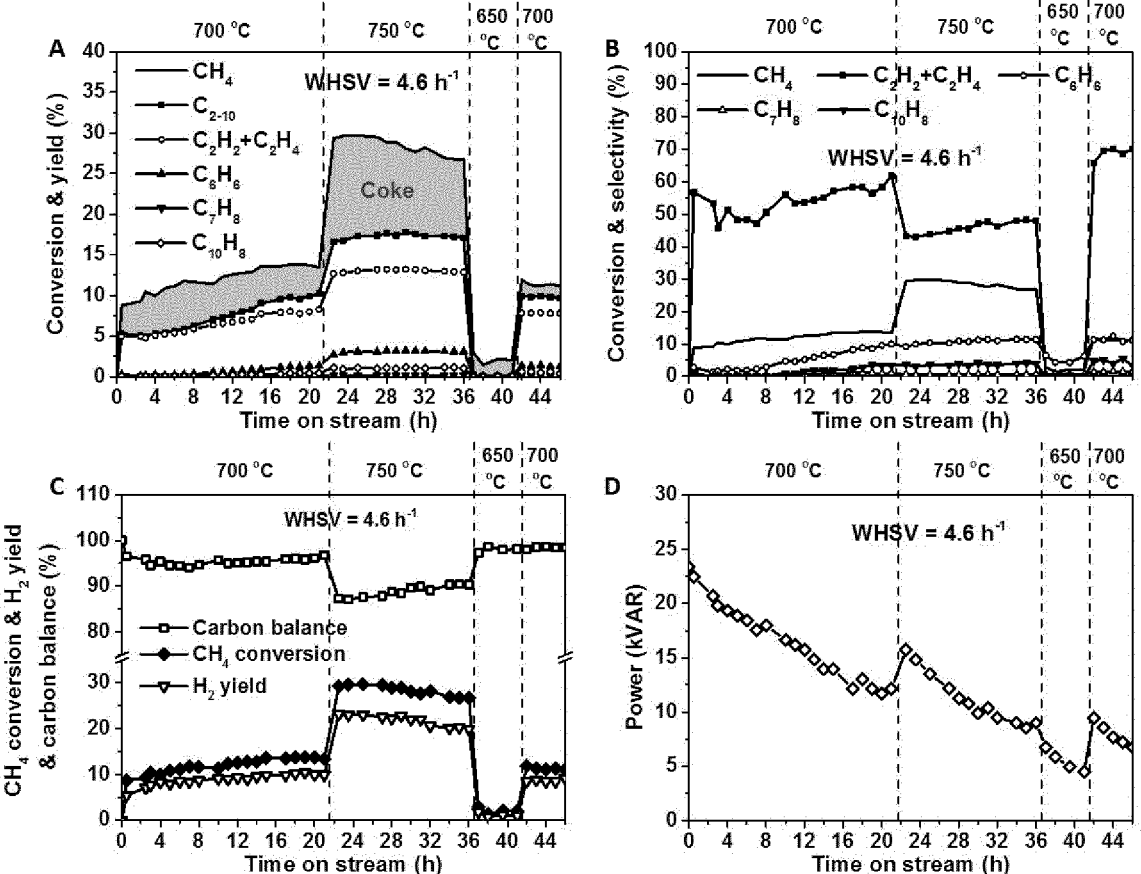

Performance of the methane conversion reaction on the expanded graphite catalyst as a function of time on stream is displayed in FIG. 16. FIG. 16 represents product yield (FIG. 16A), product selectivity (FIG. 16B), carbon balance and hydrogen yield (FIG. 16C), and power supplied by induction heating device with time on stream on the natural graphite (FIG. 16D). The difference between methane conversion and the sum of all hydrocarbon yields ($C_{2-10}$) represents the yield of coke species deposited on the catalyst surface.

As shown in FIG. 16, methane conversion and product yield and selectivity increased with time on stream at 700° C. before reaching a steady state (about 15% at 15 h). By increasing the reaction temperature to 750° C., conversion increased further to 25%. Increase in conversion was accompanied by an intensified coke formation (see FIGS. 16A and D). Even with the high coking rate, a stable $C_2$ yield (45%) was observed (FIG. 16B) which was not disturbed by a temporary temperature decrease (see part D in FIG. 16B). The power supplied by the induction heating device on expanded graphite followed the variation in reaction temperature and overall decreased with time on stream (FIG. 16D).

Example 11: Comparison of Different Carbon-Based Catalysts Used in a Catalytic Non-Oxidative Conversion Reaction of Methane In this example, catalytic performance of different carbon-based catalysts, i.e. graphite felt (GF), GF2 (herein also "new GF"), CNF/GF, graphite (G) and expanded graphite (EG) as described in the materials section above, when applied in a non-oxidative conversion reaction of methane was compared. In this example, heating conditions during conversion reaction are steered by induction heating.

In this example, a same catalytic reactor configuration as used in example 1 and represented in FIG. 2 was used with the difference that the graphite felt shown in FIG. 2 was replaced by each of the respective catalysts listed above. The reaction was carried out at 700° C., a total flow set to 25 ml/min; $CH_4/Ar$ (1:1) and a reaction pressure of 0.1 MPa.

Figure 17:
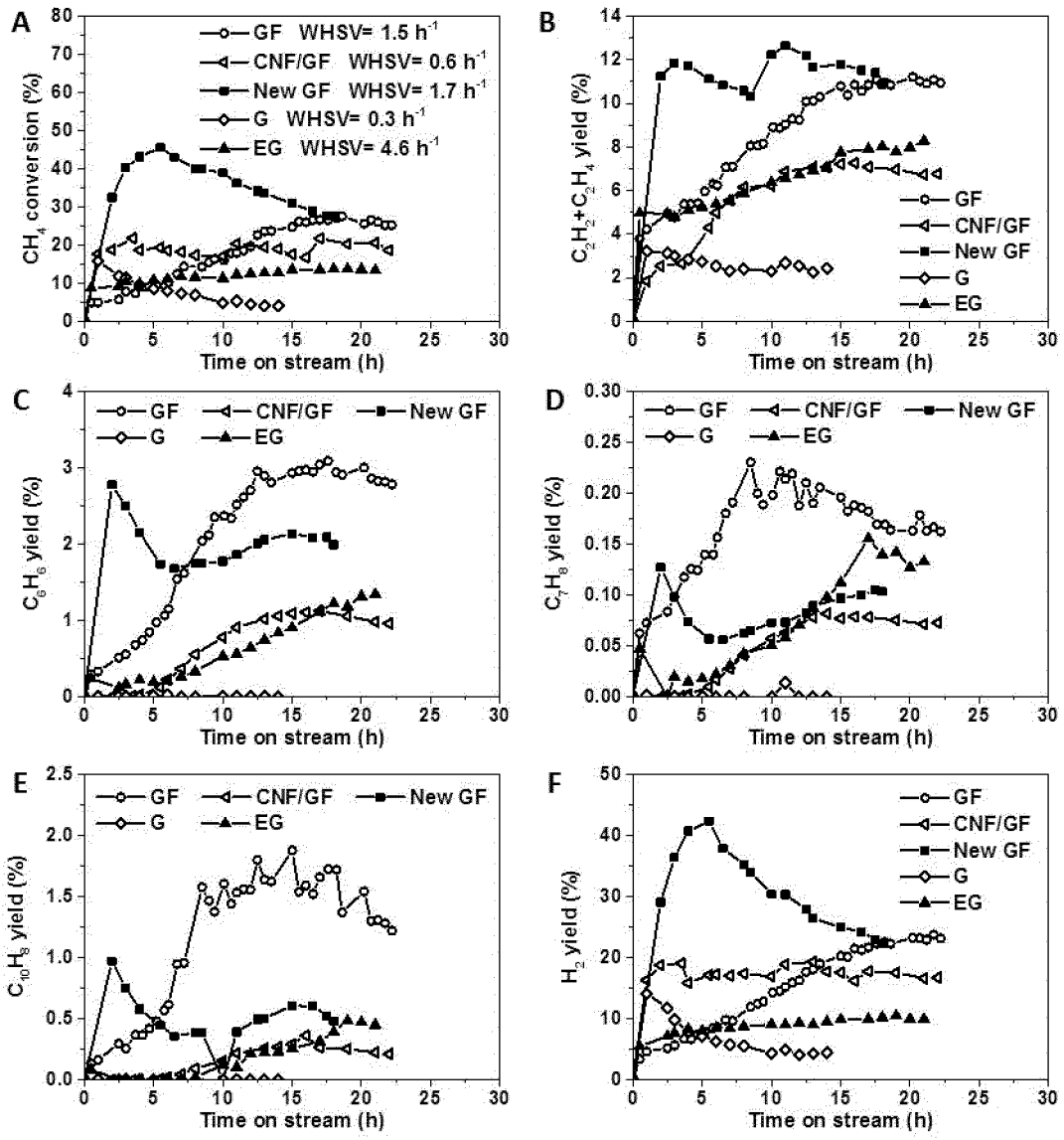

The following amounts of carbon-based catalyst were used in this example: 0.37 g GF (WHSV=1.5 $h^{-1}$), 0.32 g GF2 (WHSV=1.7 $h^{-1}$), 0.89 g CNF/GF (WHSV=0.6 $h^{-1}$), 2.16 g (WHSV=0.3 $h^{-1}$) and 0.12 g EG (WHSV=4.6 $h^{-1}$). The density of the tested carbon-based catalysts was not the same. Therefore, in order to facilitate a comparison of their catalytic performance, different weights were used for the different catalyst samples to ensure a same thickness of the catalysts in the reactor as well as a same residence time during the reaction. Therefore, the WHSV for each catalyst experiment was different, as shown on FIG. 17A. A comparison between performances on the different types of carbon-based catalysts is shown in FIG. 17 in terms of methane conversion (FIG. 17A) and product yield (FIG. 17B-E) and hydrogen yield (FIG. 17F). These results confirm suitability of all tested carbon-based catalysts in a non-oxidative conversion process. Among the carbon-based catalysts, GF2 showed the highest methane conversion, however, methane conversions decreased towards the end of reaction with this catalyst. GF displayed the longest activation period, while methane conversions of CNF/GF and GF slowly increased with time on stream (see FIG. 17A). Acetylene and ethylene were formed during all reactions; acetylene and ethylene yield on GF2 was the highest among the tested catalysts. Acetylene and ethylene yield was increased on GF, CNF/GF and EG catalysts with time on stream while it was relatively stable on GF2 and G (FIG. 17B).

FIG. 17C-E further show that the GF catalyst displayed the highest yields of benzene and toluene as well as naphthalene and these yields increased at the beginning of reaction and then became stable with time on stream. Negligible aromatic products were formed on G. Aromatic yields on CNF/GF and EG increased with time on stream; while aromatic yield on GF2 was decreased first and then increased. During all catalysed reactions in this example, lower toluene yields were observed as compared to the yields for benzene or naphthalene.

A similar trend of hydrogen yield with time on stream was observed for all catalysed reactions (FIG. 17F), and the pattern was similar to the corresponding methane conversion pattern (FIG. 17A). GF2 displayed the highest hydrogen yield, hence produced more hydrogen compared to the catalysts tested in this example. In this example, the EG catalyst seemed to display the highest performance as compared to the other tested catalysts in view of the fact that this catalyst was tested under the highest WHSV.

Figure 18:
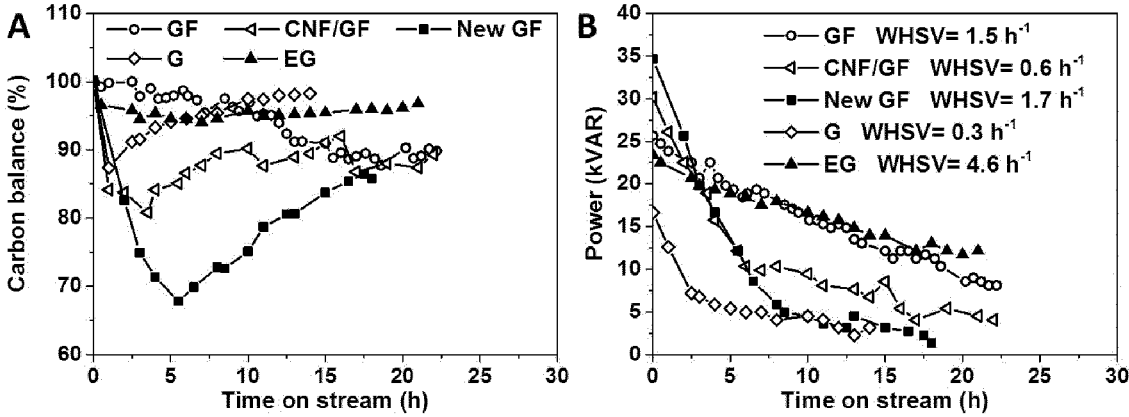

FIG. 18 provides a comparison of carbon balance (FIG. 18A) and power supplied by an induction heating device (FIG. 18B) as registered for the different catalytic reactions in this example using GF, GF2 ("new GF"), CNF/GF, G and EG. The GF2 used in this example had the lowest carbon balance while G displayed the highest one carbon balance (FIG. 18A). FIG. 18B shows the power supplied by an induction heating device in the different reactions, for all reactions, the power decreased with time on stream, which confirms the formation of carbon deposits on the tested catalysts during the conversion reactions. Such deposits enhanced the conversion of electromagnetic energy into heat under induction heating, due to an increase of electrical conductor per volume of sample inside the inductive coil. The difference in initial power for the different reactions is linked to the nature of the carbon-based catalyst used.

Figure 19:
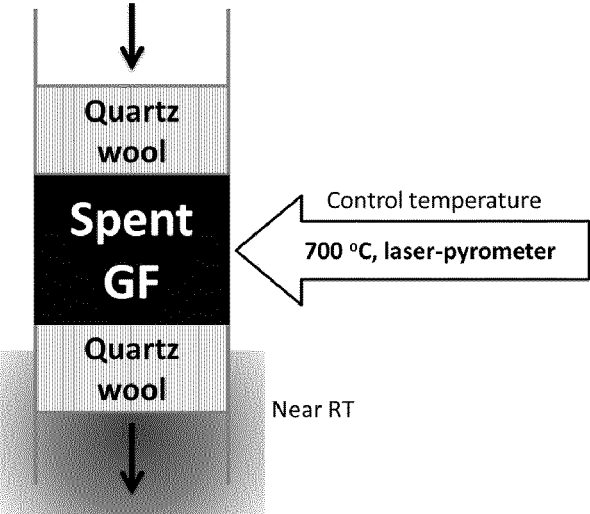
FIG. 19 provides a schematic illustration of an embodiment of a catalytic reactor using a spent catalyst (graphite derivative) as carbon-based catalyst and using induction heating to heat the catalyst.

Example 12: Non-Oxidative Conversion of Methane Using a Graphite Derivative as Carbon-Based Catalyst In this example, a graphite derivative (spent catalyst) was used as catalyst in a conversion reaction of a methane reach stream. FIG. 19 shows the reactor configuration using spent GF as catalyst under induction heating in accordance with this example. The reaction was carried out at 700° C. (obtained by induction heating), a total flow set to 25 ml/min (WHSV=1.3 $h^{-1}$); $CH_4/Ar$ (1:1) and a reaction pressure of 0.1 MPa.

Figure 20:
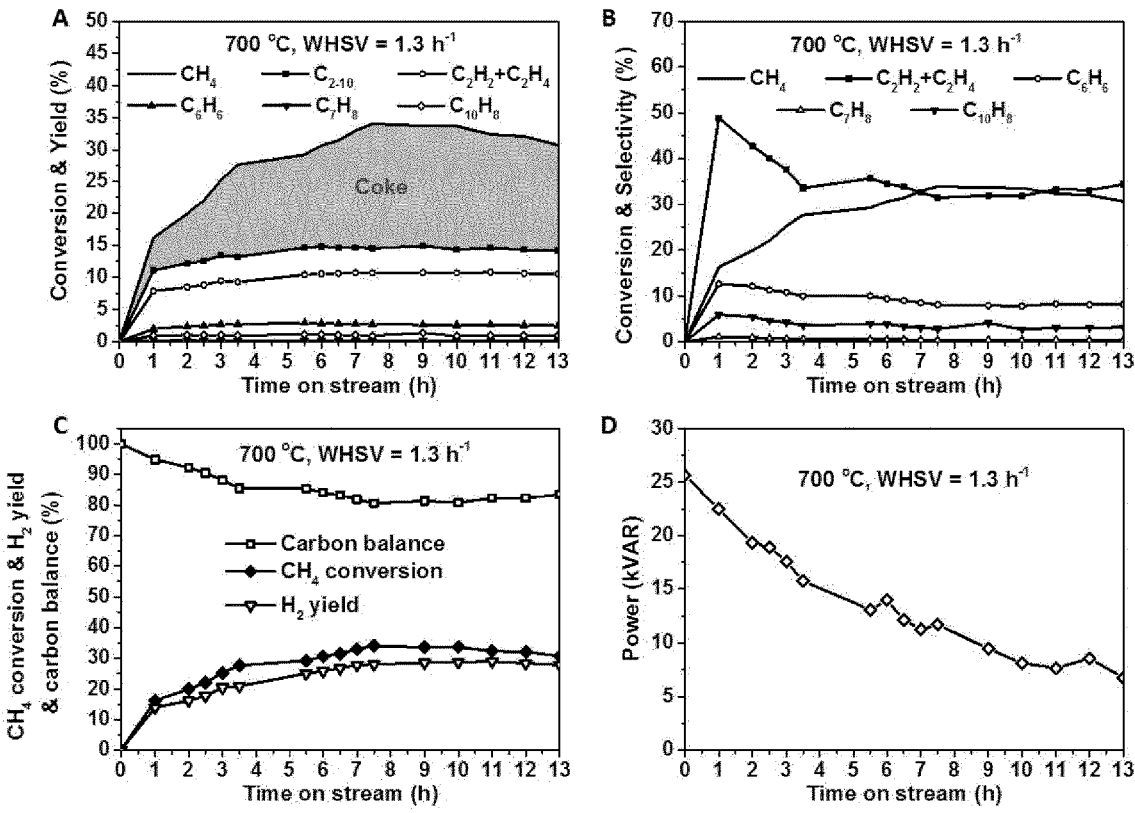

The methane conversion reaction performance on the tested catalyst as a function of time on stream is displayed in FIG. 20. The methane conversion and product yield on spent GF are shown in FIG. 20A. Acetylene and ethylene, benzene, and toluene as well as naphthalene were produced on spent GF during the conversion reaction. Both the conversion and product yield with time-on-stream increased. The difference between methane conversion and the sum of all hydrocarbon yields ($C_{2-10}$) suggested that more and more carbon was deposited on the catalyst with time on stream before reaching a steady-state after about 13 h on stream. Selectivity decreased with increase of conversion and stabilised after about 6 hours (FIG. 20B). Hydrocarbon yield, and especially acetylene and ethylene yield were high on the spent GF catalyst under the tested reaction conditions. The variation of hydrogen yield was similar to that of methane conversion on the sample as shown in FIG. 20C while the variation of carbon balance was opposite to that of methane conversion. The power supplied by induction heating device decreased with time on stream (FIG. 20D).

Figure 21:
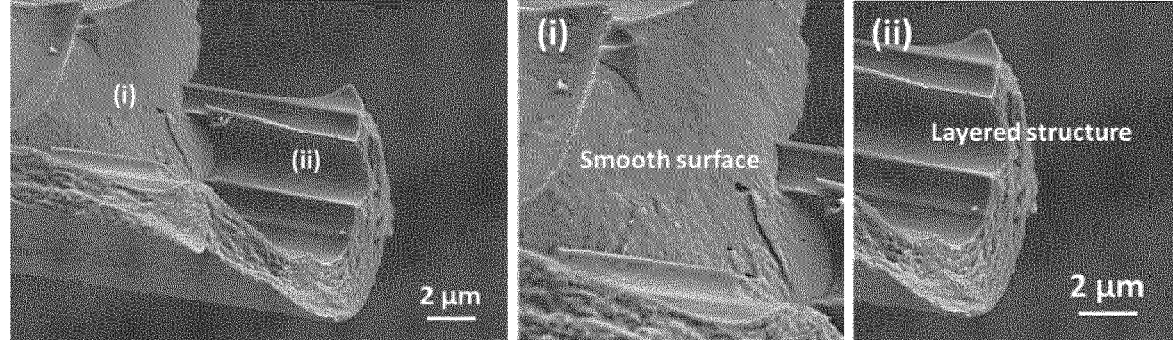
FIG. 21 represents SEM analyses performed on the graphite derivative (spent GF catalyst) as used in the catalytic conversion reaction reported in example 12.

FIG. 21 represents SEM analyses performed on the spent catalyst (spent GF catalyst) as used in this example.

US 12,686,653 B2

63

64

Example 13: Non-Oxidative Conversion of
Methane Using a Graphite Felt as Carbon-Based
Catalyst Heated by Induction Heating or by
Conventional (Joule) Heating This example illustrates a non-oxidative dehydrogenation reaction according to the invention using (1) induction heating, i.e. when applying a magnetic field, followed by (2) conventional heating.

In a first step, a non-oxidative dehydrogenation reaction was carried out over a graphic felt catalyst using induction heating. The same reactor set-up with induction heater coil as explained above under the "Methods" section was applied in the present example. The reaction was carried out in the presence of a graphite felt (also denoted as "GF", see material section above) sample. The graphite felt was heated by means of an electromagnetic induction heating device, while exposed to a methane stream. The catalyst was activated during 3 hours using the following conditions: 100 mL/min methane stream at 770° C.

Figure 22A:
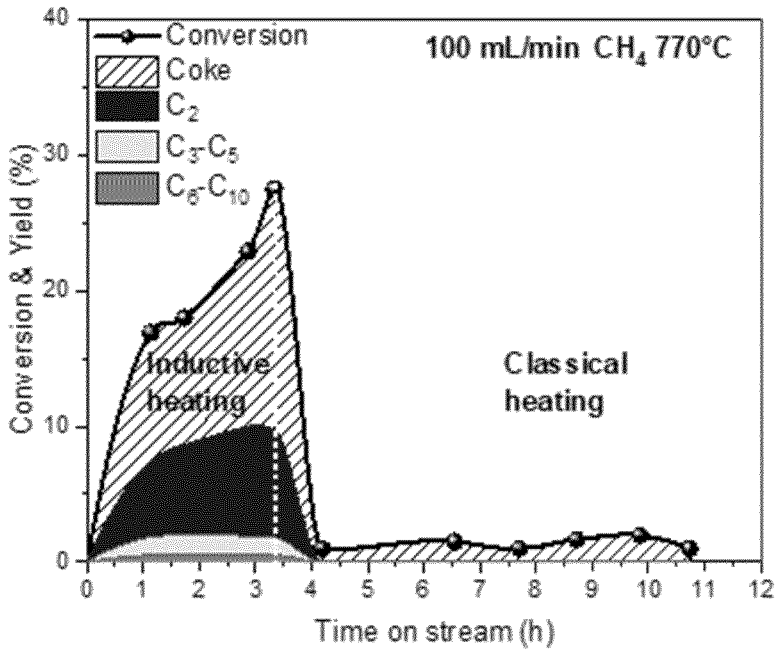
FIG. 22A represents product yield.

The methane conversion reaction performance and product yield on the graphite felt catalyst as a function of time on stream is displayed in FIG. 22A. The reaction yielded high levels of methane conversion and $C_2$ (mostly olefins) yield (see FIG. 22A), product selectivity (FIG. 22B), and power supplied by induction heating device with time on stream on graphite felt (FIG. 22C). The difference between methane conversion and the sum of all hydrocarbon yields ($C_{2-10}$) represents the yield of coke species deposited on the catalyst surface.

In a next step, without removing the catalyst from the quartz tube reactor set-up, the induction heating coil was removed, and the quartz tube was placed inside a conventionally heated (i.e. Joule heated) furnace where the reaction was restarted. As shown in FIGS. 22A and C, methane conversion and product yield from the graphite felt heated to 770° C. by indirect Joule heating were very low in comparison to those obtained by induction heating. At 770° C. the methane conversion reached merely 2% and the $C_2$ distribution significantly changed. Under Joule heating, the selectivity to ethane was stable at more than 70% and there was no selectivity to acetylene (see FIG. 22B).

Figure 22B:
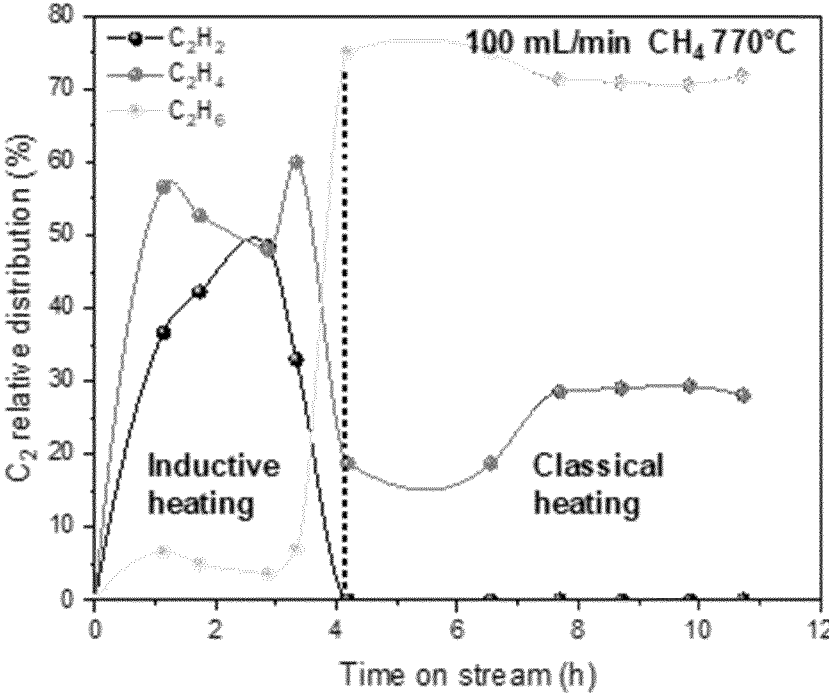
FIG. 22B represents product selectivity.
Figure 22C:
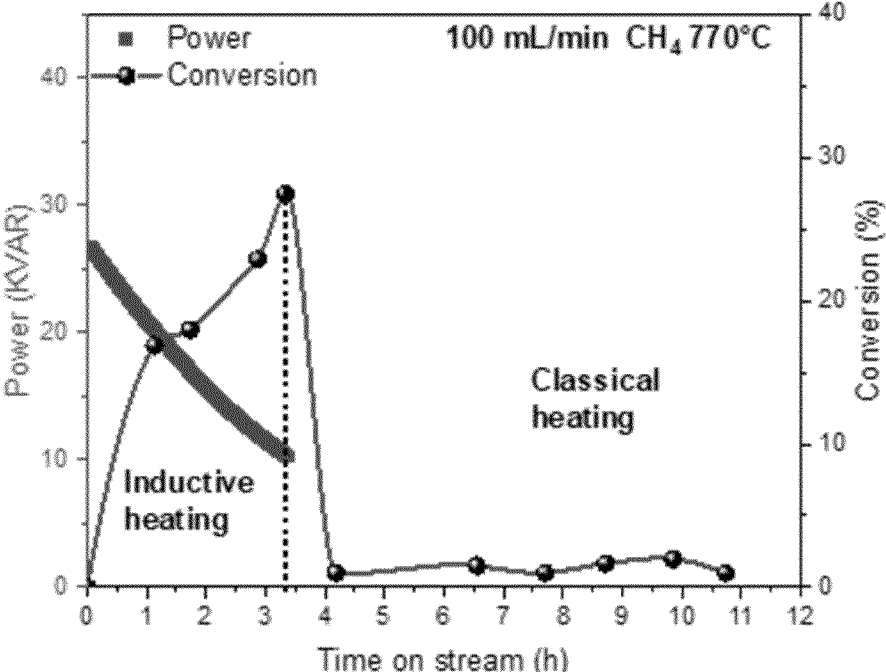
FIG. 22C represents power supplied by induction heating device with time on stream on the graphite felt. Conditions were as follows: 770° C., 0.1 MPa, 100 mL/min $CH_4$, 0.49 g GF, and WHSV=8.1 $h^{-1}$.

Under induction heating, ethylene and acetylene were the main $C_2$ products (see FIG. 22B). In joule heated setup the heat is delivered from the furnace wall to the center of the reaction zone, hence the warmer sections are in the reactor walls. Inversely, in the inductively heated setup the warmer section is in the center of the reactor. A significant change in $C_2$ fraction selectivity was observed when changing from induction heating to conventional heating, which indicates that the heating mode not only influences methane conversion, but also the reaction mechanism for producing olefins In summary, the catalytic performance of a carbon based catalyst as reported herein under inductive heating conditions is largely superior, and more selective, at the same temperature as compared to conventional heating thereof.

The invention claimed is:
1. A process for the non-oxidative conversion of saturated $C_{1+}$ hydrocarbons into unsaturated $C_{2+}$ hydrocarbons and hydrogen in the presence of an unsupported carbon-based catalyst having a carbon content of at least 90.0 wt % and a metal concentration which is less than 0.3 wt %; with wt % expressed based on the total weight of said carbon-based catalyst, wherein the process comprises the steps of:
a) supplying said carbon-based catalyst to a reaction zone,
b) directly heating of said carbon-based catalyst contained in said reaction zone by means of induction heating thereby indirectly heating the reaction zone containing said carbon-based catalyst to a reaction temperature of at least 350° C.;
c) supplying a reaction gas comprising saturated $C_{1+}$ hydrocarbons to said heated reaction zone comprising said carbon-based catalyst; and
d) subjecting said reaction gas to a non-oxidative conversion in the presence of said carbon-based catalyst in said heated reaction zone thereby converting at least a portion of said saturated $C_{1+}$ hydrocarbons into unsaturated $C_{2+}$ hydrocarbons and hydrogen.

2. Process according to claim 1, comprising at least 92.0 wt %, or at least 95.0 wt %, or at least 96.0 wt %, or at least 97.0 wt %, or at least 98.0 wt %, or at least 99.0 wt %, or at least 99.5 wt %, or at least 99.9 wt %, of carbon, based on the total weight of said carbon-based catalyst.

3. Process according to claim 1, wherein said carbon-based catalyst has a metal concentration which is less than 0.2 wt %, or less than 0.1 wt %, or less than 0.05 wt %, or less than 0.03 wt %, or less than 0.01 wt %, or less than 0.005 wt %, based on the total weight of the carbon-based catalyst.

4. Process according to claim 1, wherein said carbon-based catalyst comprises less than 10.0 wt %, or less than 5.0 wt %, or less than 3.0 wt % of inorganic oxide(s), based on the total weight of the carbon-based catalyst.

5. Process according to claim 1, wherein said carbon-based catalyst consists of,
(i) at least 95.0 wt %, or at least 97.0 wt %, or at least 99.0 wt %, or at least 99.5 wt % of carbon; with wt % based on the total weight of the carbon-based catalyst;
(ii) from 0 to 5.0 wt %, or from 0 to 1.0 wt %, or from 0 to 0.5 wt %, or from 0 to 0.1 wt % of inorganic oxide(s); with wt % based on the total weight of the carbon-based catalyst; and
(iii) from 0 to 0.3 wt %, or from 0 to 0.1 wt %, or from 0 to 0.01 wt %, or from 0 to 0.001 wt % of metal, with wt % based on the total weight of the carbon-based catalyst.

6. Process according to claim 1, wherein said carbon-based catalyst is characterised by a Raman spectrum, as determined by Raman Spectroscopy using an excitation wavelength of about 532 nm and exciting laser power of about 100 milliwatt (mW); showing a first peak (D peak) at a wavenumber of about 1350 cm$^{-1}$ and a second peak (G peak) at a wavenumber from about 1585 to about 1600 cm$^{-1}$, and wherein said carbon-based catalyst has a Raman coefficient $I_D/I_G$ which is higher than 0.10,
wherein $I_D$ corresponds to the intensity of the Raman spectrum in said D peak; and $I_G$ corresponds to the intensity of the Raman spectrum in said G peak.

7. Process according to claim 1, wherein said carbon-based catalyst has a BET surface area of at most 500 m$^2$/g, or at most 200 m$^2$/g, or at most 50 m$^2$/g, or at most 20 m$^2$/g, or at most 15 m$^2$/g, or at most 10 m$^2$/g as determined by ASTM-D-3663 (2020).

8. Process according to claim 1, wherein the carbon-based catalyst has a BET surface area of at most 5.0 m$^2$/g as determined by ASTM-D-3663 (2020), or from 0.10 to 5.0 m$^2$/g, or from 0.5 to 3.0 m$^2$/g, or from 1.0 to 5.0 m$^2$/g, or from 1.0 to 3.0 m$^2$/g, as determined by ASTM-D-3663 (2020).

9. Process according to claim 1, wherein said carbon-based catalyst has an electric resistivity of between $10^{-7}$ and $10^2$ ohm·m at 20° C. as determined by ASTM C611-98 (2016).

10. Process according to claim 1, wherein said carbon-based catalyst is selected from the group consisting of graphite (G), carbon felt (CF), graphite felt (GF), expanded graphite (EG), graphite fabric, graphite cloth, carbon nanofiber (CNF), carbon nanotubes (CNTs), graphene, few-layer graphene (FLG), and any combinations thereof.

11. Process according to claim 1, wherein said carbon-based catalyst is heated by generating an alternating electromagnetic field within the reaction zone containing said carbon-based catalyst upon energization by a power source supplying alternating current, where the alternating electromagnetic field passes through the reaction zone thereby generating an electric current in said carbon-based catalyst and heating the carbon-based catalyst.

12. Process according to claim 1, wherein said reaction zone containing said carbon-based catalyst is heated to a reaction temperature of at least 400° C., or at least 450°, or at least 500° C., or at least 550° C., or at least 650° C., or at least 700° C., or at least 750° C., or at least at 800° C.

13. Process according to claim 1, wherein said reaction zone containing said carbon-based catalyst is heated to a reaction temperature which is lower than 2000° C., or lower than 1500° C., or lower than 1300° C., or lower than 1100° C.

14. Process according to claim 1, wherein said non-oxidative hydrocarbon conversion process is carried out at a reaction pressure comprised between 0.1 and 30.0 bar, or between 0.1 and 20.0 bar, or between 0.1 and 15.0 bar, or between 0.1 and 10.0 bar or between 0.5 and 5.0 bar.

15. Process according to claim 1, wherein said reaction gas is supplied to said reaction zone at a weight hourly space velocity (WHSV) of between 0.1 and 100 h$^{-1}$, or between 0.1 and 50 h$^{-1}$, or between 0.1 and 10 h$^{-1}$.

16. Process according to claim 1, wherein said saturated $C_{1+}$ hydrocarbons comprise saturated $C_1$-$C_{12}$ hydrocarbons, or saturated $C_1$-$C_{10}$ hydrocarbons, or saturated $C_1$-$C_8$ hydrocarbons, or saturated $C_1$-$C_6$ hydrocarbons, or saturated $C_1$-$C_4$ hydrocarbons.

17. Process according to claim 1, wherein said reaction gas comprises at least 50.0 mol % or at least 75.0 mol % or at least 90.0 mol % or at least 95.0 mol % or at least 99.0 mol % of saturated $C_{1+}$ hydrocarbons.

18. Process according to claim 1, wherein said unsaturated $C_{2+}$ hydrocarbons comprise alkenes, or $C_2$-$C_{12}$ alkenes, or $C_2$-$C_{10}$ alkenes, or $C_2$-$C_8$ alkenes, or $C_2$-$C_6$ alkenes, or $C_2$-$C_4$ alkenes, or ethylene.

19. Process according to claim 1, wherein said unsaturated $C_{2+}$ hydrocarbons comprise alkynes, or $C_2$-$C_{12}$ alkynes, or $C_2$-$C_{10}$ alkynes, or $C_2$-$C_8$ alkynes, or $C_2$-$C_6$ alkynes, or $C_2$-$C_4$ alkynes, or acetylene.

20. Process according to claim 1, wherein said unsaturated $C_{2+}$ hydrocarbons comprise aromatic hydrocarbons, or $C_{6+}$ aromatic hydrocarbons, or aromatic $C_6$-$C_{12}$ hydrocarbons, or benzene, or toluene, or naphthalene, or any combinations of two or more thereof.

21. Process according to claim 1, further comprising the steps of
  e) recovering at least a portion of the carbon-based catalyst from said reaction zone after step d), thereby obtaining a graphite derivative,
  f) optionally, subjecting the graphite derivate to a mechanical treatment to reduce the size of the said graphite derivative, and
  g) optionally using at least a portion of the graphite derivative recovered in step e) or f) as a carbon-based catalyst.

22. Process according to claim 21, further comprising the step of supplying the recovered graphite derivative as a carbon-based catalyst in step a).

* * * * *